United States Patent
Skelton et al.

(10) Patent No.: US 8,175,720 B2
(45) Date of Patent: May 8, 2012

(54) POSTURE-RESPONSIVE THERAPY CONTROL BASED ON PATIENT INPUT

(75) Inventors: Dennis M. Skelton, Bloomington, MN (US); Jon P. Davis, St. Michael, MN (US); Shahram Malekkhosravi, Maple Grove, MN (US); Antonio N. Bucalo, Louisville, KY (US)

(73) Assignee: Medtronic, Inc., Minneapolis, MN (US)

( * ) Notice: Subject to any disclaimer, the term of this patent is extended or adjusted under 35 U.S.C. 154(b) by 402 days.

(21) Appl. No.: 12/433,599

(22) Filed: Apr. 30, 2009

(65) Prior Publication Data

US 2010/0280440 A1 Nov. 4, 2010

(51) Int. Cl.
*A61N 1/365* (2006.01)
(52) U.S. Cl. ........................................ 607/62
(58) Field of Classification Search .................... 607/46, 607/60–62

See application file for complete search history.

(56) References Cited

U.S. PATENT DOCUMENTS

| | | |
|---|---|---|
| 4,297,685 A | 10/1981 | Brainard, II |
| 4,365,633 A | 12/1982 | Loughman |
| 4,543,955 A | 10/1985 | Schroeppel |
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |

(Continued)

FOREIGN PATENT DOCUMENTS

DE 19831109 1/2000

(Continued)

OTHER PUBLICATIONS

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.

(Continued)

*Primary Examiner* — Carl H Layno
*Assistant Examiner* — Paula J Stice
(74) *Attorney, Agent, or Firm* — Shumaker & Sieffert, P.A.

(57) ABSTRACT

Patient efficacy inputs are received over a period of time during which posture-responsive therapy is delivered to the patient while the patient occupies a plurality of posture states. The patient inputs are correlated with the times at which the inputs were received, a sensed posture state of the patient, and a therapy program defining therapy delivery at each of the times the posture state was sensed. Posture-responsive therapy is adjusted based on the historical posture-responsive therapy information correlating the patient input, patient input time, sensed posture state, and therapy program.

45 Claims, 18 Drawing Sheets

U.S. PATENT DOCUMENTS

| | | |
|---|---|---|
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,044,297 A | 3/2000 | Sheldon et al. |
| 6,045,513 A | 4/2000 | Stone et al. |
| 6,059,576 A | 5/2000 | Brann |
| 6,083,475 A | 7/2000 | Shackle et al. |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Himbert et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |

| | | | | | | |
|---|---|---|---|---|---|---|
| 7,366,572 B2 | 4/2008 | Heruth et al. | | 2005/0209644 A1 | 9/2005 | Heruth et al. |
| 7,387,610 B2 | 6/2008 | Stahmann | | 2005/0209645 A1 | 9/2005 | Heruth et al. |
| 7,389,147 B2 | 6/2008 | Wahlstrand et al. | | 2005/0215847 A1 | 9/2005 | Heruth et al. |
| 7,395,113 B2 | 7/2008 | Heruth | | 2005/0215947 A1 | 9/2005 | Heruth et al. |
| 7,403,820 B2 | 7/2008 | DiLorenzo | | 2005/0216064 A1 | 9/2005 | Heruth et al. |
| 7,406,351 B2 | 7/2008 | Wesselink | | 2005/0222522 A1 | 10/2005 | Heruth et al. |
| 7,415,308 B2 | 8/2008 | Gerber et al. | | 2005/0222638 A1 | 10/2005 | Foley et al. |
| 7,447,545 B2 | 11/2008 | Heruth et al. | | 2005/0228455 A1 | 10/2005 | Kramer et al. |
| 7,471,290 B2 | 12/2008 | Wang et al. | | 2005/0234514 A1 | 10/2005 | Heruth et al. |
| 7,471,980 B2 | 12/2008 | Koshiol | | 2005/0234518 A1 | 10/2005 | Heruth et al. |
| 7,489,970 B2 | 2/2009 | Lee et al. | | 2005/0240242 A1 | 10/2005 | DiLorenzo |
| 7,491,181 B2 | 2/2009 | Heruth et al. | | 2005/0245988 A1 | 11/2005 | Miesel |
| 7,505,815 B2 | 3/2009 | Lee et al. | | 2005/0283210 A1 | 12/2005 | Blischak et al. |
| 7,519,431 B2 | 4/2009 | Goetz et al. | | 2006/0190049 A1 | 8/2006 | Gerber et al. |
| 7,542,803 B2 | 6/2009 | Heruth et al. | | 2006/0190050 A1 | 8/2006 | Gerber et al. |
| 7,548,786 B2 | 6/2009 | Lee et al. | | 2006/0190051 A1 | 8/2006 | Gerber et al. |
| 7,559,901 B2 | 7/2009 | Maile | | 2006/0195051 A1 | 8/2006 | Schnapp et al. |
| 7,572,225 B2 | 8/2009 | Stahmann | | 2006/0206167 A1 | 9/2006 | Flaherty et al. |
| 7,577,479 B2 | 8/2009 | Hartley et al. | | 2006/0212080 A1 | 9/2006 | Hartley et al. |
| 7,580,752 B2 | 8/2009 | Gerber et al. | | 2006/0213267 A1 | 9/2006 | Tronconi et al. |
| 7,584,808 B2 | 9/2009 | Dolgin et al. | | 2006/0235289 A1 | 10/2006 | Wesselink et al. |
| 7,590,453 B2 | 9/2009 | Heruth | | 2006/0235472 A1 | 10/2006 | Goetz et al. |
| 7,590,455 B2 | 9/2009 | Heruth et al. | | 2006/0241513 A1 | 10/2006 | Hatlestad et al. |
| 7,590,481 B2 | 9/2009 | Lu et al. | | 2006/0247732 A1 | 11/2006 | Wesselink |
| 7,591,265 B2 | 9/2009 | Lee et al. | | 2006/0247739 A1 | 11/2006 | Wahlstrand et al. |
| 7,603,170 B2 | 10/2009 | Hatlestad et al. | | 2006/0253174 A1 * | 11/2006 | King .............................. 607/62 |
| 7,623,919 B2 | 11/2009 | Goetz et al. | | 2006/0259099 A1 | 11/2006 | Goetz et al. |
| 7,634,379 B2 | 12/2009 | Noble | | 2006/0262120 A1 | 11/2006 | Rosenberg |
| 7,664,546 B2 | 2/2010 | Hartley et al. | | 2006/0265025 A1 | 11/2006 | Goetz et al. |
| 7,672,806 B2 | 3/2010 | Tronconi | | 2006/0287686 A1 | 12/2006 | Cullen et al. |
| 7,717,848 B2 | 5/2010 | Heruth et al. | | 2007/0015976 A1 | 1/2007 | Miesel et al. |
| 7,769,464 B2 | 8/2010 | Gerber et al. | | 2007/0038265 A1 | 2/2007 | Tcheng et al. |
| 7,792,583 B2 | 9/2010 | Heruth et al. | | 2007/0050715 A1 | 3/2007 | Behar |
| 2002/0038137 A1 | 3/2002 | Stein | | 2007/0073355 A1 | 3/2007 | Dilorenzo et al. |
| 2002/0091308 A1 | 7/2002 | Kipshidze et al. | | 2007/0115277 A1 | 5/2007 | Wang et al. |
| 2002/0107553 A1 | 8/2002 | Hill et al. | | 2007/0118056 A1 | 5/2007 | Wang et al. |
| 2002/0115939 A1 | 8/2002 | Mulligan et al. | | 2007/0123758 A1 | 5/2007 | Miesel et al. |
| 2002/0165586 A1 | 11/2002 | Hill et al. | | 2007/0129622 A1 | 6/2007 | Bourget et al. |
| 2002/0169485 A1 | 11/2002 | Pless et al. | | 2007/0129641 A1 | 6/2007 | Sweeney |
| 2002/0170193 A1 | 11/2002 | Townsend et al. | | 2007/0129769 A1 | 6/2007 | Bourget et al. |
| 2003/0004423 A1 | 1/2003 | Lavie et al. | | 2007/0129774 A1 | 6/2007 | Bourget et al. |
| 2003/0036783 A1 | 2/2003 | Bauhahn et al. | | 2007/0150026 A1 | 6/2007 | Bourget et al. |
| 2003/0045910 A1 | 3/2003 | Sorensen et al. | | 2007/0150029 A1 | 6/2007 | Bourget et al. |
| 2003/0065370 A1 | 4/2003 | Lebel et al. | | 2007/0213789 A1 | 9/2007 | Nolan et al. |
| 2003/0088185 A1 | 5/2003 | Prass | | 2007/0249968 A1 | 10/2007 | Miesel et al. |
| 2003/0149457 A1 | 8/2003 | Tcheng et al. | | 2007/0250121 A1 | 10/2007 | Miesel et al. |
| 2003/0171791 A1 | 9/2003 | KenKnight et al. | | 2007/0250134 A1 | 10/2007 | Miesel et al. |
| 2003/0181960 A1 | 9/2003 | Carter et al. | | 2007/0255118 A1 | 11/2007 | Miesel et al. |
| 2003/0204211 A1 | 10/2003 | Condie et al. | | 2007/0255154 A1 | 11/2007 | Lu et al. |
| 2004/0015103 A1 | 1/2004 | Aminian et al. | | 2007/0265664 A1 | 11/2007 | Gerber et al. |
| 2004/0049132 A1 | 3/2004 | Barron et al. | | 2007/0265681 A1 | 11/2007 | Gerber et al. |
| 2004/0088020 A1 | 5/2004 | Condie et al. | | 2007/0276439 A1 | 11/2007 | Miesel et al. |
| 2004/0102814 A1 | 5/2004 | Sorensen et al. | | 2007/0293737 A1 | 12/2007 | Heruth et al. |
| 2004/0133248 A1 | 7/2004 | Frei et al. | | 2007/0293917 A1 | 12/2007 | Thompson |
| 2004/0138716 A1 | 7/2004 | Kon et al. | | 2008/0071150 A1 | 3/2008 | Miesel et al. |
| 2004/0147975 A1 | 7/2004 | Popovic et al. | | 2008/0071324 A1 | 3/2008 | Miesel et al. |
| 2004/0199215 A1 | 10/2004 | Lee et al. | | 2008/0071326 A1 | 3/2008 | Heruth et al. |
| 2004/0199216 A1 | 10/2004 | Lee et al. | | 2008/0071327 A1 | 3/2008 | Miesel et al. |
| 2004/0199217 A1 | 10/2004 | Lee et al. | | 2008/0079444 A1 | 4/2008 | Denison |
| 2004/0199218 A1 | 10/2004 | Lee et al. | | 2008/0081958 A1 | 4/2008 | Denison et al. |
| 2004/0215286 A1 | 10/2004 | Stypulkowski | | 2008/0114219 A1 | 5/2008 | Zhang et al. |
| 2004/0220621 A1 | 11/2004 | Zhou et al. | | 2008/0164979 A1 | 7/2008 | Otto |
| 2004/0225332 A1 | 11/2004 | Gebhardt et al. | | 2008/0177355 A1 | 7/2008 | Miesel et al. |
| 2004/0257693 A1 | 12/2004 | Ehrlich | | 2008/0188901 A1 | 8/2008 | Sanghera et al. |
| 2005/0042589 A1 | 2/2005 | Hatlestad et al. | | 2008/0188909 A1 | 8/2008 | Bradley |
| 2005/0043767 A1 | 2/2005 | Belalcazar | | 2008/0194998 A1 | 8/2008 | Holmstrom et al. |
| 2005/0060001 A1 | 3/2005 | Singhal et al. | | 2008/0204255 A1 | 8/2008 | Flexer et al. |
| 2005/0061320 A1 | 3/2005 | Lee et al. | | 2008/0269812 A1 | 10/2008 | Gerber et al. |
| 2005/0113710 A1 | 5/2005 | Stahmann et al. | | 2008/0269843 A1 | 10/2008 | Gerber |
| 2005/0113887 A1 | 5/2005 | Bauhahn | | 2008/0281376 A1 | 11/2008 | Gerber et al. |
| 2005/0126026 A1 | 6/2005 | Townsend et al. | | 2008/0281379 A1 | 11/2008 | Wesselink |
| 2005/0137627 A1 | 6/2005 | Koshiol et al. | | 2008/0281381 A1 | 11/2008 | Gerber et al. |
| 2005/0145246 A1 | 7/2005 | Hartley et al. | | 2008/0288200 A1 | 11/2008 | Noble |
| 2005/0172311 A1 | 8/2005 | Hjelt et al. | | 2008/0300449 A1 | 12/2008 | Gerber et al. |
| 2005/0177192 A1 | 8/2005 | Rezai et al. | | 2008/0300470 A1 | 12/2008 | Gerber et al. |
| 2005/0209511 A1 | 9/2005 | Heruth et al. | | 2009/0030263 A1 | 1/2009 | Heruth et al. |
| 2005/0209512 A1 | 9/2005 | Heruth et al. | | 2009/0036951 A1 | 2/2009 | Heruth et al. |
| 2005/0209513 A1 | 9/2005 | Heruth et al. | | 2009/0046056 A1 | 2/2009 | Rosenberg et al. |
| 2005/0209643 A1 | 9/2005 | Heruth et al. | | 2009/0076343 A1 | 3/2009 | James et al. |

| | | | |
|---|---|---|---|
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| DE | 10024103 | 11/2001 |
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/0100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.

Goodrich et al., "The Prediction of Pain Using Measures of Sleep Quality," Pain Digest, 8:23-25, 1998.

Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006, 5 pp., http://eis.comp.lancs.ac.uk/fileadmin/relate/publication/2006-WearableSensors.pdf.

Hendelman et al., "Validity of Accelerometry for the Assessment of Moderate Intensity Physical Activity in the Field," Medicine & Science in Sports & Exercise, pp. S442-S449, 2000.

Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.

Husak, "Model of Tilt Sensor Systems, "ICECS 2002, $9^{th}$ IEEE International Conference on Electronics, Circuits and Systems, vol. 1, pp. 227-230, 2002.

Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.

Kassam, "2005 EDP Topic "MK4": Tremor Data-Logger for Parkinson's Disease Patients," http://www.ee.ryerson.ca/~courses/edp2005/MK4..html, 3 pp., 2005.

Kerr et al., "Analysis of the sit-stand-sit movement cycle in normal subjects," Clinical Biomechanics, vol. 12, No. 4, pp. 236-245, 1977.

Kiani et al., "Computerized Analysis of Daily Life Motor Activity for Ambulatory Monitoring," Technology and Health Care 5, pp. 307-318, 1997.

Kitchin et al., "Compensating for the 0 g Offset Drift of the ADXL50 Accelerometer," Analog Devices Application Note AN-380, 2 pp.

Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.

Leiper et al., "Sensory Feedback for Head Control in Cerebral Palsy," Physical Therapy, vol. 61, No. 4, pp. 512-518, Apr. 1981.

Lorussi, "Wearable, Redundant Fabric-Based Sensor Arrays for Reconstruction of Body Segment Posture," IEEE Sensors Journal, vol. 4, No. 6, pp. 808-817, Dec. 2004.

Mathie et al., "A Pilot Study of Long-Term Monitoring of Human Movements in the Home Using Accelerometer," Journal of Telemedicine and Telecare10:144-151, Jun. 2007.

Mathie et al., "Determining Activity Using a Triaxial Accelerometer," Proceedings of the Second Joint EMBS/BMES Conference, Houston, TX, pp. 2481-2482, Oct. 23-26, 2002.

Mattmann et al., "Recognizing Upper Body Postures Using Textile Strain Sensors," Proceedings Eleventh IEEE International Symposium on Wearable Computers, ISWC, pp. 29-36, 2007.

Mendez et al., "Interactions Between Sleep and Epilepsy," Journal of Clinical Neurophysiology, American Clinical Neurophysiology Society, 18(2), pp. 106-127, 2001.

Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.

Slyper et al., "Action Capture with Accelerometers," Eurographics/ACM SIGGRAPH Symposium on Computer Animation, Carnegie Mellon University, 7 pp., 2008.

"Analysis of heart rate dynamics by methods derived from non-linear mathematics: Clinical applicability and prognostic significance," http://herkules.oulu.fi.isbn9514250133/html, 4 pp., 2004.

"Design Competition: Runners-Up for the Best Three Designs," EPN, vol. 26, No. 1, 1 pg., 2002.

IBM and Citizen Watch develop Linux-Based "WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-51, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universitat Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

Smith et al., "How do sleep disturbance and chronic pain inter-relate? Insights from the longitudinal and cognitive-behavioral clinical trials literature," Sleep Medicine Reviews, YSMRV 286, pp. 1-14, 2003.

Smith et al., "Presleep cognitions in Patients with Insomnia Secondary to Chronic Pain," Journal of Behavioral Medicine, vol. 24, No. 1, pp. 93-114, 2001.

Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.

Trolier-Mckinstry et al., "Thin Film Piezoelectrics for MEMS," Journal of Electroceramics, v. 12, No. 1-2, pp. 7-17, Jan./Mar. 2004.

Tuck, "Implementing Auto-Zero Calibration Technique for Accelerometers," Freescale Semiconductor Application Note AN3447, 5 pp., Mar. 2007.

Tuisku, "Motor Activity Measured by Actometry in Neuropsychiatric Disorders," Department of Psychiatry, University of Helsinki, Helsinki, Finland, 115 pp., 2002.

Vega-Gonzalez, "Upper Limb Activity Monitoring," Arch Phys Med Rehabil, vol. 86, pp. 541-548, Mar. 2005.

Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.

PCT/US2009/049390, International Search Report and Written Opinion dated May 7, 2010, 14 pp.

U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

* cited by examiner

POSTURE-RESPONSIVE THERAPY CONTROL BASED ON PATIENT INPUT

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, spasticity, or gastroparesis. As an example, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each parameter in a set specified by a clinician.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure relates to posture-responsive therapy delivery. In examples described herein, a medical device detects a posture state of a patient and delivers therapy based at least in part on the detected patient posture state. For example, in some cases, the medical device adjusts one or more therapy parameter values or other characteristics of the therapy based on the detected posture state.

Various posture states may be defined and detected by a medical device, at least in part, by different sets of posture reference data. In some examples, a posture sensor module associated with the medical device compares posture data from one of multiple posture sensors to the posture reference data to detect the posture occupied by the patient. Some examples according to this disclosure include methods and systems in which patient efficacy inputs (e.g., patient provided efficacy ratings) are received over a period of time during which the patient occupies a variety of posture states and correlated with the times at which the inputs were received, sensed posture states of the patient, and therapy programs defining therapy delivery. In accordance with some examples, the temporally correlated patient efficacy inputs, sensed posture states, and therapy programs are presented to a user (e.g., the patient or clinician) as a function of time. A therapy program that defines subsequent posture-responsive therapy delivery to the patient is adjusted based on one or more of the correlations between patient input, patient input time, sensed posture state, and therapy program.

In one example, a method is disclosed that includes receiving a plurality of inputs from a patient indicative of an efficacy of therapy delivered to the patient by a medical device over a period of time. Each of the patient inputs are correlated to a time at which the input was received, a sensed posture state of the patient at the time the patient input was received, and a therapy program defining therapy delivery at the time the patient input was received. The patient inputs and correlated sensed posture states, therapy programs, and patient input times are presented as a function of time to a user. A subsequent therapy program to be delivered while the patient is in a subsequent posture state at a subsequent time is adjusted based on one or more of the correlations between patient input, patient input time, sensed posture state, and therapy program.

In another example, a computer-readable medium is disclosed that includes instructions for causing a programmable processor to carry out a method. The method includes receiving a plurality of inputs from a patient indicative of an efficacy of therapy delivered to the patient by a medical device over a period of time. Each of the patient inputs are correlated to a time at which the input was received, a sensed posture state of the patient at the time the patient input was received, and a therapy program defining therapy delivery at the time the patient input was received. The patient inputs and correlated sensed posture states, therapy programs, and patient input times are presented as a function of time to a user. A subsequent therapy program to be delivered while the patient is in a subsequent posture state at a subsequent time is adjusted based on one or more of the correlations between patient input, patient input time, sensed posture state, and therapy program.

In an additional example, an implantable medical system configured to deliver posture-responsive therapy to a patient is disclosed. The system includes an implantable medical device ("IMD") that senses patient posture states and delivers therapy to the patient by adjusting one or more therapy parameter values based on a sensed posture state of the patient. A processor is communicatively connected to the IMD. The processor receives a plurality of inputs from a patient indicative of an efficacy of therapy delivered to the patient by the IMD over a period of time, and correlates each of the patient inputs to a time at which the input was received, a sensed posture state of the patient at the time the patient input was received, and a therapy program defining therapy delivery at the time the patient input was received. The processor presents the patient inputs and correlated sensed posture states, therapy programs, and patient input times as a function of time to a user, and adjusts a subsequent therapy program to be delivered while the patient is in a subsequent posture state at a subsequent time based on one or more of the correlations between patient input, patient input time, sensed posture state, and therapy program.

In another example, the disclosure is directed to a computer-readable storage medium comprising instructions. The instructions cause a programmable processor to perform any of the techniques described herein. The instructions may be encoded in the computer-readable medium. The instructions may be, for example, software instructions, such as those used to define a software or computer program. The computer-readable medium may be a computer-storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more aspects of the disclosure are set forth in the accompanying drawings and the description below. Other features, objects, and advantages will be apparent from the description and drawings, and from the claims.

DETAILED DESCRIPTION

Figure 1A:
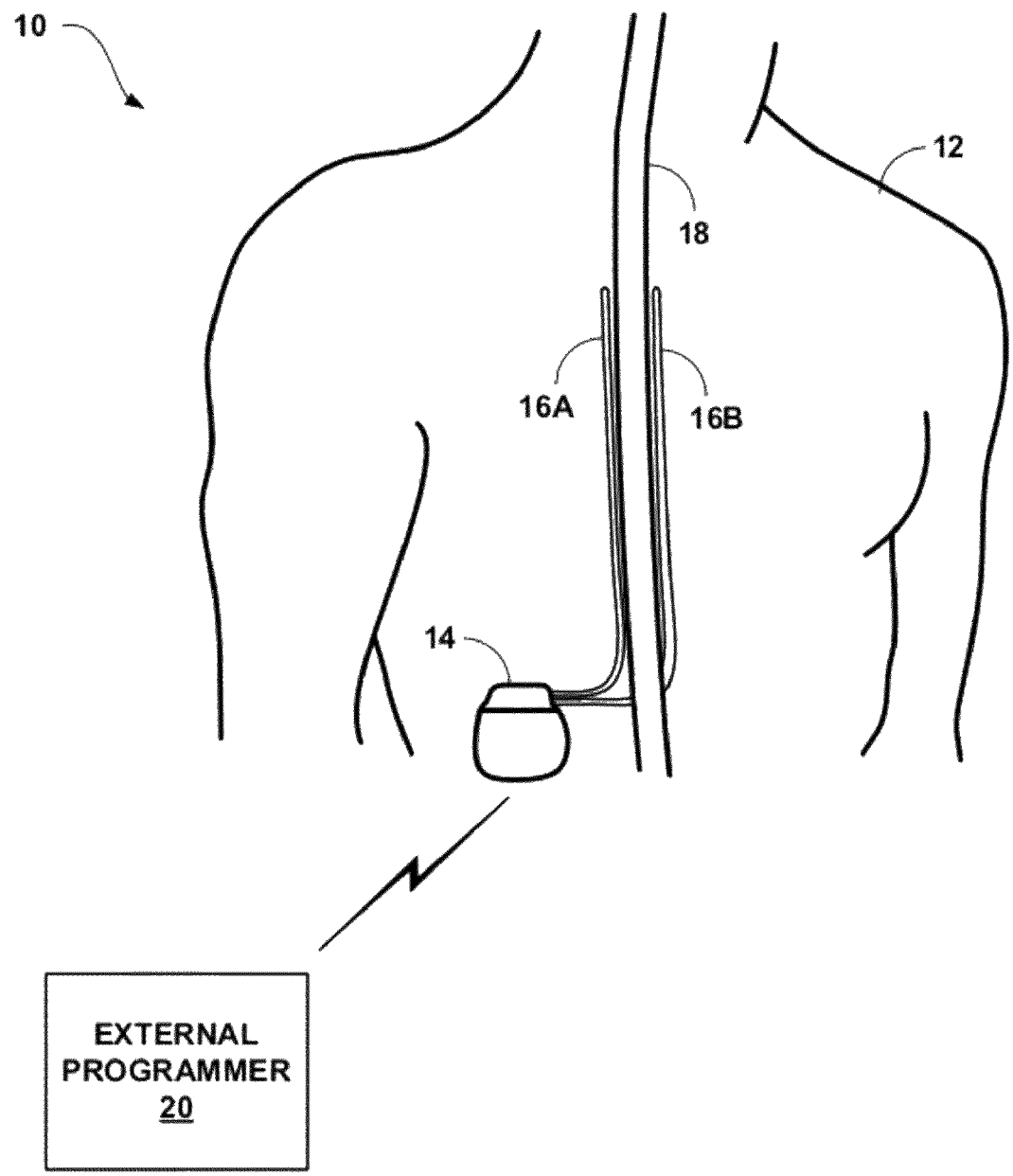
FIG. 1A is a conceptual diagram illustrating an implantable stimulation system including two implantable stimulation leads.

In some medical devices that deliver electrical stimulation therapy or a therapeutic agent to a patient to manage one or more patient conditions, therapeutic efficacy may change as the patient changes posture states. Efficacy refers, in general, to a combination of complete or partial alleviation of symptoms alone, or in combination with a degree of undesirable side effects. In general, a posture state refers to a patient posture or a combination of posture and activity. For example, some posture states, such as upright, may be sub-categorized as upright and active or upright and inactive. Other posture states, such as lying down posture states, may or may not have an activity component, but regardless may have sub-categories such as lying face up or face down, or lying on the right side or on the left side.

Changes in posture state may cause changes in efficacy due to changes in distances between electrodes or other therapy delivery elements, e.g., due to temporary migration of leads or catheters caused by forces or stresses associated with different postures, or from changes in compression of patient tissue against leads or catheters in different posture states. Also, posture state changes may present changes in symptoms or symptom levels, e.g., pain level. For example, for some patients with a chronic lower back condition, sitting may be more painful than lying down. To maintain therapeutic efficacy, it may be desirable to adjust therapy parameters based on different postures and/or activities engaged by the patient to maintain effective therapy. A medical device may adjust therapy by modifying values for one or more therapy parameters, e.g., by specifying adjustments to a specific therapy parameter or by selecting different therapy programs or groups of programs that define different sets of therapy parameter values.

A change in efficacy due to changes in posture state may require the patient to continually manage therapy by manually adjusting certain therapy parameters, such as amplitude, pulse rate, or pulse width in the case of stimulation therapy, or selecting different therapy programs to achieve more efficacious therapy throughout many different posture states. In examples of therapy systems described herein, a medical device employs one or more posture sensors, each of which may generate a signal indicative of the patient posture state. The medical system adjusts therapy parameters in response to a detected posture states, e.g., by modifying one or more specific therapy parameter values or selecting one or more therapy programs from memory based on the detected posture state. Therapy adjustments in response to different posture states may be fully automatic, semi-automatic in the sense that a user may provide approval of proposed changes, user-directed in the sense that the patient may manually adjust therapy based on the posture state indication, or any combination of automation and user interaction.

In accordance with techniques described in this disclosure, a posture-responsive medical device receives patient efficacy inputs over a period of time during which the patient occupies a variety of posture states and presents the patient inputs correlated with the times at which the inputs were received, sensed posture states of the patient (e.g., the posture state determined at the time at each of the times the patient inputs were received), and therapy programs defining therapy delivery (e.g., the therapy programs defining the therapy delivered by the medical device at each of the times the patient inputs were received) as a function of time to a user. In some examples, a posture state correlated to patient input may be the posture state sensed at the time at which the patient input was received. However, in other examples, the posture state correlated to patient input may be the posture state sensed at a time other than the time the patient input was received, e.g., a posture state sensed before the patient input was received.

The efficacy inputs can be, for example, a subjective rating of the efficacy of therapy provided to the patient, e.g., on a numerical scale, alphanumeric scale, scale presented by graphical indicators (e.g., the Wong-Baker faces pain rating scale), and the like. In some examples, the patient efficacy inputs indicate a rating of how therapy delivery according to a particular set of therapy parameter values is alleviating symptoms of the patient condition, a rating of the side effects, or a combination thereof. The patient efficacy input is distinct from a patient-initiated modification to a therapy parameter value. The patient efficacy input may be made in addition to a patient modification to a therapy parameter value.

After correlating patient inputs to input times, sensed posture states, and therapy programs, a therapy program defining subsequent posture responsive therapy delivered to the patient is then adjusted based on one or more of the correlations. The correlations between patient input, patient input time, sensed posture state, and therapy program may be referred to as therapy information. Although described as associated with a therapy program as a whole, patient efficacy inputs may also be received for one or more individual parameters within a therapy program. For example, the patient may provide inputs about the level of efficacy of the electrical stimulation amplitude or therapeutic fluid dose defined by a therapy program.

Any suitable format may be used to present the therapy information. In one example, the patient inputs and correlated sensed posture states, therapy programs, and patient input times are presented as a step function graph. In examples including a step function presentation, the step function graph may include a first step function plot of patient posture states as a function of time and a second step function plot of therapy programs as a function of time. In one example including the first and second step function plots, the patient efficacy inputs are represented by substantially vertical lines connecting a patient posture state on the first step function plot to a therapy program on the second step function plot at a time at which the patient input was received, the posture state of the patient was sensed, and therapy defined by the therapy program was delivered. In one example, each of the patient efficacy input vertical lines on the step function plots is annotated with a symbol indicative of one of a range of efficacy levels. The range of efficacy levels may include, e.g., more than two levels indicated by a set of sequential symbols. In one such example, the set of sequential symbols includes one of a set of sequential alphanumeric indicators (e.g., numbers or letters). In another example, the range of efficacy levels includes a satisfactory level and a spectrum of levels above and below the satisfactory level.

Adjusting subsequent therapy programs (e.g., therapy programs that define subsequent therapy delivery to the patient) based on one or more of the correlations between patient input, patient input time, sensed posture state, and therapy program may be accomplished using any suitable techniques. For example, a subsequent therapy program associated with a particular posture state may include the therapy parameter values of a therapy program correlated to a patient input with a highest level of efficacy for the particular posture state relative to the other therapy programs that may be associated with the particular posture state. In another example, the subsequent therapy program associated with a particular posture state includes the one or more therapy parameter values of a therapy program correlated to a patient input with a highest level of efficacy for all the posture states that were correlated to patient inputs and therapy programs.

In still another example, a subsequent therapy program associated with a particular posture state includes the one or more therapy parameter values of a therapy program correlated to a patient input with a highest level of efficacy for a specific patient input time. The specific patient input time can be selected to be similar to the subsequent time at which the subsequent therapy program is to be delivered. In one such example, the subsequent time is the same time of day as the time at which the patient efficacy input with the highest level of efficacy was received. For example, the patient may set the therapy program that defines therapy delivered at 8:00 a.m. to be the same therapy program previously received at 8:00 a.m. (e.g., received on a previous day) because the previous therapy received at 8:00 a.m. on the previous morning(s) was particularly efficacious in relieving the patient's symptoms.

In addition to adjusting one subsequent therapy program based on the highest level of patient efficacy input for a particular posture state, for all posture states, or for a particular patient input time, multiple subsequent therapy programs may be adjusted for one or more posture states based on a single correlation between patient input, patient input time, sensed posture state, and therapy program. In one example, a plurality of subsequent therapy programs that define therapy delivery to the patient while the patient is in a particular posture state at a plurality of subsequent times is adjusted based on one correlation between a patient efficacy input, patient input time, sensed posture state, and therapy program. In another example, a plurality of subsequent therapy programs while the patient is in a plurality of subsequent posture states at a plurality of subsequent times is adjusted based on one correlation between a patient input, patient input time, sensed posture state, and therapy program. In this manner, the patient may adjust therapy delivery for one more posture states based on a single historical correlation between patient input, patient input time, sensed posture state, and therapy program.

A patient, patient caretaker or another user may adjust one or more therapy programs for subsequent therapy delivery using, e.g., an external programmer. For example, the patient can provide a selection input that indicates that one subsequent therapy program should be set to one of the therapy programs correlated to patient input, patient input time, and sensed posture state. In another example, subsequent programs are adjusted by receiving a selection input from the user indicating that a plurality of subsequent therapy programs should be set to one of the therapy programs correlated to patient input, patient input time, and sensed posture state.

FIG. 1A is a schematic diagram illustrating an implantable stimulation system 10 including a pair of implantable electrode arrays in the form of stimulation leads 16A and 16B. Although the techniques described in this disclosure are generally applicable to a variety of medical devices including external and implantable medical devices (IMDs), application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1A, system 10 includes an IMD 14, stimulation leads 16A and 16B, and external programmer 20, all of which are shown in conjunction with patient 12. In the example of FIG. 1A, IMD 14 is an implantable electrical stimulator configured for SCS, e.g., for relief of chronic pain or other symptoms. IMD 14 is implanted within patient 12, and may be, for example, positioned within subcutaneous or submuscular tissue. Stimulation leads 16A and 16B are connected to IMD 14 and tunneled through tissue of patient 12 to a therapy delivery site proximate spinal cord 18. Patient 12 is ordinarily a human patient, but may also be a non-human patient including, e.g., a primate, canine, equine, pig, and feline.

IMD 14, in general, has an outer housing that is constructed of a biocompatible material that resists corrosion and degradation from bodily fluids including, e.g., titanium or stainless steel, or a polymeric material including silicone, polyurethane, or other biologically inert polymers. IMD 14 may be implanted within a subcutaneous pocket close to the therapy delivery site. For example, in the example shown in FIG. 1, IMD 14 is implanted within the abdomen of patient 12. However, for SCS, IMD 14 may also be located in the lower back, upper buttocks, or other location to secure IMD 14. In other examples, IMD 14 may be implanted within other suitable sites within patient 12, which may depend, for example, on the target site within patient 12 for the delivery of electrical stimulation therapy. In still other examples, IMD 14 may be external to patient 12 with percutaneous implantable leads connected between IMD 14 and the target delivery site within patient 12.

Stimulation energy is delivered from IMD 14 to spinal cord 18 of patient 12 via one or more electrodes of implantable leads 16A and 16B (collectively "leads 16"). The electrodes (not shown) may be, e.g., electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In some applications, such as SCS to treat chronic pain, the adjacent implantable leads 16 may have longitudinal axes that are substantially parallel to one another.

The therapy parameters for a therapy program that controls delivery of stimulation therapy by IMD 14 through the electrodes of leads 16 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as dosage amount, rate, or the like in the case IMD 14 is also configured for drug delivery.

In the example of FIG. 1A, leads 16 carry electrodes that are placed adjacent to the target tissue of spinal cord 18. One or more of the electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation that is used on a temporary basis to evaluate potential efficacy to aid in consideration of chronic implantation for a patient. In additional embodiments, IMD 14 may be a leadless stimulator with one or more arrays of electrodes arranged on a housing of the stimulator rather than leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or continuous waveforms. In some examples, the target tissue includes nerves, smooth muscle or skeletal muscle.

In the example illustrated by FIG. 1A, the target tissue is tissue proximate spinal cord 18, such as within an intrathecal space or epidural space of spinal cord 18, or, in some examples, adjacent nerves that branch off of spinal cord 18. Leads 16 may be introduced into spinal cord 18 via any suitable region, such as the thoracic, cervical or lumbar regions. Stimulation of spinal cord 18 may, for example, prevent pain signals from traveling through spinal cord 18 and to the brain of patient 12. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), peripheral nerve stimulation (PNS), peripheral nerve field stimulation (PNFS), cortical stimulation (CS), pelvic floor stimulation, gastric stimulation, or any other stimulation therapy capable of treating a condition of patient 12. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

As mentioned above, IMD 14 generates and delivers stimulation therapy to a target stimulation site within patient 12 via the electrodes of leads 16 to patient 12 according to one or more therapy programs, which may also be referred to as a set of therapy parameter values. A therapy program defines values for one or more parameters that define an aspect of the therapy delivered by IMD 14 according to that program. For example, a program that controls delivery of stimulation by IMD 14 in the form of pulses may define values for voltage or current pulse amplitude, pulse width, and pulse rate for stimulation pulses delivered by IMD 14 according to that program. Moreover, therapy may be delivered according to multiple programs, wherein multiple programs are contained within each of a multiple of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, leads 16 may migrate toward IMD 14 when patient 12 bends at the waist, resulting in displacement of electrodes and possible disruption in delivery of effective therapy. Stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may need to be decreased to avoid causing patient 12 additional pain or unusual sensations, which may be considered undesirable side effects that undermine overall efficacy. Also, posture state changes may present changes in symptoms or symptom levels including, e.g., pain level.

Therapy system 10 includes a posture state module that determines a patient posture and modifies therapy deliver to patient 12 based on the determined patient posture. In this way, the posture state module helps delivery posture-responsive therapy, which helps to minimize interruptions in effective therapy delivery that may ordinarily result from changes in the patient posture state. In the examples described herein, IMD 14 includes the posture state module. However, in other examples, programmer 20 or another device may include the posture state module and control IMD 14 based on a determined posture state.

IMD 14 including the posture state module automatically adjusts stimulation according to the detected posture state to improve therapy efficacy across multiple posture states. For example, the posture state module may receive input from one or more accelerometers each of which generates a signal with which IMD 14 determines when patient 12 occupies a posture state in which it is appropriate to change the stimulation therapy. Examples of modifications to stimulation therapy that may be made in response to detecting a change in patient posture state include, but are not limited to, changes in stimulation amplitude. For example, IMD 14 may decrease the stimulation amplitude when the posture state module indicates that patient 12 has lain down. IMD 14 may automatically reduce stimulation amplitude so that patient 12 does not have to do so manually. In addition to "Lying Down," example posture states include "Upright," "Sitting," and so forth. Additionally, one or more of the posture states may have sub-categories including, e.g., "Upright and Active," "Lying Face Down," "Lying Face Up," and so forth.

IMD 14 may be configured to automatically decrease amplitude at a rate suitable to prevent undesirable effects, e.g., such as the effects due to the compression of leads 16 towards spinal cord 18 when patient lies down. In some examples, IMD 14 is configured to decrease the stimulation amplitude to a suitable amplitude value substantially immediately upon detection by IMD 14 that patient 12 is lying down. In other examples, IMD 14 gradually decreases the stimulation amplitude to a suitable amplitude level at a rate of change that is suitable to prevent patient 12 from experiencing undesirable stimulation effects, e.g., due to increased transfer of stimulation energy from, e.g., compression of leads 16 towards spinal cord 18 when patient 12 lies down. In either example, IMD 14 automatically reduces stimulation amplitude upon determining patient 12 has transitioned to a lying down posture state so that patient 12 does not need to manually reduce the stimulation amplitude.

In response to a posture state indication by the posture state module, IMD 14 modifies therapy, e.g., by changing therapy program groups, therapy programs, modifying a stimulation amplitude, pulse width, pulse rate, and/or one or more other parameters, to maintain therapeutic efficacy, as in the above described example of the patient lying down. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

Referring still to FIG. 1A, a user, such as a clinician or patient 12, may interact with a user interface of external programmer 20 to program or otherwise interact with IMD 14. Programming of IMD 14 may refer generally to the generation and transfer of commands, programs, or other information to control the operation of IMD 14. For example, external programmer 20 may transmit programs, parameter adjustments, program selections, group selections, patient efficacy inputs, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

In some cases, external programmer 20 may be characterized as a clinician (or physician) programmer if it is primarily intended for use by a clinician. In other cases, external programmer 20 may be characterized as a patient programmer if it is primarily intended for use by a patient. A patient programmer is generally accessible to patient 12 and, in many cases, is a portable device that may accompany the patient throughout the patient's daily routine. In general, a clinician programmer may support selection and generation of programs by a clinician for use by IMD 14, whereas a patient programmer may support adjustment and selection of such programs by a patient during ordinary use.

External programmer 20 may present posture state data stored in IMD 14 from the detected posture states of patient 12. The posture state data may be acquired by external programmer 20 to generate posture state information, e.g., therapy adjustment information. IMD 14 may also store any associations between the therapy adjustments input by patient 12 and the posture states for which the therapy adjustments were intended during, e.g., a record mode, i.e., therapy adjustment information. By recording all therapy adjustments made for a program in each of the posture states, external programmer 20 may present therapy adjustment information to the user that indicates stimulation parameters desired by patient 12. For example, the user may identify the most recent stimulation parameters desired by patient 12, the minimum and maximum allowable amplitudes, or even the quantified number of therapy adjustments to indicate that patient 12 is either satisfied with a program or cannot find suitable parameters for a program with many therapy adjustments.

In addition to transmitting parameter adjustments and selecting different therapy programs, external programmer 20 may be used to transmit patient inputs to IMD 14 that indicate a level of efficacy of the therapy delivered to patient 12 over a period of time during which patient 12 is in a variety of posture states. As described in further detail with respect to FIG. 12, programmer 20 or another external device may receive efficacy inputs from patient 12 and associate the inputs with respective therapy programs implemented by IMD 14, e.g., the therapy program implemented by IMD 14 at the time the patient efficacy input was received. Although patient efficacy inputs are described as associated with a therapy program as a whole, the inputs may also be received for one or more individual parameters within a therapy program. Patient 12 may provide inputs using external programmer 20 that indicate the level of efficacy of one parameter defined by a therapy program or the program as a whole. In either case, programmer 20 may then transmit the patient inputs to IMD 14, e.g., using telemetry circuitry as described with reference to FIG. 4.

A patient efficacy input and a patient-initiated modification to a therapy parameter value are different types of inputs that may be provided by patient 12. An efficacy input provides a subjective assessment of the therapy delivery by IMD 14 according to a particular therapy program or a specific therapy parameter value. The efficacy input may not result in a direct adjustment to one or more therapy parameter values as in the case of a patient-initiated modification to a therapy parameter value.

After receiving the patient efficacy inputs from programmer 20, or through some other means or device, IMD 14 correlates each of the patient inputs to a time at which the input was received, a sensed posture state of patient 12 at the time the patient input was received, and a therapy program defining therapy delivery at the time the patient input was received. In some examples, however, patient 12 may apply the efficacy input to other times, sensed posture states, and therapy programs, such as in situations in which patient 12 provides the efficacy input after the time at which the posture state of patient 12 for which the efficacy input applies was sensed or after the time at which IMD 14 implemented the therapy program for which the efficacy input is relevant.

In one example, IMD 14 provides posture-responsive therapy by determining the posture state of patient 12 and delivering therapy defined by a therapy program that IMD 14 has associated with the sensed posture state of patient 12. Patient 12 then provides efficacy inputs for the therapy program using external programmer 20. IMD 14 time stamps the patient inputs and correlates the input with the input time, the sensed posture state, and the therapy program. IMD 14 may, for example, store the patient inputs, time, posture state, and therapy program in one or more non-volatile memories on IMD 14 or another device including, e.g., external programmer 20. The data may be stored in a database, table, list or other organized aggregation of the data that correlates the patient inputs to the input times, posture states, and therapy programs.

Although correlating patient efficacy inputs with input times, posture, and therapy programs has been described as executed by IMD 14, in other examples the correlations may be carried out by other devices including, e.g., external programmer 20. For example, the sensed posture state and therapy program data may be stored on and controlled by IMD 14. Upon receiving an efficacy input from patient 12, programmer 20 may time stamp the input and interrogate IMD 14 to determine the sensed posture state of patient 12 and the therapy program currently defining therapy delivered to the patient. For example, programmer 20 may command IMD 14 to transmit to programmer 20 the sensed posture state of patient 12 and the therapy program currently defining therapy delivered to the patient. Programmer 20 may then correlate the patient input with the input time, the sensed posture state, and the therapy program.

After a plurality of patient inputs has been correlated to input times, postures, and therapy programs, external programmer 20 may also present the correlated data as a function of time to a user. As described in greater detail with reference to FIG. 13, in one example, the patient inputs and correlated patient input times, posture states, and therapy programs are presented via a user interface of external programmer 20 as a step function graph. The step function graph presented on a display of programmer 20 may include a first step function plot of patient posture states as a function of time and a second step function plot of therapy programs as a function of time. The patient efficacy inputs may be represented by substantially vertical lines connecting a patient posture state on the first step function plot to a therapy program on the second step function plot at a time at which the patient input was received, the posture state of the patient was sensed, and therapy defined by the therapy program was delivered. Each of the patient efficacy input vertical lines on the step function plots may be further annotated with a symbol indicative of one of a range of efficacy levels. The range of efficacy levels may include, e.g., more than two levels indicated by a set of sequential symbols. In one such example, the set of sequential symbols includes a set of sequential alphanumeric indicators (e.g., a set of sequential numbers or a set of sequential letters). In another example, the range of efficacy levels includes a satisfactory level and a spectrum of levels above and below the satisfactory level.

In some examples, programmer 20 may further divided the step function plot of therapy programs into multiple plots related to sets of therapy programs directed at treating, e.g., different conditions or areas of pain. In one such example, programmer 20 may present a first step function plot of therapy programs for treating back pain as a function of time and a second step function plot of therapy programs for treating leg pain as a function of time. In this manner, program selection or program parameter selection/adjustment may be improved based on the patient efficacy inputs for multiple conditions and/or areas of pain.

External programmer 20 and/or IMD 14 may adjust a subsequent therapy program to be delivered while patient 12 is in a subsequent posture state at a subsequent time based on one or more of the correlations between patient input, patient input time, sensed posture state, and therapy program. In this way, subsequent therapy delivery to patient 12 can be adjusted based on historical therapy information relating to actual therapy efficacy inputs from patient 12.

In one example, IMD 14 automatically adjusts one or more stored therapy programs that are associated with patient posture states based on the correlations between patient input, patient input time, sensed posture state, and therapy program. For example, patient 12 may receive therapy from IMD 14 based on many different therapy programs associated with different postures over a period of time. During the period, patient 12 may receive therapy defined by multiple programs for a single posture state, e.g., lying down. Using external programmer 20, patient 12 may provide efficacy inputs, e.g., that are transmitted to IMD 14, that indicate the efficacy of the various therapy programs that define therapy delivered to patient 12 in the lying down state at different times. IMD 14 may then deliver therapy to patient 12 at a subsequent time when patient 12 is in the lying down posture states by selecting one of the previous therapy programs based on the efficacy inputs received from patient 12. For example, IMD 14 may select the therapy program associated the highest efficacy input rating to define all subsequent therapy delivered to patient 12 in the lying down posture state.

In another example of adjusting subsequent posture responsive therapy delivered to patient 12, a user may prescribe subsequent adjustments made by IMD 14 using external programmer 20. For example, external programmer 20 may present the patient efficacy inputs and correlated sensed posture states, therapy programs, and patient input times via a user interface of external programmer 20 as a step function graph. Patient 12 may then select one of the therapy programs that defined therapy delivered to patient 12 based on the correlations. For example, while reviewing the correlated therapy information, patient 12 may select the therapy program with the highest level of efficacy input for the upright posture state of patient 12.

Patient 12 may provide selection inputs using any suitable technique. For example, patient 12 may provide a selection input by, e.g., pressing a button on, tapping a screen of, or otherwise interacting with external programmer 20. Patient 12 may make selections directly on the step function graph or on another organized aggregation of data representing the patient inputs and correlated sensed posture states, therapy programs, and patient input times including, e.g., a list or table. Once patient 12 selects the desired therapy program based on patient efficacy input, patient 12 may use external programmer 20 to apply the selected program to subsequent therapy to be delivered to patient 12 at a subsequent time. For example, patient 12 applies the therapy program with the highest level of efficacy for the upright posture to define all subsequent therapy delivered to patient 12 in the upright posture state.

IMD 14 may apply a therapy adjustment determined based on the historical therapy information to one or more posture states and at one or more subsequent times. In one example, IMD 14 applies a therapy program correlated to a patient input with a highest level of efficacy for a posture state to subsequent detections of the posture state, i.e., the subsequent posture state. For example, IMD 14 can set a subsequent therapy program for the lying down posture to the previously delivered therapy program that is correlated with a patient input with the highest level of efficacy for the lying down posture state. In another example, IMD 14 applies a therapy program correlated to a patient input with a highest level of efficacy for all the posture states correlated to patient inputs and therapy programs, rather than the highest level of efficacy for a particular posture state.

In still another example, IMD 14 selects a therapy program for a particular posture state based on the therapy program that is correlated to a patient input with a highest level of efficacy for a specific patient input time. In one example, the specific patient input time is the same time of day as the time at which the patient efficacy input with the highest level of efficacy was received. For example, patient 12 may set the therapy program that defines therapy delivered at 8:00 a.m. to be the same therapy program previously received at 8:00 a.m. (e.g., received on a previous day) because the previous therapy received at 8:00 a.m. on the previous morning(s) was particularly efficacious in relieving the symptoms of patient 12.

In addition to adjusting one subsequent therapy program based on the therapy program associated with the highest level of patient efficacy input for a particular posture state, for all posture states, or for a particular patient input time, IMD 14 may adjust multiple therapy programs associated with one or more posture states based on a single correlation between patient input, patient input time, sensed posture state, and therapy program. In one example, IMD 14 adjusts a plurality of subsequent therapy programs associated with a particular posture state based on one correlation between a patient input, patient input time, sensed posture state, and therapy program. For example, IMD 14 can set all future therapy programs for the lying down posture state to the therapy program that received a patient input with the highest level of efficacy for the lying down posture state. Alternatively, IMD 14 can set all future therapy programs for the lying down posture state to the therapy program that received a patient input with the highest level of efficacy for all the posture states of patient 12, rather than just the lying down posture state.

In another example, a plurality of subsequent therapy programs associated with a respective one of a plurality of subsequent posture states are adjusted based on one correlation between a patient input, patient input time, sensed posture state, and therapy program. For example, IMD 14 can set all future therapy programs for the lying down and upright posture states to the therapy program that received a patient input with the highest level of efficacy for all the posture states of patient 12. In this manner, IMD 14 may adjust therapy delivered in one more posture states in the future based on a single historical correlation between patient input, patient input time, sensed posture state, and therapy program.

IMD 14, either automatically or through instruction from external programmer 20, may use criteria other than highest efficacy level to adjust subsequent therapy programs. For example, IMD 14 may select the therapy program for subsequent therapy delivery to patient 12 with the highest level of efficacy for a particular time of day, day of the week, or other type of time period. In another example, IMD 14 may use various averaging or other statistical techniques to combine parameters from various therapy programs that received inputs with the same level of efficacy from patient 12.

Figure 1B:
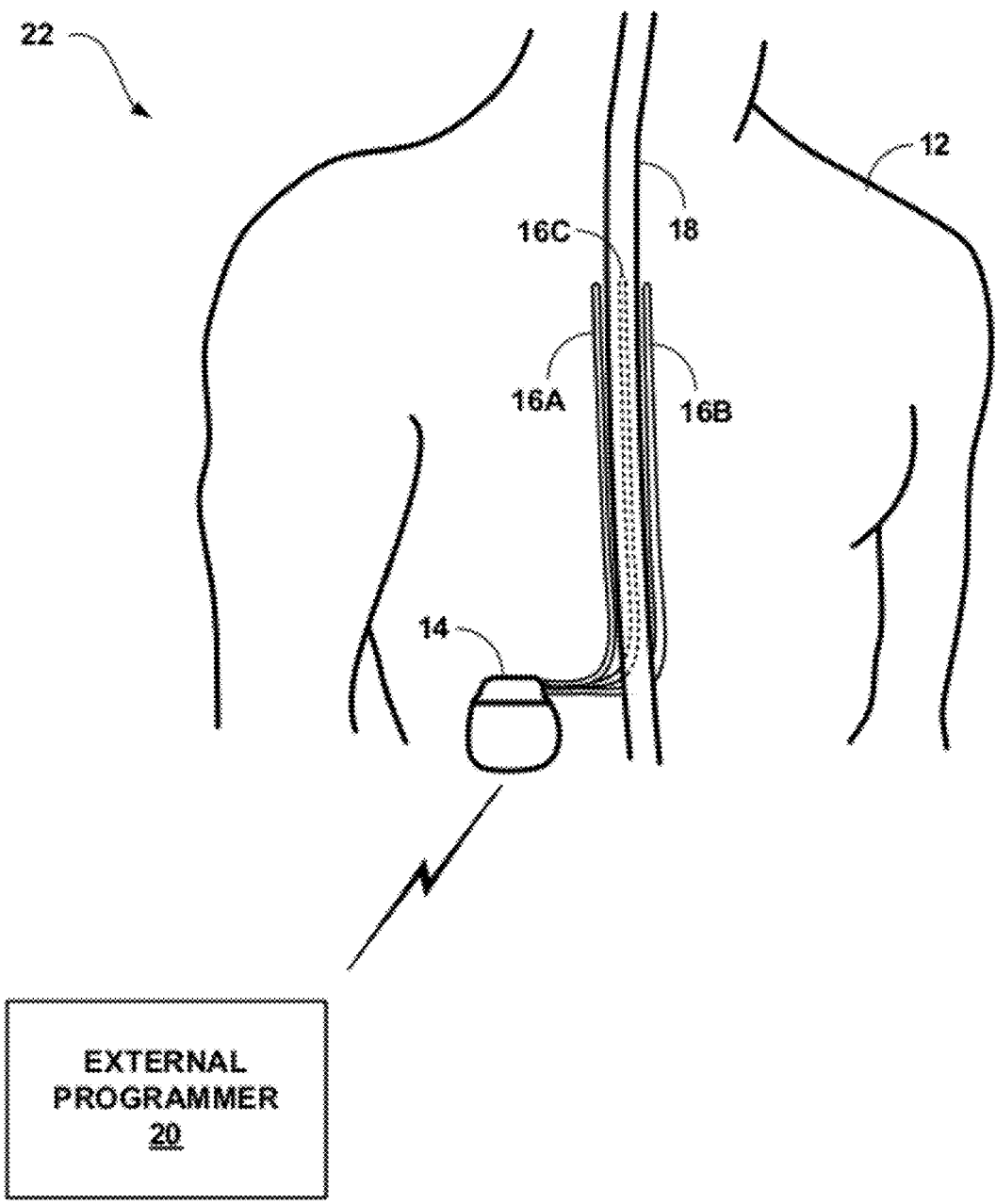
FIG. 1B is a conceptual diagram illustrating an implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. In some examples, the third lead 16C includes a greater number of electrodes than leads 16A and 16B and be positioned between leads 16A and 16B or on one side of either lead 16A or 16B.

For example, leads 16A and 16B could include four electrodes, while lead 16C includes eight or sixteen electrodes, thereby forming a so-called 4-8-4 or 4-16-4 lead configuration, whereby the numbers indicate the number of electrodes in a particular column, which can be defined by a single lead. Other lead configurations, such as 8-16-8, 8-4-8, 16-8-16, 16-4-16, are also possible. In some cases, electrodes on lead 16C may be smaller in size and/or closer together than the electrodes of leads 16A or 16B. External programmer 20 may be initially told the number and configuration of leads 16 in order to appropriately program stimulation therapy.

Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22. Additionally, IMD 14 may receive efficacy inputs from patient 12, e.g., via external programmer 20 over a period of time during which patient 12 occupies variety of posture states and present the inputs correlated with the times at which the inputs were received, sensed posture states of the patient at each of the times the patient inputs were received, and therapy programs defining therapy delivery at each of the times the patient inputs were received as a function of time to a user. IMD 14, either automatically or through instruction from external programmer 20 may then adjust a subsequent therapy program to be delivered while patient 12 is in a subsequent posture state at a subsequent time based on one or more of the correlations between patient input, patient input time, sensed posture state, and therapy program.

Figure 1C:
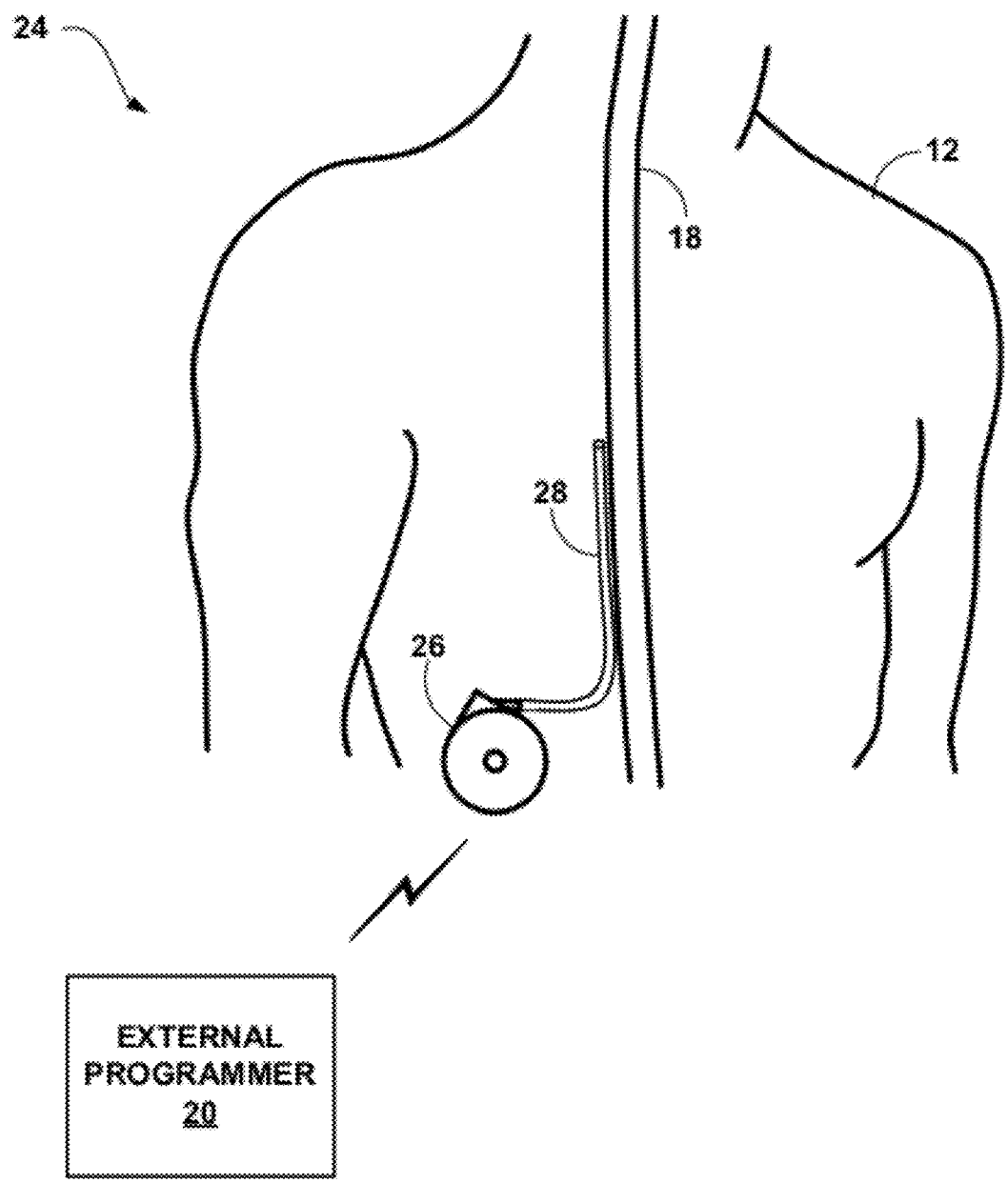
FIG. 1C is a conceptual diagram illustrating an implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of drug stimulation therapy instead of electrical stimulation therapy, i.e. delivering a therapeutic agent through catheter 28 to patient 12. Example therapeutic agents that IMD 26 may be configured to deliver include, but are not limited to, insulin, morphine, hydromorphone, bupivacaine, clonidine, other analgesics, genetic agents, antibiotics, nutritional fluids, hormones or hormonal drugs, gene therapy drugs, anticoagulants, cardiovascular medications or chemotherapeutics. IMD 26 functions as a drug pump in the example of FIG. 1C, and communicates with external programmer 20 to initialize therapy or modify therapy during operation. In addition, IMD 26 may be refillable to allow chronic drug delivery.

Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some embodiments, IMD 26 may be an external device which includes a percutaneous catheter that forms catheter 28 or that is coupled to catheter 28, e.g., via a fluid coupler. In other embodiments, IMD 26 may include both electrical stimulation as described in IMD 14 and drug delivery therapy.

Catheter 28 may be coupled to IMD 26 either directly or with the aid of a catheter extension (not shown in FIG. 1C). In the example shown in FIG. 1C, catheter 28 traverses from the implant site of IMD 26 to one or more targets proximate to spinal cord 18. Catheter 28 is positioned such that one or more fluid delivery outlets (not shown in FIG. 1C) of catheter 28 are proximate to the one or more target therapy delivery sites within patient 12. In the example of FIG. 1C, IMD 26 delivers a therapeutic agent to targets proximate to spinal cord 18 or nerves that branch from spinal cord 18. IMD 26 may be configured for intrathecal drug delivery into the intrathecal space or epidural delivery into the epidural space both of which surround spinal cord 18. The epidural space (also known as "extradural space" or "peridural space") is the space within the spinal canal (formed by the surrounding vertebrae) lying outside the dura mater, which encloses the arachnoid mater, subarachnoid space, the cerebrospinal fluid, and spinal cord 18. The intrathecal space is within the subarachnoid space, which is past the epidural space and dura mater and through the theca.

Although the target therapy delivery site shown in FIG. 1C is proximate to spinal cord 18 of patient 12, other applications of drug delivery system 24 include alternative target delivery sites. The target delivery site in other applications of drug delivery system 24 may be located within patient 12 proximate to, e.g., sacral nerves (e.g., the S2, S3, or S4 sacral nerves) or any other suitable nerve, organ, muscle or muscle group in patient 12, which may be selected based on, for example, a patient condition. In one such application, drug delivery system 24 may be used to deliver a therapeutic agent to tissue proximate to a pudendal nerve, a perineal nerve or other areas of the nervous system, in which cases, catheter 28 would be implanted and substantially fixed proximate to the respective nerve.

Positioning catheter 28 to deliver a therapeutic agent to various sites within patient 12 enables drug delivery system 24 to assist in managing, e.g., peripheral neuropathy or post-operative pain mitigation, ilioinguinal nerve therapy, intercostal nerve therapy, gastric stimulation for the treatment of gastric motility disorders and/or obesity, and muscle stimulation, or for mitigation of other peripheral and localized pain (e.g., leg pain or back pain). As another example delivery site, catheter 28 may be positioned to deliver a therapeutic agent to a deep brain site or within the heart (e.g., intraventricular delivery of the agent). Delivery of a therapeutic agent within the brain may help manage any number of disorders or diseases including, e.g., depression or other mood disorders, dementia, obsessive-compulsive disorder, migraines, obesity, and movement disorders, such as Parkinson's disease, spasticity, and epilepsy. Catheter 28 may also be positioned to deliver insulin to a patient with diabetes.

IMD 26 may also operate using parameters that define the method of drug delivery. IMD 26 may include programs, or groups of programs, that define different delivery methods for patient 12. For example, a program that controls delivery of a drug or other therapeutic agent may include a titration rate or information controlling the timing of bolus deliveries. Patient 12 may use external programmer 20 to adjust the programs or groups of programs to regulate the therapy delivery.

Just as with IMD 14, IMD 26 may include a posture state module that monitors the patient 12 posture state and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Also, just as with therapy systems 10 (FIG. 1A) and 22 (FIG. 1B), IMD 26 may receive efficacy inputs from patient 12, e.g., via external programmer 20 over a period of time during which patient 12 is in a variety of posture states and present the inputs correlated with the times at which the inputs were received, sensed posture states of the patient at each of the times the patient inputs were received, and therapy programs defining therapy delivery at each of the times the patient inputs were received as a function of time to a user. IMD 26, either automatically or through instruction from external programmer 20 may then adjust subsequent therapy programs to be delivered while patient 12 is in subsequent posture states based on one or more of the correlations between patient input, patient input time, sensed posture state, and therapy program.

Figure 2:
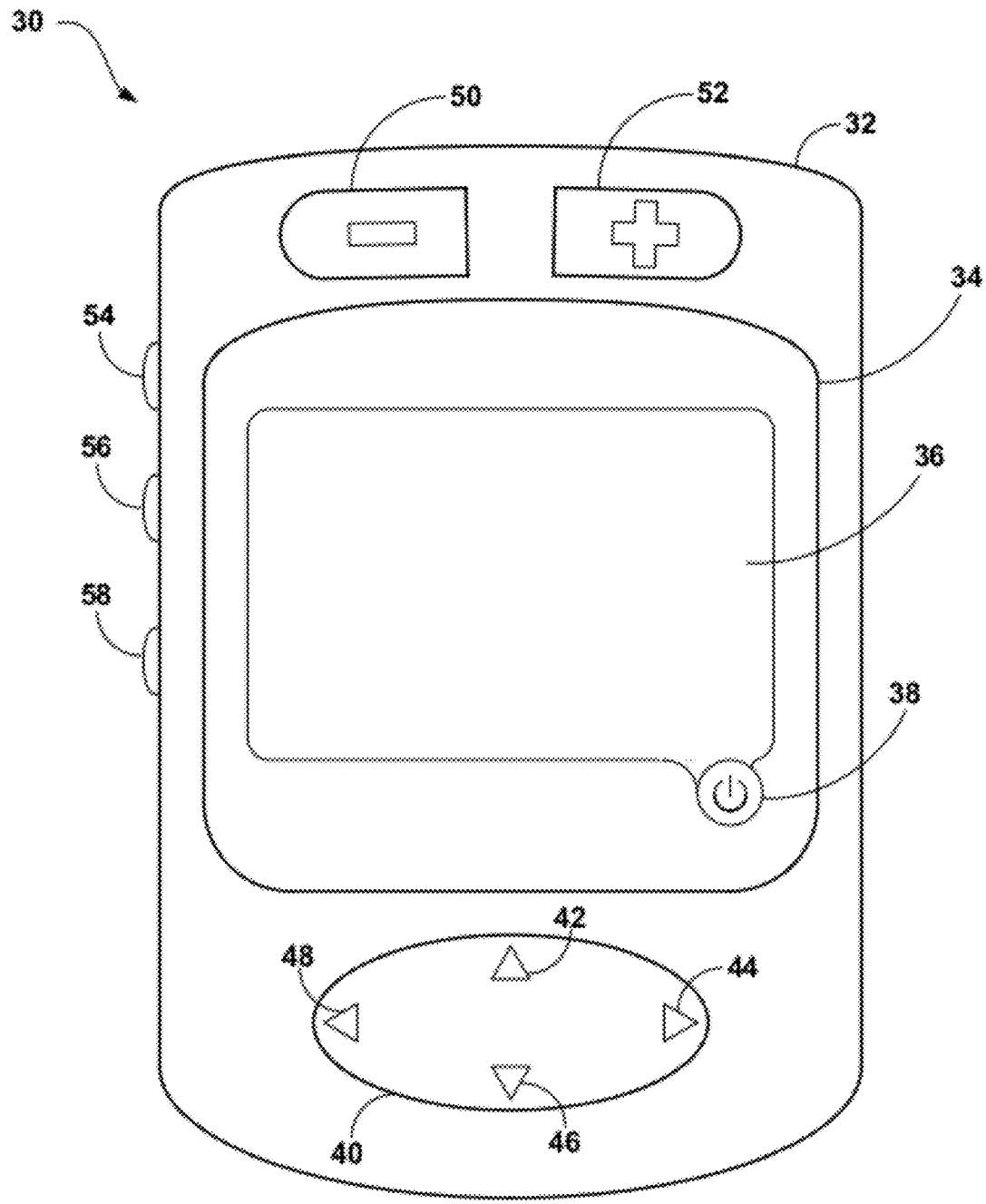
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an implantable medical device. Patient programmer 30 is an example of external programmer 20 illustrated in FIGS. 1A, 1B and 1C and may be used with either IMD 14 or IMD 26. In other examples, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which encloses circuitry necessary for patient programmer 30 to operate. Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein.

Patient programmer 30 also includes display 36, power button 38, increase button 52, decrease button 50, sync button 58, stimulation ON button 54, and stimulation OFF button 56. Cover 34 protects display 36 from being damaged during user manipulation (e.g., interaction) with patient programmer 30. Patient programmer 30 also includes control pad 40 which allows a user to navigate through items displayed on display 36 in the direction of arrows 42, 44, 46, and 48. In some examples, the buttons and control pad 40 take the form of soft keys (e.g., with functions and contexts indicated on display 36), with functionality that may change, for example, based on current programming operation or user preference. In alternative examples, display 36 is a touch screen with which patient 12 may directly interact without the use of control pad 40. A touch screen display may eliminate the use of buttons, such as increase button 52 and decrease button 50, although buttons may be used in addition to a touch screen display.

In the illustrated example, patient programmer 30 is a hand held device. Patient programmer 30 may accompany patient 12 throughout a daily routine. In some cases, patient programmer 30 may be used by a clinician when patient 12 visits the clinician in a hospital or clinic. In other examples, programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Patient 12 may control the illumination level, or backlight level, of display 36 by using control pad 40 to navigate through the user interface and increase or decrease the illumination level with decrease and increase buttons 50 and 52 respectively. In some examples, illumination may be controlled by a knob that rotates clockwise and counter-clockwise to control the operational status of patient programmer 30 and the illumination of display 36. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may include any one or more of liquid crystal display (LCD), dot matrix display, organic light-emitting diode (OLED) display, touch screen, or similar monochrome or color display capable of providing visible information to patient 12. Display 36 may provide a user interface regarding current stimulation therapy or posture state information, or provide a user interface for receiving feedback or medication input from patient 12. Display 36 may also present an active group of stimulation programs, and display operational status of patient programmer 30 or IMDs 14 or 26. For example, patient programmer 30 may provide a scrollable list of groups, and a scrollable list of programs within each group, via display 36. In addition, display may present a visible posture state indication.

Display 36 may also present therapy information, such as patient efficacy inputs correlated with the times at which the inputs were received, sensed posture states of patient 12 at each of the times the patient inputs were received, and therapy programs defining therapy delivery at each of the times the patient inputs were received as a function of time. In one example, the patient inputs and correlated sensed posture states, therapy programs, and patient input times are presented on display 36 as a step function graph. The step function graph may include a first step function plot of patient posture states as a function of time and a second step function plot of therapy programs as a function of time. The patient efficacy inputs may be represented by substantially vertical lines connecting a patient posture state on the first step function plot to a therapy program on the second step function plot at a time at which the patient input was received, the posture state of the patient was sensed, and therapy defined by the therapy program was delivered. Each of the patient efficacy input vertical lines on the step function plots may be further annotated with a symbol indicative of one of a range of efficacy levels. The range of efficacy levels may include, e.g., more than two levels indicated by a set of sequential symbols. In one such example, the set of sequential symbols includes a set of sequential alphanumeric indicators. In another example, the range of efficacy levels includes a satisfactory level and a spectrum of levels above and below the satisfactory level.

In addition to presenting patient efficacy inputs and correlated posture states, therapy programs, and input times, display 36 may present options for a user (e.g., patient 12, a patient caretaker or a clinician) to make selections for adjusting subsequent therapy programs based on one or more of a number of correlations between patient input, patient input time, sensed posture state, and therapy program. For example, display 36 may present an interactive graph, list, table, or other organized aggregation of data representing correlated patient efficacy inputs, patient input times, sensed posture states, and therapy programs. The user may then use patient programmer 30 to set a subsequently delivered therapy program to a previously delivered therapy program based on efficacy, e.g., the therapy program delivered for a particular posture state that received a patient input with the highest level of efficacy for that posture state. The selection options displayed by programmer 30 may be any of a number of user interface controls including, e.g., check-boxes, drop down lists, or radio buttons or any combination thereof.

Patient 12 or another user may interact with control pad 40 to navigate through items displayed on display 36. Patient 12 may press control pad 40 on any of arrows 42, 44, 46, and 48 in order to move between items presented on display 36 or move to another screen not currently shown on the display. In the example of FIG. 2, patient 12 may also use control pad 40 to adjust the volume, display contrast and illumination, time, and measurement units of patient programmer 30. In some examples, pressing the middle of control pad 40 may select any highlighted items presented on display 36. For example, patient 12 may use the middle button of control pad 40 to set a subsequent therapy program to a previously delivered therapy program that patient 12 has highlighted for selection on display 36 based on the patient efficacy input associated with the previous program. In other embodiments, scroll bars, a scroll wheel, individual buttons, or a joystick may perform the complete or partial functions of control pad 40. In alternative embodiments, control pad 40 may be a touch pad that allows patient 12 to move a cursor within the user interface displayed on display 36 to manage therapy or review posture state information.

Decrease button 50 and increase button 52 provide an input mechanism for patient 12. In general, activation of decrease button 50 may decrease the value of a highlighted stimulation parameter. Buttons 50, 52 may be activated by depressing the respective button. In contrast, increase button 52 may increase the value of a highlighted stimulation parameter one step every time the increase button is pressed. While buttons 50 and 52 may be used to control the value of any stimulation parameter, buttons 50 and 52 may also control patient feedback input. When either button 50 and 52 is selected, patient programmer 30 may initialize communication with IMD 14 or 26 to change therapy accordingly.

When depressed by patient 12, stimulation ON button 54 directs programmer 30 to generate a command that is transmitted to IMD 14, where the command instructs IMD 14 to turn on stimulation therapy. Stimulation OFF button 56 turns off stimulation therapy when depressed by patient 12. Sync button 58 causes patient programmer 30 to communicate with IMD 14 within a substantially minimal amount of time from activation of sync button 58. When patient 12 enters an automatic posture response screen of the user interface, activating sync button 58 (e.g., by pressing sync button 58) turns on the automatic posture response to allow IMD 14 to automatically change therapy according to the posture state of patient 12. Activating sync button 58 again, when the automatic posture response screen is displayed, turns off the automatic posture response. In the example shown in FIG. 2, patient 12 may use control pad 40 to adjust the volume, contrast, illumination, time, and measurement units of patient programmer 30.

In some examples, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 and/or may have a different arrangement. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
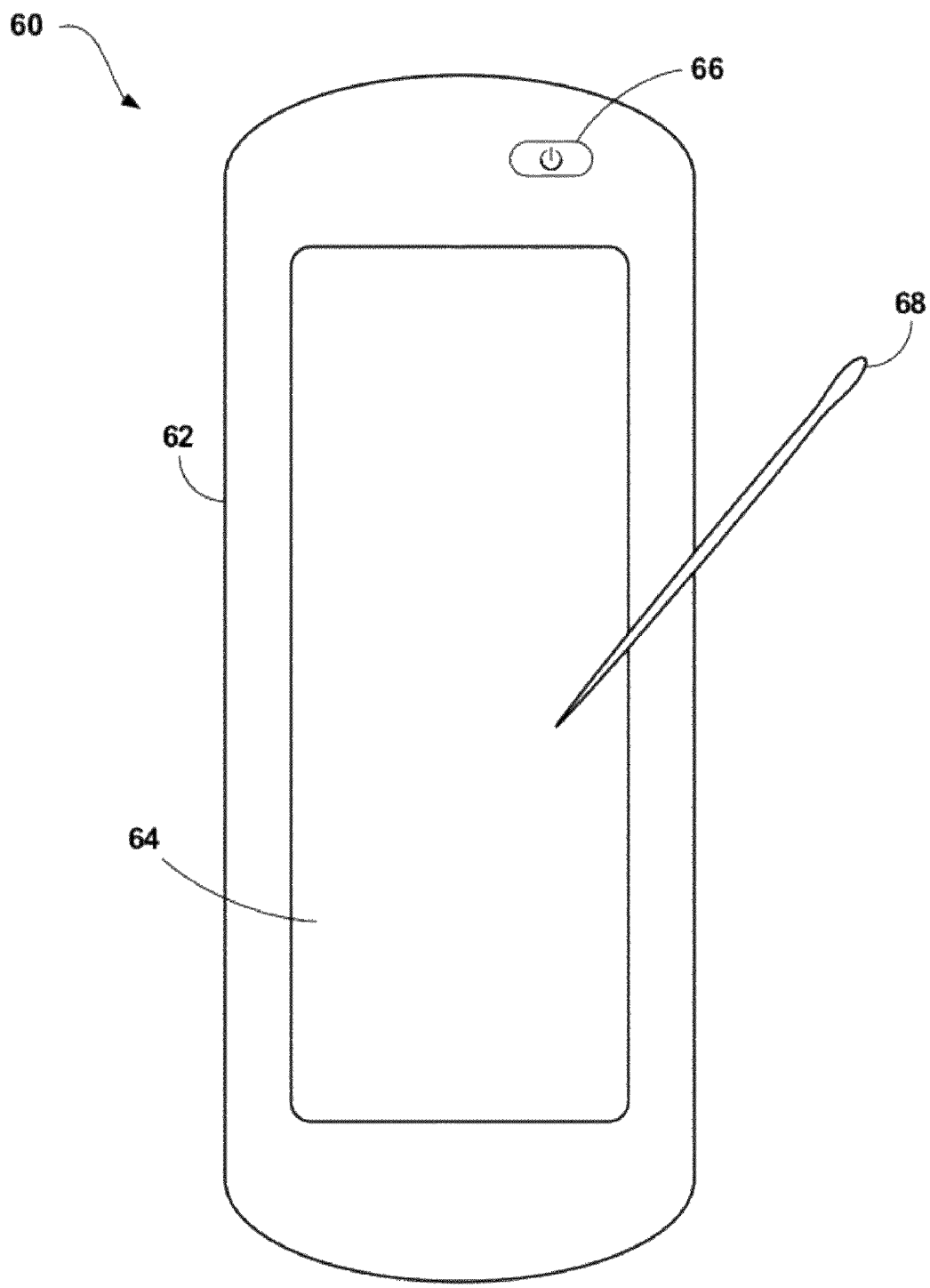
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an implantable medical device. Clinician programmer 60 is an example embodiment of external programmer 20 illustrated in FIGS. 1A, 1B and 1C and may be used with either IMD 14 or IMD 26. In alternative examples, clinician programmer 60 may be used with an external medical device. Clinician programmer 60 provides a user interface (not shown) for a user, such as a clinician, physician, technician, or nurse, to manage and program stimulation therapy. In addition, clinician programmer 60 may be used to review objective posture state information to monitor patient progress and therapy efficacy.

A clinician uses clinician programmer 60 to modify and review therapy to patient 12. With the aid of programmer 60, the clinician may define each therapy parameter value for each of the programs that define stimulation therapy and program IMD 14 or IMD 26 with the selected therapy parameter values. The therapy parameter values, such as amplitude, may be defined specifically for each of the posture states that patient 12 will be engaged in during therapy. In addition, the clinician may use clinician programmer 60 to define each posture state of patient 12 by using, e.g., the posture cones described with reference to FIGS. 8A-8C below, or some other technique for associating posture data received from a posture sensor to the posture state of patient 12.

Clinician programmer 60 includes housing 62, display 64, and power button 66. In the example of FIG. 3, clinician programmer 60 is protected by housing 62, which encloses circuitry necessary for clinician programmer 60 to operate and accommodates display 64 and power button 66. Housing 62 may be constructed of a polymer, metal alloy, composite, or combination material suitable to protect and contain components of clinician programmer 60. In addition, housing 62 may be partially or completely sealed such that fluids, gases, or other elements do not penetrate the housing and affect components therein.

Display 64 is a touch screen that accepts user input via touching certain areas within display 64. The user may use stylus 68 to touch display 64 and select virtual buttons, sliders, keypads, dials, or other such representations presented by the user interface shown by display 64. In some examples, instead of or in addition to stylus 68, the user may touch display 64 with a finger, pen, or any other pointing device. In alternative examples, clinician programmer 60 may include one or more buttons, keypads, control pads, touch pads, or other devices that accept user input, similar to patient programmer 30. Power button 66 may turn clinician programmer 60 ON or OFF as desired by the user. Additionally, clinician programmer 60 may require a password, biometric input, or other security measure to be entered and accepted before a user interacts with the device.

As shown in FIG. 3, clinician programmer 60 is a hand held device. Programmer 60 may be used within the clinic or on in-house patient calls, and to communicate with multiple IMDs 14 and 26 within different patients. In this manner, clinician programmer 60 may be capable of communicating with many different devices and retain and segregate data for more than one patient. Clinician programmer 60 may also take other shapes or sizes not described herein. For example, programmer 60 may take the form of a clam-shell shape, similar to some cellular phone designs. When clinician programmer 60 is closed, at least a portion of display 64 is protected within housing 62. When programmer 60 is opened, on the other hand, one side of the programmer may contain a display while the other side may contain input mechanisms. In some examples, clinician programmer 60 may be a larger, less portable device including, e.g., a notebook computer, workstation, or even a remote computer that communicates with IMD 14 or 26 via a remote telemetry device. In any shape or size, clinician programmer 60 may be capable of performing the requirements described herein.

Most, if not all, of clinician programmer 60 functions may be completed via the touch screen of display 64. The user may program stimulation parameter values, modification profiles, modify therapy programs or groups, retrieve stored therapy data from an IMD or another device, retrieve posture state information from an IMD or another device, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Clinician programmer 60 may also present patient efficacy inputs and correlated posture states, therapy programs, and input times, as well as selection options for adjusting subsequent therapy programs based on one or more of the correlations between patient input, input time, sensed posture state, and therapy program. As with patient programmer 30 in FIG. 2, in some examples, clinician programmer 60 may present patient efficacy inputs correlated with the times at which the inputs were received, sensed posture states of patient 12 at each of the times the patient inputs were received, and therapy programs defining therapy delivery at each of the times the patient inputs were received as a function of time. In one example, the correlations are presented as a step function graph with two step function plots of patient posture and associated therapy program annotated with the patient input indicating the efficacy of each of the programs delivered in the different posture states. In this way, a clinician may use programmer 60 to, e.g., review a historical record of patient therapy and correlated efficacy in a variety of posture states over a period of time through a single graph. The clinician may also, using programmer 60, provide selection inputs for adjusting one or more subsequent therapy programs based on the correlations plotted in the graph presented by the programmer.

In some cases, all processing is performed in IMD 14 and distributed to clinician programmer 60 only for presentation to the clinician. In other cases, IMD 14, clinician programmer 60, patient programmer 30, or another computing device share in the processing duties of therapy adjustment information and any other data prior to presenting the information on clinician programmer 60.

Figure 4:
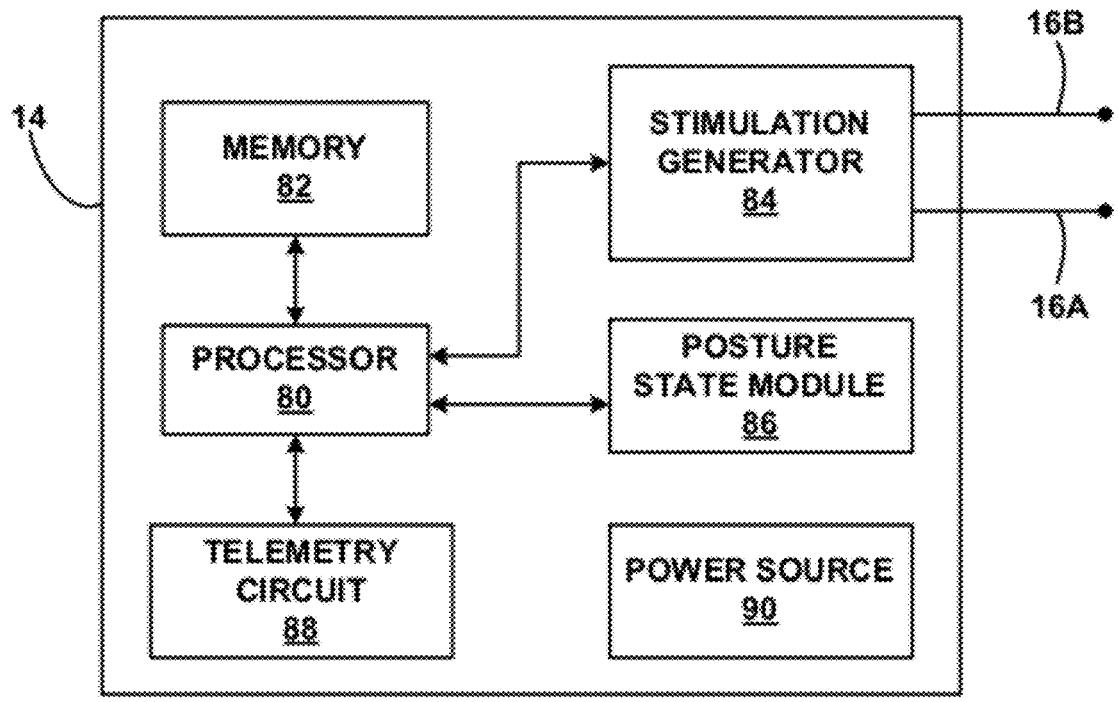
FIG. 4 is a functional block diagram illustrating various components of an implantable electrical stimulator.

FIG. 4 is a functional block diagram illustrating various components of an example IMD 14. In the example shown in FIG. 4, IMD 14 includes processor 80, memory 82, stimulation generator 84, posture state module 86, telemetry circuit 88, and power source 90. Processor 80 is operably connected to and configured to access information from memory 82 and to control stimulation generator 84, posture state module 86, and telemetry circuit 88. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be provided by a hardware device and embodied as software, firmware, hardware, or any combination thereof.

Memory 82 may store instructions for execution by processor 80, stimulation therapy data, posture state information (e.g., posture state definitions, information associating posture states with therapy programs, and the like), posture state indications, and any other information regarding therapy of patient 12. For example, memory 82 may store patient inputs that indicate the efficacy of therapy delivered by IMD 14 to patient 12 in a variety of posture states over a period of time. Memory 82 may also store correlations between the patient inputs and the times at which the inputs were received, sensed posture states of patient 12 associated with the patient inputs (e.g., the posture state sensed at each of the times the patient inputs were received), and therapy programs defining therapy delivery associated with the patient inputs (e.g., the therapy programs implemented by IMD 14 at each of the times the patient inputs were received). Therapy information may be recorded for long-term storage and retrieval by a user, and the therapy information may include any data created by or stored in IMD 14. Memory 82 may include separate memories for storing instructions, posture state information, therapy adjustment information, program histories, patient efficacy inputs, and any other data that may benefit from separate physical memory modules. Memory 82 may include any volatile or non-volatile media, such as a random access memory (RAM), read only memory (ROM), non-volatile RAM (NVRAM), electrically erasable programmable ROM (EEPROM), flash memory, and the like.

Stimulation generator 84 forms a therapy delivery module of IMD 14. Processor 80 controls stimulation generator 84 to deliver electrical stimulation via electrode combinations formed by electrodes in one or more electrode arrays. For example, stimulation generator 84 may deliver electrical stimulation therapy via electrodes on one or more of leads 16, e.g., as stimulation pulses or continuous waveforms. Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy is delivered to a different location within patient 12. In other examples, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities, may be represented by data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations.

When activating stimulation, processor 80 not only accesses the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

According to examples described herein, such stimulation parameters may be adjusted to modify stimulation therapy delivered by IMD 14 based on the detected posture state of patient 12. In some examples, processor 80 detects a posture state transition of patient 12 via posture state module 86 that indicates that a modification of the stimulation therapy is appropriate, e.g., according to instructions stored in memory 82. Processor 80 may access instructions for modifying the stimulation therapy based on the patient 12 posture state, e.g., by changing from a stimulation program appropriate for the previous posture state to a stimulation program appropriate for patient's current posture state, e.g. changing from a program appropriate for lying down to a program appropriate for being upright.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and approximately 1200 Hz, more preferably between approximately 5 Hz and approximately 250 Hz, and still more preferably between approximately 30 Hz and approximately 130 Hz.

2. Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 Hz to approximately 1200 Hz, such as approximately 5 Hz to approximately 250 Hz, or approximately 30 Hz to approximately 185 Hz, and a pulse width in the range of approximately 10 microseconds and 5000 microseconds, such as between approximately 60 microseconds and approximately 1000 microseconds, between approximately 60 microseconds and approximately 450 microseconds, or between approximately 60 microseconds and approximately 150 microseconds. Amplitude ranges such as those described above with reference to SCS, or other amplitude ranges, may be used for different DBS applications.

Processor 80 accesses stimulation parameter values stored by memory 82, e.g., as therapy programs and groups of programs. Upon selection of a particular program group, processor 80 controls stimulation generator 84 to deliver stimulation according to the programs in the groups, e.g., simultaneously or on a time-interleaved basis. A therapy group may include a single program or multiple programs. As mentioned previously, each therapy program specifies values for a set of stimulation parameters, such as amplitude, pulse width, and pulse rate. In addition, each program may specify a particular electrode combination for delivery of stimulation. Again, the electrode combination may specify particular electrodes in a single array or multiple arrays, e.g., on a single lead or among multiple leads. Processor 80 also controls telemetry circuit 88 to send and receive information to and from external programmer 20 or another computing. For example, telemetry circuit 88 may send information to and receive information from patient programmer 30.

Processor 80 determines a patient posture state based on posture state information from posture state module 86. Posture state information may indicate the patient posture, activity level, or any other static position or motion of patient 12. In the example shown in FIG. 4, posture state module 86 may include one or more accelerometers, such as three-axis accelerometers, capable of detecting static orientation or vectors in three-dimensions. Example accelerometers may include micro-electro-mechanical accelerometers. In other examples, posture state module 86 may alternatively or additionally include one or more gyroscopes, pressure transducers or other sensors to sense the posture state of patient 12.

The posture sensors, such as accelerometers may be arranged in different locations with respect to patient 12 and therapy system 10. For example, in the event posture state module includes two posture sensors, one sensor may be connected to IMD 14, while another posture sensor is connected to implantable medical lead 16. In alternative examples first and second posture sensors may be located in different positions within patient 12 and relative to components of therapy system 10. For example, one posture sensor may be an independent implantable sensor that is implanted adjacent but physically disconnected from IMD 14. Alternatively, the sensor may be worn externally on patient 12 adjacent IMD 14. Another posture sensor may be, e.g., connected to an additional sensor lead positioned within patient 12 adjacent electrical leads 16. Alternatively, the other sensor may be an independent implantable sensor that is implanted adjacent but physically disconnected from either of leads 16A and 16B. In some examples, one posture sensor is arranged proximate a therapy delivery site within patient 12, while another sensor is arranged closer to IMD 14 than the first posture sensor.

Posture state information from posture state module 86 may be stored in memory 82 for later review by a clinician, used to adjust therapy, present a posture state indication to patient 12, or some combination thereof. As an example, processor 80 may record the posture state parameter value, or output, of one posture sensor of posture state module 86 and assign the posture state parameter value to a certain predefined posture indicated by the posture state parameter value. In this manner, IMD 14 may define postures of patient 12 with data from the posture sensor(s) of module 86 and track how often patient 12 remains within a certain posture. IMD 14 may also store which group or program was being used to deliver therapy when patient 12 was in the sensed posture, and, in some examples may associate one or more programs or groups with particular posture states of patient 12. Associations between posture states of patient 12 and programs and/or program groups may be stored in memory 82. Further, processor 80 may also adjust therapy for a new posture when posture state module 86 indicates that patient 12 has in fact changed postures. Therefore, IMD 14 may be configured to provide posture-responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes. For example, processor 80 may receive sensed posture state of patient 12 from posture state module 86 and deliver therapy to patient 12 that is defined by a program or program group associated in memory 82 with the sensed posture state or adjust one or more therapy parameters based on the detected posture state.

The posture state information may also be used in addition to the therapy adjustment information when the user desires to view more detailed information related to the posture states engaged by patient 12. Memory 82 may store all of the posture state data detected during therapy or use of IMD 14, or memory 82 may periodically offload the posture state data to clinician programmer 60 or a different external programmer 20 or device. In other examples, memory 82 may reserve a portion of the memory to store recent posture state data easily accessible to processor 80 for analysis. In addition, older posture state data may be compressed to require less memory until later needed by external programmer 20 or processor 80.

A posture state parameter value from posture state module 86 that indicates the posture state of patient 12 may vary constantly throughout the day. However, a certain activity (e.g., walking, running, or biking) or a posture (e.g., standing, sitting, or lying down) may include multiple posture state parameter values from posture state module 86. Memory 82 stores definitions for each posture state of patient 12. In one example, the definitions of each posture state may be illustrated as a posture region, such as a posture cone, in three-dimensional space. Examples of posture cones, which are one type of three-dimensional definitions of posture states, are described below with reference to FIGS. 8A-8C. Whenever the posture state parameter value, e.g., a vector, from one of posture sensors of posture state module 86 resides within a predefined three-dimensional space (e.g., a posture cone), processor 80 indicates that patient 12 is in the posture state associated with that space. In other examples, processor 80 (or a separate processor of posture state module 86) compares a posture state parameter value from one of the posture sensors to a look-up table or equation to determine the posture state in which patient 12 currently resides.

Posture-responsive stimulation may allow IMD 14 to implement a certain level of automation in therapy adjustments. Automatically adjusting stimulation may minimize the need for patient 12 to manually adjust therapy each time patient 12 changes posture or starts and stops a certain posture state. Such manual adjustment of stimulation parameters may be tedious, requiring patient 12 to, for example, depress one or more keys of patient programmer 30 multiple times during the patient posture state to maintain adequate symptom control. In some examples, patient 12 may eventually be able to enjoy posture state responsive stimulation therapy without the need to continue making changes for different postures via patient programmer 30. Instead, patient 12 may transition immediately or over time to fully automatic adjustments based on posture state.

In other embodiments, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some embodiments, to confirm or reject changes in sensed posture state that may result from vibration, patient travel (e.g., in an aircraft, car or train), or some other false positive posture state detection by posture state module 86.

In some embodiments, processor 80 processes the analog output of one of the posture sensors in posture state module 86 to determine activity and/or posture data. For example, where the posture sensor comprises an accelerometer, processor 80 may process the raw signals provided by the sensor to determine activity counts. Activity counts may represent, e.g., a number of footfalls of patient 12. In some embodiments, processor 80 may process the signals provided by the posture sensor to determine velocity of motion information along each axis.

In one example, each of the x, y, and z signals provided by a posture sensor has both a DC component and an AC component. The DC components describes the gravitational force exerted upon the sensor and may thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient.

The AC component of the x, y and z signals yields information about patient motion. In particular, the AC component of a signal may be used to derive a value for an activity describing the patient's motion. This activity may involve a level, direction of motion, or acceleration of the patient.

One method for determining the activity is an activity count. An activity count may be used to indicate the activity or activity level of patient 12. For example, a signal processor may sum the magnitudes of the AC portion of an accelerometer signal for N number of consecutive samples. For instance, assuming sampling occurs as 25 Hz, N may be set to 25, so that count logic provides the sum of the samples that are obtained in one second. This sum may be referred to as an "activity count." The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

Over a period of time during which IMD 14 delivers posture-responsive therapy to patient 12, processor 80 is configured to receive inputs from patient 12 that indicate a level of efficacy of the therapy delivered over the period of time. Processor 80 correlates the inputs to the times at which the inputs were received, sensed posture states of patient 12 (e.g., the sensed posture state at the time the patient input was received), and therapy programs defining therapy delivery (e.g., the therapy program implemented by stimulation generator 84 at the time the patient input was received). Although patient efficacy inputs are generally described herein as associated with a therapy program as a whole, the inputs may also be received for one or more individual parameters within a therapy program. Processor 80 is also configured to present the patient inputs (e.g. via a user interface of external programmer 20 of FIGS. 1A-1C) correlated with input times, sensed posture states of patient 12, and therapy programs. In one example, processor 80 presents the correlations to patient 12 or a clinician via a user interface of external programmer 20 shown in FIGS. 1A-1C. Processor 80 may then instruct IMD 14 to adjust a subsequent therapy program to be delivered while patient 12 is in a subsequent posture state at a subsequent time based on one or more of the correlations between patient input, patient input time, sensed posture state, and therapy program.

After receiving patient efficacy inputs from, e.g., programmer 20, processor 80 of IMD 14 correlates each of the patient inputs to a time at which the input was received, a sensed posture state of the patient at the time the patient input was received, and a therapy program defining therapy delivery at the time the patient input was received. In one example, IMD 14 provides posture-responsive therapy by sensing the posture state of patient 12 using posture state module 86 and generating and delivering therapy according to a therapy program that is associated in memory 82 with the sensed posture state of patient 12. Patient 12 then provides efficacy inputs for the therapy program using external programmer 20. Processor 80 time stamps the patient inputs and correlates the input with the input time, the sensed posture state, and the therapy program. Processor 80 may, for example, store the patient inputs, time, posture state, and therapy program in memory 82 of IMD 14. In another example, processor 80 may transmit the correlated data to another device including, e.g., external programmer 20 for storage thereon through telemetry circuit 88 of IMD 14. The data may be stored in a database, table, list or other organized aggregation of the data that correlates the patient inputs to the input times, posture states, and therapy programs.

Examples disclosed herein including correlating patient inputs to input times, sensed posture states, and therapy program are generally described as correlating patient inputs to the sensed posture state of patient 12 at the time the patient input was received. However, in some examples, patient 12 may provide efficacy inputs that are indicative of a posture state after moving to a different posture state. For example, IMD 14 may deliver therapy to patient 12 during the night while patient 12 is lying down. However, patient 12 may not provide an efficacy input for the therapy delivered during the night until the patient has awoken and is no longer lying down. Therefore, in some examples according to this disclosure, IMD 14, programmer 20, or some other device may correlate each of the patient inputs to input time, therapy program, and a sensed posture state of the patient at a time other than the time the patient input was received, e.g., a posture state occupied by patient 12 sometime before the patient input was received.

Processor 80 is configured to present the patient inputs and correlated input times, posture states, and therapy programs to a user as a function of time. In one example, processor 80 generates a presentation of the correlated data as a step function graph. The step function graph may be presented by processor 80 on, e.g., external programmer 20. In one example, processor 80 communicates with patient programmer 30 using telemetry circuit 88 of IMD 14. Processor 80 compiles the patient inputs and correlated sensed posture states, therapy programs, and patient input times as a step function graph and presents the graph on display 36 of programmer 30.

In another example, processor 80 communicates with clinician programmer 60 using telemetry circuit 88 of IMD 14 to present the patient inputs and correlated sensed posture states, therapy programs, and patient input times as a step function graph on display 64 of programmer 60. In still another example, processor 80 interrogates patient programmer 30 or clinician programmer 60 for patient inputs and correlated posture states, therapy programs, and input times stored thereon and commands the programmer (either 30 or 60) to compile and present the data as a step function graph. As previously indicated, however, in other examples, a processor of programmer 20 or another computing device may compile the patient inputs and correlated sensed posture states, therapy programs, and patient input times and generate the display of the therapy information for presentation to a user.

As described in more detail with reference to FIG. 13, the step function graph presented by processor 80 may include a first step function plot of patient posture states as a function of time and a second step function plot of therapy programs implemented by IMD 14 as a function of time. For each time presented by the step function graph, the therapy programs may correspond to the patient posture states detected at the respective time. In the step function plot, the patient efficacy inputs may be represented by substantially vertical lines connecting a patient posture state on the first step function plot to a therapy program on the second step function plot at a time at which the patient input was received, the posture state of the patient was sensed, and therapy defined by the therapy program was delivered.

Each of the patient efficacy input vertical lines on the step function plots may be further annotated with a symbol indicative of one of a range of efficacy levels. The range of efficacy levels may include, e.g., more than two levels indicated by a set of sequential symbols. In one such example, the set of sequential symbols includes one of a set of sequential numbers or a set of sequential letters. In another example, the range of efficacy levels includes a satisfactory level and a spectrum of levels above and below the satisfactory level. For example, in order of ascending efficacy, the range of levels includes poor, satisfactory, and good.

In some examples, processor 80 may further divided the step function plot of therapy programs into multiple plots related to sets of therapy programs directed at treating, e.g., different conditions or areas of pain. In one such example, processor 80 may present a first step function plot of therapy programs for treating back pain as a function of time and a second step function plot of therapy programs for treating leg pain as a function of time. In this manner, program selection or program parameter selection/adjustment may be improved based on the patient efficacy inputs for multiple conditions and/or areas of pain.

Processor 80 is also configured to adjust subsequent therapy programs based on the correlations between patient input, patient input time, sensed posture state, and therapy program. Processor 80 may adjust the therapy programs automatically or at the direction of patient 12 or another user. In one example, patient 12 may receive therapy from IMD 14 based on many different therapy programs that are associated with different postures over a period of time. During the period, patient 12 may occupy a particular posture state, and, at different times, receive therapy defined by respective therapy programs for the particular posture state, e.g., lying down. Using external programmer 20, patient 12 may transmit inputs to IMD 14 that indicate the efficacy of the various therapy programs that define therapy delivered to patient 12 in the lying down state at different times. Processor 80 may then deliver therapy to patient 12 at a subsequent time by selecting one of the previous therapy programs based on the efficacy inputs received from patient 12. For example, processor 80 may select the therapy program with the highest level of efficacy to define all subsequent therapy delivered to patient 12 in the lying down posture state.

Processor 80 may apply therapy adjustments to one or more posture states at one or more subsequent times. In one example, for a particular posture state, processor 80 associates a therapy program correlated to a patient input with a highest level of efficacy with the patient posture state in memory 82 to guide future therapy deliver. For example, for a lying down posture state, processor 80 can associate a first therapy program that received a patient input with the highest level of efficacy to the lying down posture state in memory 82 regardless of the therapy program that was previously associated with the lying down posture state in memory 82. As a result, in therapy delivery subsequent to the therapy adjustment, processor 80 will control stimulation generator 84 to generate and deliver therapy to patient 12 in accordance with the first therapy program upon detection of the lying down posture state.

In another example, for a particular posture state, processor 80 associates a therapy program correlated to a patient input with a highest level of efficacy for all the posture states, rather than a specific posture state, with the particular posture state in memory 82. In still another example, for a particular posture state, processor 80 associates a therapy program correlated to a patient input with a highest level of efficacy at a particular time (or range of time) with the particular posture state in memory 82. In one such example, the particular time is the same time of day as the time at which the patient efficacy input with the highest level of efficacy was received. In this way, upon detection of the particular posture state in subsequent therapy delivery, processor 80 may control stimulation generator 84 to generate and deliver therapy to patient 12 according to the therapy program that patient 12 previously indicated provided efficacious therapy delivery for a particular time. Adjusting therapy delivery based on a therapy program known to be efficacious at a particular time of day may be useful if, for example, patient 12 engages in a daily pattern of activity, such that patient 12 is known to be occupying a certain posture at a certain time.

In addition to adjusting a single therapy program based on the highest level of patient efficacy input for a particular posture state, for all posture states, or for a particular patient input time, processor 80 of IMD 14 may adjust multiple therapy programs for one or more posture states based on a single correlation between patient input, patient input time, sensed posture state, and therapy program.

In one example, processor 80 adjusts a plurality of subsequent therapy programs associated with a particular posture state based on one correlation between a patient input, patient input time, sensed posture state, and therapy program. For example, processor 80 can set all future therapy programs for the lying down posture state to the therapy program that received a patient input with the highest level of efficacy for the lying down posture state. Alternatively, processor 80 can set all future therapy programs for the lying down posture state to the therapy program that received a patient input with the highest level of efficacy for all the posture states of patient 12, rather than just the lying down posture state.

In another example, processor 80 adjusts a plurality of therapy programs associated with a respective one of a plurality of different posture states based on one correlation between a patient input, patient input time, sensed posture state, and therapy program. For example, processor 80 can set all future applied programs for the lying down and upright posture states to the therapy program that received a patient input with the highest level of efficacy for all the posture states of patient 12. In this manner, processor 80 may adjust therapy delivered in one more posture states in the future based on a single historical correlation between patient input, patient input time, sensed posture state, and therapy program.

Processor 80 may use criteria other than highest efficacy level to adjust subsequent therapy programs. For example, processor 80 may select the therapy program for subsequent therapy delivery to patient 12 with the highest level of efficacy for a particular time of day, day of the week, or other type of time period. In another example, processor 80 may use various averaging or other statistical techniques to combine parameters from various therapy programs that received inputs with the same level of efficacy from patient 12.

Wireless telemetry in IMD 14 with external programmer 20, e.g., patient programmer 30 or clinician programmer 60, or another device may be accomplished by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some embodiments, power requirements may be small enough to allow IMD 14 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 14 when needed or desired.

Figure 5:
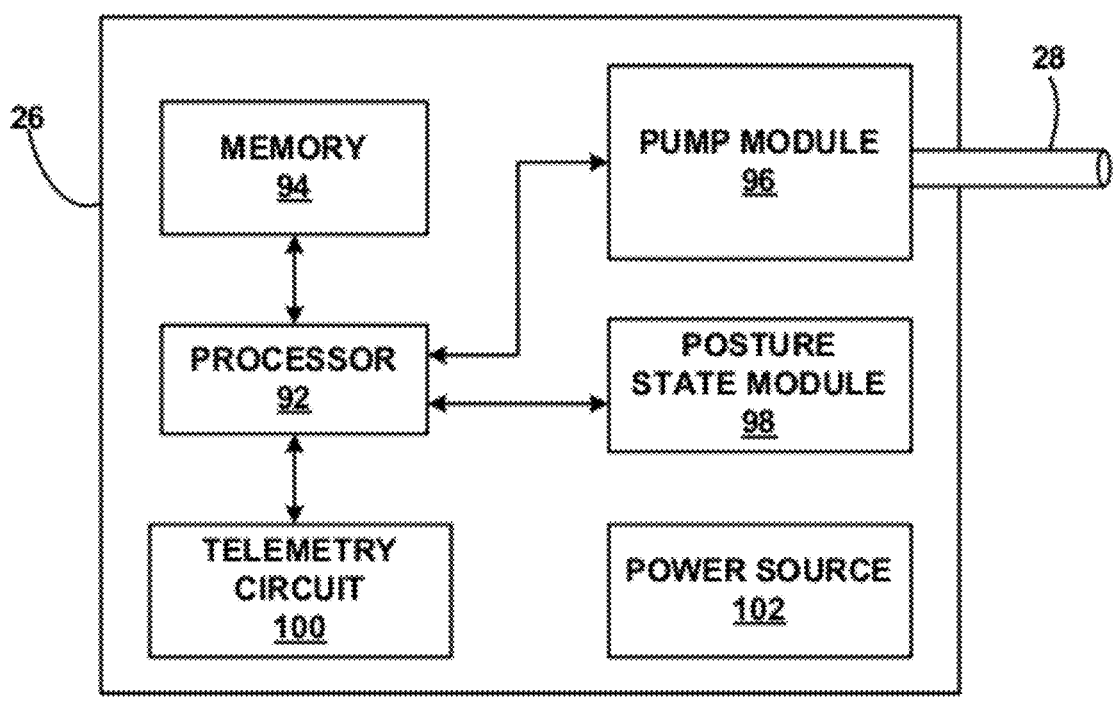
FIG. 5 is a functional block diagram illustrating various components of an implantable drug pump.

FIG. 5 is a functional block diagram illustrating various components of an example IMD 26 that delivers a therapeutic agent to a target therapy delivery site within patient 12. IMD 26 is a drug pump that operates substantially similar to IMD 14 of FIG. 4. IMD 26 includes processor 92, memory 94, pump module 96, posture state module 98, telemetry circuit 100, and power source 102. Instead of stimulation generator 84 of IMD 14, IMD 26 includes pump module 96, which delivers drugs or some other therapeutic agent via catheter 28. Pump module 96 may include a reservoir to hold the drug and a pump mechanism to force drug out of catheter 28 and into patient 12. Posture state module 98 of IMD 26 includes first posture sensor 15 connected to IMD 26 and second posture sensor 17 connected to catheter 28.

Processor 92 may control pump module 96 according to therapy instructions stored within memory 94. For example, memory 94 may contain the programs or groups of programs that define the drug delivery therapy for patient 12. A program may indicate various parameters of the therapeutic agent delivery, such as the bolus size or flow rate of the drug, and processor 92 may accordingly deliver therapy. Processor 92 may also use posture state information from posture state module 98 to adjust drug delivery therapy when patient 12 changes posture states, e.g., transitions between postures. Additionally, and similar to IMD 14, processor 92 of IMD 26 may receive efficacy inputs from patient 12, correlate each patient input to input time, posture state, and therapy program, present the correlations as function of time, and adjust a subsequent therapy program based on one or more of the correlations.

Figure 6:
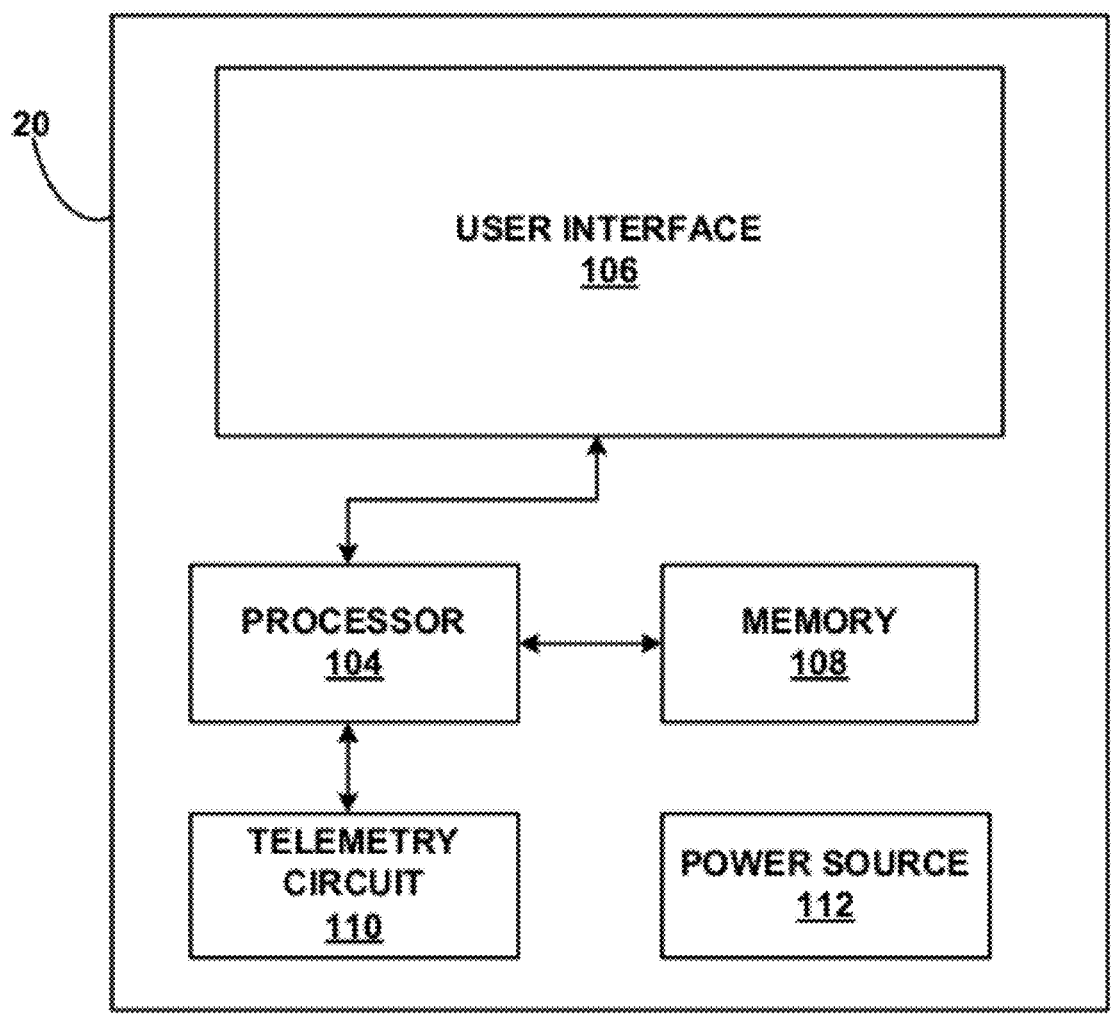
FIG. 6 is a functional block diagram illustrating various components of an external programmer for an implantable medical device.

FIG. 6 is a functional block diagram illustrating various components of an external programmer 20 for an IMD, such as IMD 14 (FIG. 4) or IMD 26 (FIG. 6). As shown in FIG. 6, external programmer 20 includes processor 104, user interface 106, memory 108, telemetry circuit 110, and power source 112. External programmer 20 may be embodied as patient programmer 30 or clinician programmer 60. A clinician or patient 12 interacts with user interface 106 in order to manually change the stimulation parameters of a program, change programs within a group, turn posture-responsive stimulation ON or OFF, view therapy information, view posture state information, or otherwise communicate with IMDs 14 or 26. In addition, as described in further detail below, patient 12 (or a patient caretaker) may interact with programmer 20 to receive efficacy inputs from patient 12, correlate each patient input to input time, posture state, and therapy program, present the correlations as function of time to patient 12, and adjust a subsequent therapy program based on one or more of the correlations.

User interface 106 may include a screen and one or more input buttons, as in the example of patient programmer 30, that allow external programmer 20 to receive input from a user. The input may be, for example, input indicating whether a particular therapy program delivered for a particular patient posture state was efficacious, and, in some examples, a rating (e.g., a numerical rating) of the efficacy. Alternatively, user interface 106 may additionally or exclusively utilize a touch screen display, as in the example of clinician programmer 60. The screen may be a LCD, dot matrix display, OLED display, touch screen, or any other device capable of presenting and/or accepting information.

Input mechanisms for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to therapy delivered to patient 12.

In some examples in which patient 12 is permitted to manually adjust one or more therapy parameter values, user interface 106 presents therapy adjustment information to the user for monitoring adjustments made by patient 12 in different posture states. The therapy adjustment information may be stored within memory 108 of external programmer 20 periodically during therapy, whenever external programmer 20 communicates with IMD 14, or only when the user desired to use the therapy adjustment information. Memory 108 may include a separate memory for therapy adjustment information as opposed to other posture state information or operational instructions. In addition, if memory 108 stores posture state information from more than one patient, memory 108 may use one or more hardware or software security measures to protect the identify of patient 12. For example, memory 108 may have separate physical memories for each patient or the user may be required to enter a password to access each patient's posture state data.

Processor 104 of programmer 20 may be used in conjunction with or in lieu of processor 80 of IMD 14 to receive efficacy inputs from patient 12, correlate each patient input to input time, posture state, and therapy program, present the correlations as function of time, and adjust a subsequent therapy program based on one or more of the correlations. Processor 104 may execute these functions in substantially the same manner as described with reference to processor 80 shown in FIG. 4. However, processor 104 may transmit and receive therapy information to and from other devices in a slightly different manner. As one example, processor 104 can receive efficacy inputs from patient 12 through user interface 106 or another type of input mechanism on programmer 20 and time stamp the input. Processor 104 can interrogate IMD 14 for data related to the sensed posture states of patient 12 and the therapy programs defining therapy delivery correlating to the patient input, e.g., the posture state sensed by IMD 14 and the therapy program implemented by IMD 14 at the time the patient input was received. Processor 104 then correlates each patient input to an input time, and the posture state and therapy program indicated by IMD 14. Processor 104 may store some or all of the correlated data locally on memory 94, or, in another example, remotely including, e.g., storing the data on memory 82 of IMD 14.

Processor 104 may be configured to present to a user, via user interface 106, therapy information to aid the adjustment of therapy by patient 12, where the therapy information includes historical information relating to actual indication of therapy efficacy provided by patient 12. In some examples, processor 104 presents a graphical display of therapy information that correlates the patient efficacy inputs with the input times, sensed posture states of patient 12, and therapy programs as a function of time. In one example, processor 104 presents and user interface 106 displays the patient inputs and correlated sensed posture states, therapy programs, and patient input times as a step function graph.

The step function graph may include a first step function plot of patient posture states as a function of time and a second step function plot of therapy programs as a function of time. The patient efficacy inputs may be represented by substantially vertical lines connecting a patient posture state on the first step function plot to a therapy program on the second step function plot at a time at which the patient input was received, the posture state of patient 12 was sensed, and therapy defined by the therapy program was delivered. Each of the patient efficacy input vertical lines on the step function plots may be further annotated with a symbol indicative of one of a range of efficacy levels. In another example, the range of efficacy levels includes a satisfactory level and a spectrum of levels above and below the satisfactory level.

In addition to presenting patient inputs and correlated posture states, therapy programs, and input times, processor 104 may generate and present a display via user interface 106 that presents selectable options for a user to adjust one or more therapy programs based on one or more of a number of correlations between patient input, patient input time, sensed posture state, and therapy program. For example, processor 104 may compile an interactive graph, list, table, or other organized aggregation of data representing patient efficacy inputs, patient input times, sensed posture states, and therapy programs to display to the user on interface 106. The user may then use one or more input mechanisms of programmer 20 including, e.g., on user interface 106 to associate a particular patient posture state with a therapy program that was previously delivered based on efficacy of that particular therapy program for the particular posture state or one or more different posture state. For example, for a particular posture state, the user may select, via user interface 106, the therapy program that previously received a patient input with the highest level of efficacy for that posture state. Upon selection of the therapy program by the user, processor 104 may associate the therapy program with the patient posture state in memory 108 of programmer 20 or memory 82 of IMD 14 (FIG. 5). Processor 104 may then command IMD 14 to deliver therapy according to adjustments executed using programmer 20.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like.

Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. In other examples, a separate recharging device may be employed that is capable of communication with IMD 14. Then, the recharging device can, in addition to charging IMD 14, transfer programming information, data, or any other information described herein to IMD 14. In this manner, the recharging device may act as an intermediary communication device between external programmer 20 and IMD 14. The techniques described herein may be communicated between IMD 14 via any type of external device capable of communication with IMD 14.

Figure 7:
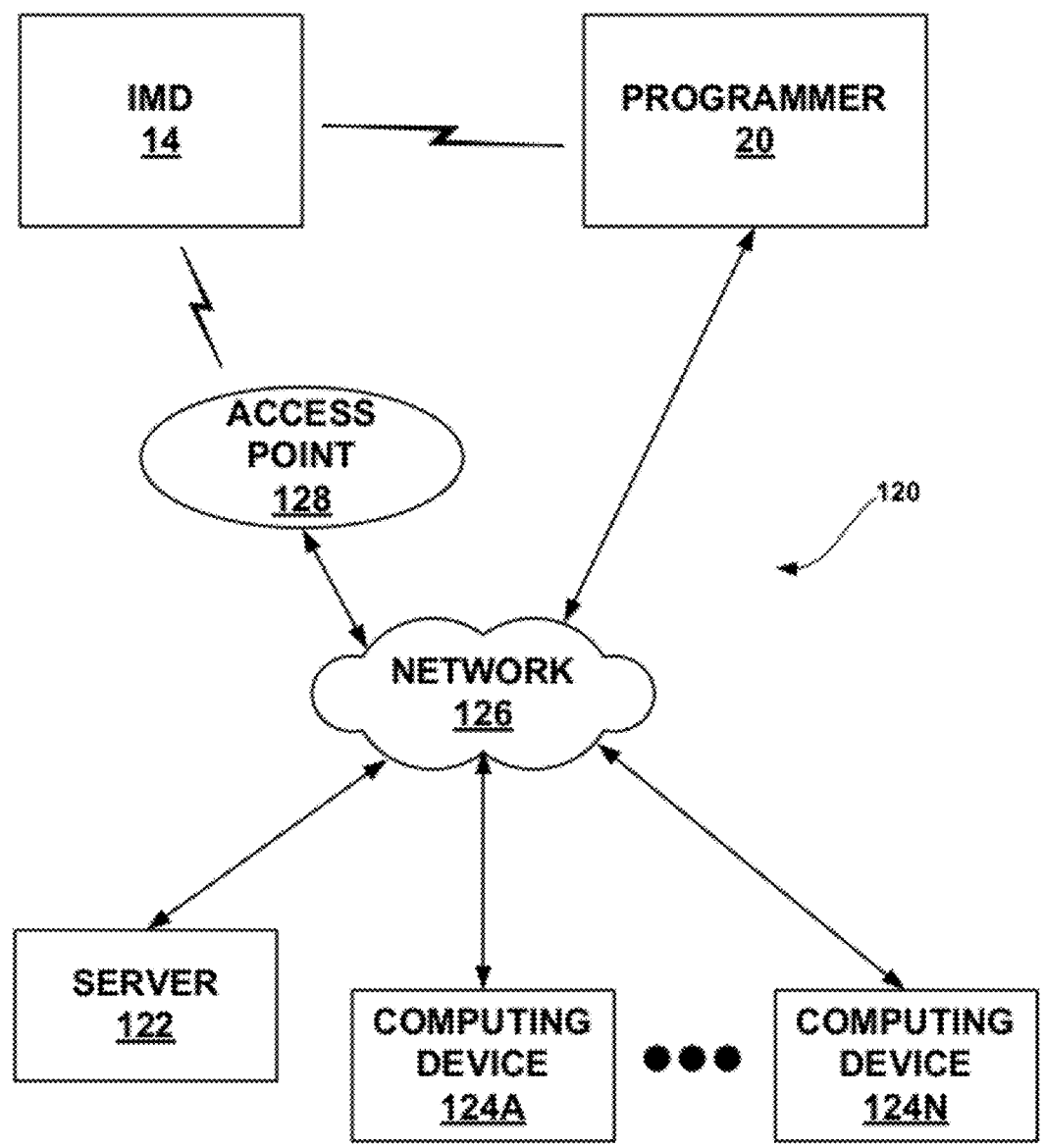
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communicate with an access point 128 via a second wireless connection. In other examples, IMD 26 may also be used in place of IMD 14, and/or external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, DSPs, ASICs, FPGAs, programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day, as well as efficacy inputs received from patient 12 and correlations generated by, e.g., processor 80 between the patient inputs and the times at which the inputs were received, sensed posture states of patient 12 correlated with the efficacy inputs (e.g., the posture states sensed by IMD 14 at the times the efficacy inputs were received), and therapy programs defining therapy delivery at a time correlated with the efficacy inputs (e.g., the therapy program implemented by IMD 14 at each of the times the patient inputs were received). IMD 14 may also process, trend and evaluate the sensed posture state and posture sensor selection information. In some cases, IMD 14 may directly analyze the collected data to, e.g., evaluate the posture state of patient 12, such as what percentage of time patient 12 was in each identified posture. In other cases, however, IMD 14 may send stored data relating to posture state information to external programmer 20 and/or server 122, either wirelessly or via access point 128 and network 126, for remote processing and analysis. In such cases, processing, trending and evaluation functions may be distributed to these other devices such as external programmer 20 or server 122.

Communication between IMD 14 and external devices may occur via network 126 in real time. Network 126 may allow a remote clinician to review the current patient posture state or a remote technician to be alerted to posture sensor malfunctions or failures by receiving a presentation of such information on a remote display, e.g., computing device 124A. In addition, posture state and posture sensor information may be archived by any of these devices to facilitate, e.g., later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, patient efficacy inputs correlated with input times, sensed postures, and therapy programs, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

In the manner of FIG. 7, a clinician, physician, technician, or even patient 12, may review therapy adjustment, efficacy level indications provided by patient 12, and other posture state information from IMD 14. The user may remotely monitor the progress and trends of patient 12, limiting the number of times that patient 12 may need to physically visit the clinician. This monitoring may also reduce the time needed to find efficacious therapy parameters by allowing the clinician to more frequently monitor how patient 12 is using patient programmer 30 and how often changes to therapy must be made. Any of the user interfaces described herein with respect to patient programmer 30 or clinician programmer 60 may also be presented via any of computing devices 124A-124N.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data and therapy information, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients. Further, posture state detection may also be used to provide notifications, such as providing notification via a wireless link to a care giver that a patient has potentially experienced a fall.

Furthermore, although system 120 is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
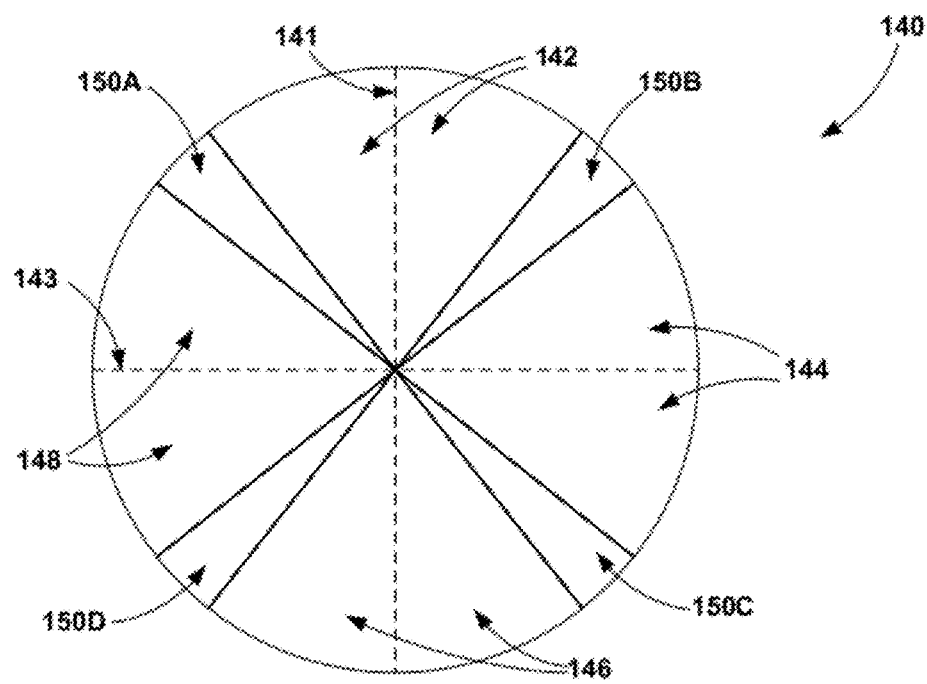
FIGS. 8A-8C are conceptual illustrations of example posture state spaces which may be used to define the posture state of a patient based on signals sensed by a posture sensor.
Figure 8B:
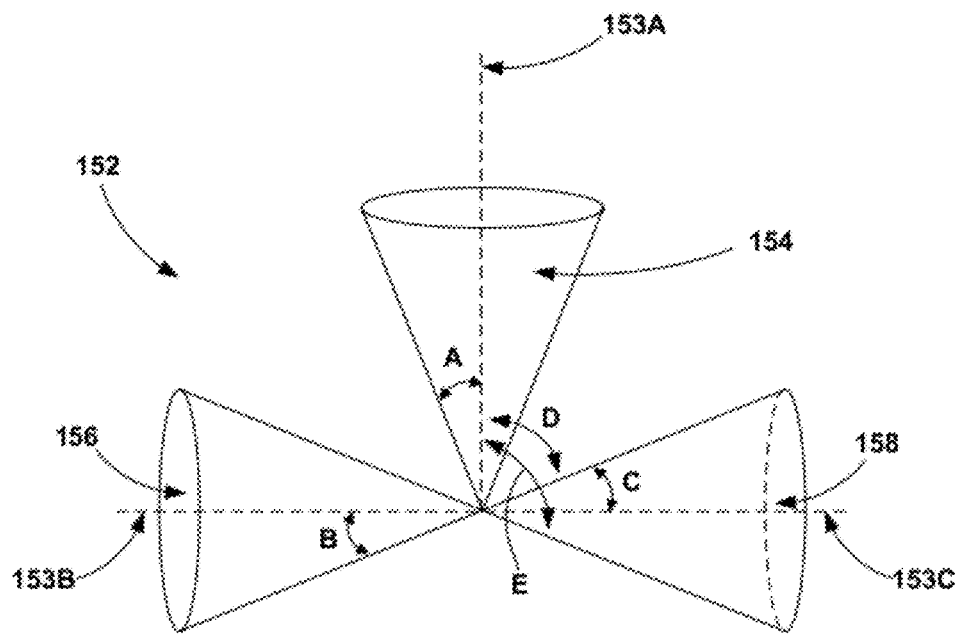
Figure 8C:
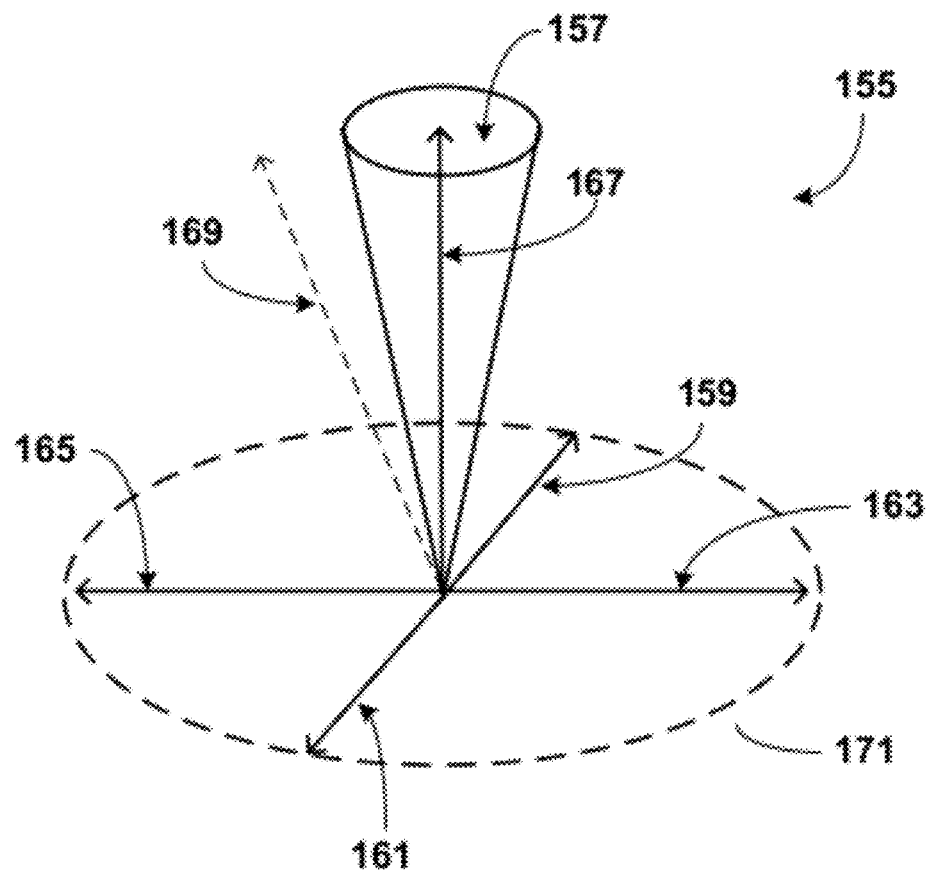

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and 'E' may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159 x lying back vector 165, lying back vector 165 x lying right vector 161, lying right vector 161 x lying front vector 163, and lying front vector 163 x lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Figure 9:
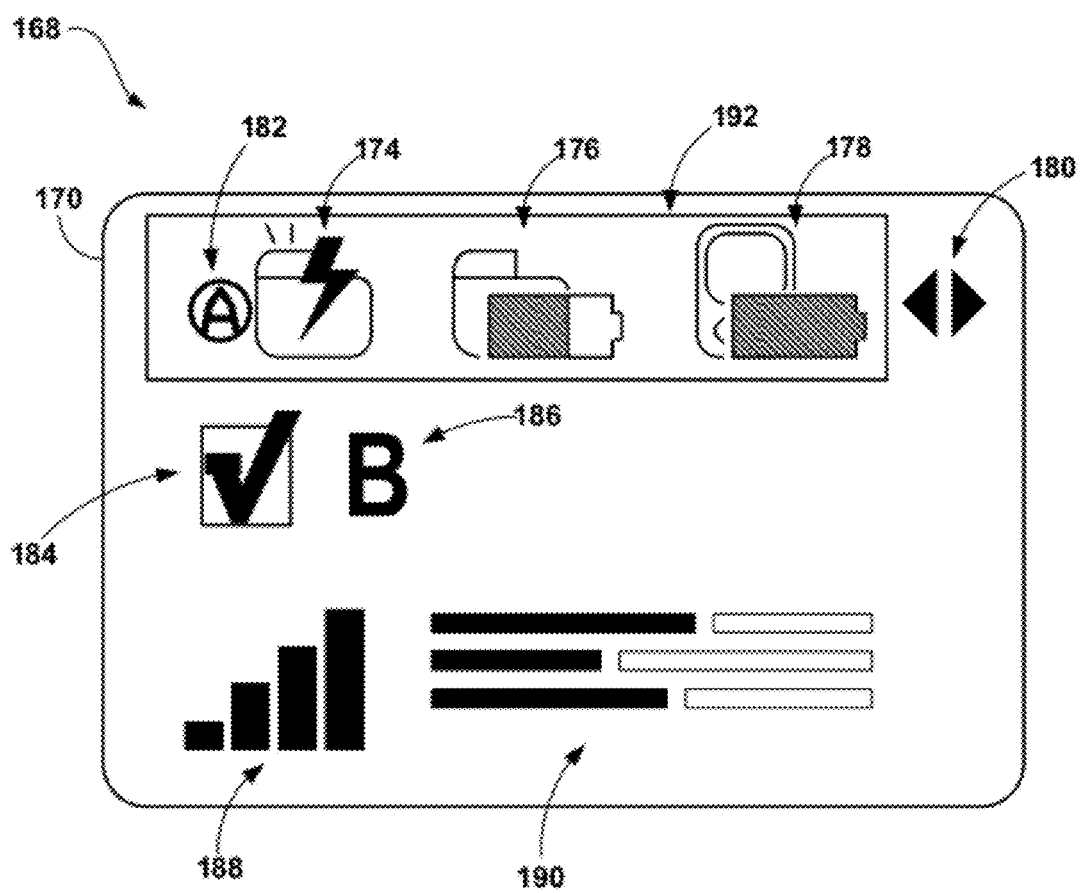
FIG. 9 is a conceptual diagram illustrating an example user interface of a patient programmer for delivering therapy information to the patient.

FIG. 9 is a conceptual diagram illustrating an example user interface 168 of a patient programmer 30 that delivers therapy information to patient 12. In other examples, a user interface similar to user interface 168 may also be shown on clinician programmer 60. In the example of FIG. 9, display 36 of patient programmer 30 provides user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding group, program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example of screen 170 shown in FIG. 9, selection box 192 is positioned so that patient 12 may use navigation arrows 180 via arrows 44 and 48 of control pad 40 (shown in FIG. 2) to move to the automatic posture response screen, the volume screen, the contrast or illumination screen, the time screen, and the measurement unit screen of patient programmer 30. In these screens, patient 12 may control the use of the automatic posture response feature and adjust the patient programmer 30 features. Patient 12 may only adjust the features surrounded by selection box 192.

Group identifier 186 indicates one of possibly several groups of programs that may be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through the program groups, a user may use control pad 40 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example of FIG. 9, no program number is indicated in program identifier 188 because all of the programs' amplitudes are shown in each bar of amplitude graph 190. Solid portions of the bars indicate the relative amplitude IMD 14 currently is using to deliver stimulation therapy to patient 12, while open portions of the bars indicate the remaining amplitude available to each program. In some examples, numerical values of each program's amplitude may be shown in addition to or in place of amplitude graph 190. In other examples of user interface 168 specific to, e.g., drug delivery using IMD 26, amplitude graph 190 may show the flow rate of drugs or frequency of bolus delivery to patient 12. This information may be shown in numerical format as well. Patient 12 may encompass group selection icon 184 with selection box 192 and use navigation arrows 180 via arrows 44 and 48 of control pad 40 to scroll between the different programs of the selected group.

Automatic posture response icon 182 indicates that a posture-responsive therapy mode of IMD 14 is activated, such that processor 80 (FIG. 4) of IMD 14 automatically adjusts therapy to patient 12 based upon the posture state detected by posture state module 86 (FIG. 4). In particular, when the posture-responsive therapy mode of IMD 14 is activated, processor 80 may automatically adjust therapy delivery to patient 12 based on a detected patient posture by adjusting one or more therapy parameter values, selecting different programs or selecting different program groups based on the detected posture state of patient 12. In the example shown in FIG. 9, automatic posture response icon 182 is not present next to group identifier 186. Therefore, group "B" does not have automatic posture-responsive therapy activated for any of the programs within group "B."

Some groups or individual programs in groups may support automatic posture-responsive therapy. For example, automatic adjustment of one or more therapy parameters in response to posture state indication may be selectively activated or deactivated based on settings entered by a clinician, or possibly patient 12. Hence, some programs or groups may be configured for use with posture-responsive therapy while other programs or groups may not be configured for use with posture-responsive therapy. In some cases, if posture-responsive therapy supported by the automatic posture response feature is desired, patient 12 may need to switch therapy to a different group that has automatic posture-responsive therapy activated for IMD 14.

Figure 10:
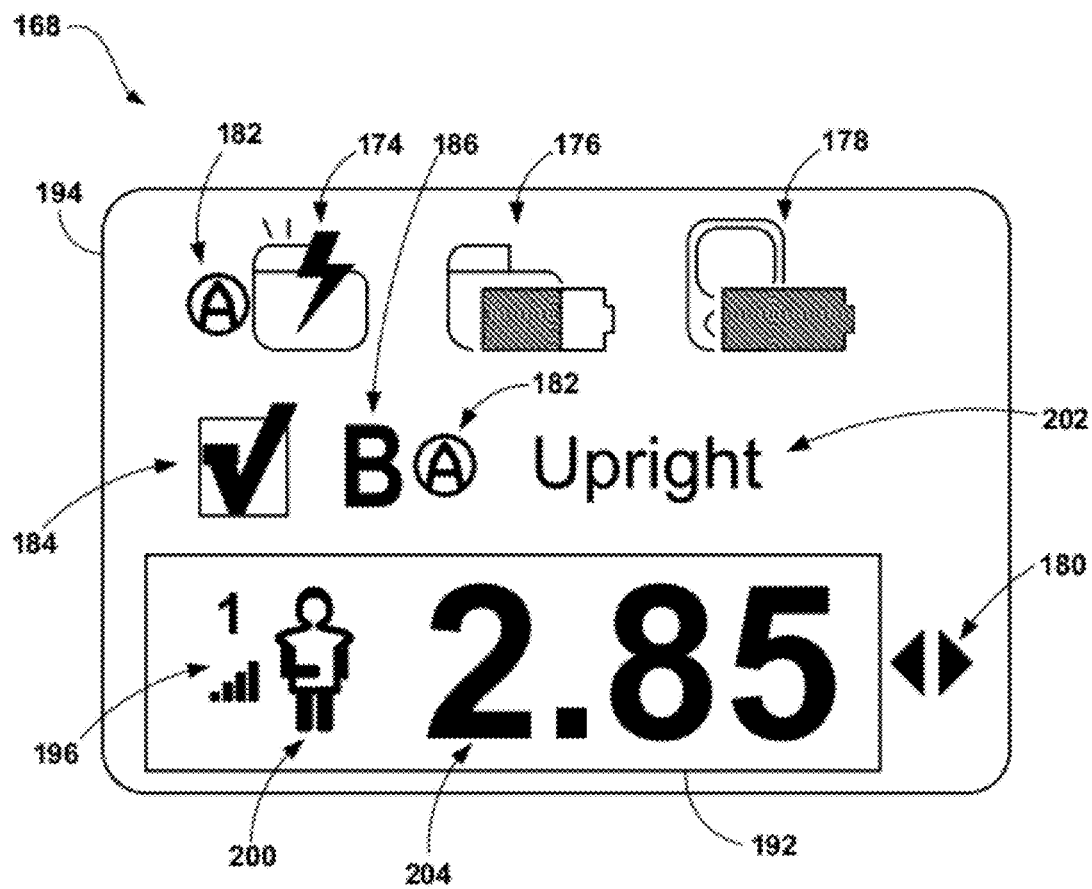
FIG. 10 is a conceptual diagram illustrating an example user interface of a patient programmer for delivering therapy information that includes posture information to the patient.

FIG. 10 is a conceptual diagram illustrating an example user interface 168 of a patient programmer 30 for delivering therapy information that includes posture information to the patient. In other examples, user interface 168 may also be shown on clinician programmer 60. In the example of FIG. 10, display 36 of patient programmer 30 provides user interface 168 to the user, such as patient 12, via screen 194. Just as with screen 170 of FIG. 9, screen 194 presents stimulation icon 174, IMD battery icon 176, programmer battery icon 178, and automatic posture response icon 182. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding a therapy group, therapy program, stimulation amplitude, automatic posture response status (e.g., an indication of whether the posture-responsive therapy mode of IMD 14 is activated), and posture state information. In other examples, user interface 168 may provide more or less information to patient 12, as desired by the clinician or patient 12.

Group identifier 186 indicates that group "B" is active, and automatic posture response icon 182 indicates group "B" (containing one or more programs) is activated to allow IMD 14 to automatically adjust therapy according to the patient 12 posture state. In the example shown in FIG. 10, user interface 168 indicates the posture state determined by IMD 14, e.g., via posture state indication 200 and supplementary posture state indication 202. Program identifier 196 illustrates that information regarding program "1" of group "B" is displayed on screen 194, such as amplitude value 204 illustrating the current voltage amplitude of program "1" is 2.85 Volts. Patient 12 may scroll through different programs of the group by using navigation arrows 180 via arrows 44 and 48 of control pad 40 (shown in FIG. 2).

Posture state indication 200 shows that IMD 14 is detecting that patient 12 is in the upright or standing posture. Supplementary posture state indication 202 supplements posture state indication 200 by providing a textual indication of the exact posture being detected by posture state module 86 of IMD 14. Posture state indication 200 and supplementary posture state indication 202 change according to the sensed, or detected, posture state detected by IMD 14. The posture state may be communicated to the external programmer immediately when IMD 14 detects a posture change, or communicated periodically or non-periodically by IMD 14 unilaterally or upon receiving a request from the programmer. Accordingly, the posture state indication 200 and/or supplementary posture state indication 202 may represent a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

Selection box 192 indicates that patient 12 is viewing other programs within group "B" using selection arrows 180. Selection box 192 may be moved to select other screen levels with control pad 40 in order to navigate through other stimulation groups or adjustable elements of the therapy. When patient 12 selects a different program with control pad 40, program identifier 196 will change number to correctly identify the current program viewed on screen 194.

In addition to graphical, textual or other visible indications of posture state, the external programmer may present audible and/or tactile indications of posture state via any of a variety of audible or tactile output media. An audible indication may be spoken words stating a posture state, or different audible tones, different numbers of tones, or other audible information generated by the programmer to indicate posture state. A tactile (or somatosensory) indication may be, for example, different numbers of vibratory pulses delivered in sequence or vibratory pulses of different lengths, amplitudes, or frequencies.

As described in greater detail with reference to FIGS. 12-16, in some examples, patient programmer 30 is configured to generate and display a graphical user interface to a user, where the graphical user interface presents efficacy inputs and correlations between the patient efficacy inputs, the times at which the inputs were received, sensed posture states of patient 12 (e.g., at each of the times the patient inputs were received), and therapy programs (e.g., the therapy programs defining therapy delivery at each of the times the patient inputs were received) as a function of time. In one example, the correlations are presented as a step function graph including a first step function plot of patient posture states as a function of time and a second step function plot of therapy programs as a function of time.

In addition to presenting patient inputs and correlated posture states, therapy programs, and input times, patient programmer 30 may present options for a user to make selections for adjusting subsequently applied therapy programs based on one or more of the correlations between patient input, patient input time, sensed posture state, and therapy program. For example, display 36 may present an interactive graph, list, table, or other organized aggregation of data representing patient efficacy inputs, patient input times, sensed posture states, and therapy programs. The user may then use patient programmer 30 to associate a particular posture state with a previously delivered therapy program based on efficacy input associated with the therapy program. For example, based on the user input, programmer 30 may associate a particular posture state with the therapy program delivered for a particular posture state that received a patient input with the highest level of efficacy for that posture state.

Figure 11:
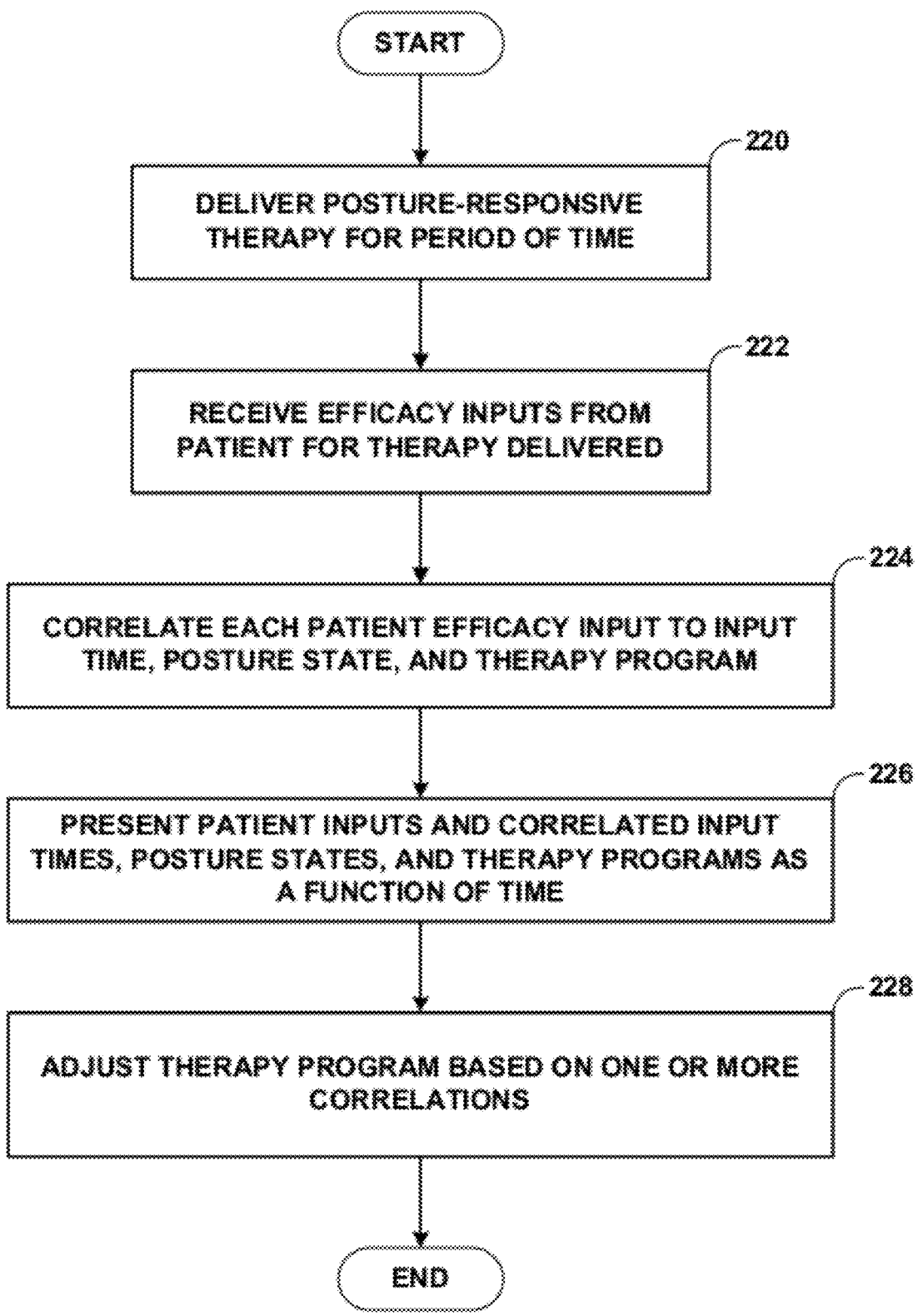
FIG. 11 is a flow chart illustrating an example method of delivering therapy with an implantable medical system.

FIG. 11 is a flow chart illustrating an example method of delivering therapy with an implantable medical system, such as therapy system 10 (FIG. 1A), therapy system 22 (FIG. 1B), or therapy system 24 (FIG. 1C). While therapy system 10 is primarily referred to throughout the description of FIGS. 11-16, in other examples, other therapy systems, such as therapy systems 22 or 24, may implement the example techniques described herein. In the technique shown in FIG. 11, IMD 14 delivers posture-responsive therapy to patient 12 over a period of time, e.g., by selecting one or more therapy programs that define therapy delivery based on one or more a variety of posture states that patient 12 occupies and that are sensed by the posture sensor(s) of posture module 86 (220).

IMD 14 receives patient inputs from, e.g., external programmer 20, that indicate a level of efficacy of the therapy delivered to patient 12 by IMD 14 over the period of time (222). Processor 80 of IMD 14 correlates each of the patient efficacy inputs to a time at which the input was received, a sensed posture state of the patient for which the efficacy input was intended (e.g., as determined by the sensed posture state at the time the patient input was received or immediately prior to the receipt of the patient input), and a therapy program (e.g., the therapy program defining therapy delivery at the time the patient input was received or immediately prior to receipt of the patient input) (224). Processor 80 presents the correlated therapy information to a user via external programmer 20, whereby the efficacy inputs, sensed posture states, and therapy programs may be displayed as a function of time (226). In addition, processor 80 can adjust a therapy program associated with a particular posture state based on one or more of the correlations between the efficacy inputs, sensed posture states, and therapy programs (228).

In the description of FIGS. 11-16, data processing and storage will be described as performed by processor 80 and memory 82 of IMD 14, and data presentation will be described as performed by external programmer 20. However, in other examples, data processing, storage, and presentation functions may be distributed in a different manner between devices of a therapy system. For example, patient efficacy inputs and input times may be stored on memory 108 (FIG. 6) of external programmer 20, while sensed posture states of patient 12 and therapy programs are stored on memory 82 of IMD 14. Processor 80 of IMD 14 may either transmit the posture state and therapy program data to programmer 20 for additional processing, or may interrogate programmer 20 for the patient input and input time data in order to correlate the patient inputs to input times, posture states, and therapy programs.

Additional devices other than IMD 14 and external programmer 20 may also share in the processing, storage, and presentation of patient efficacy input and posture data. For example, as discussed with reference to FIG. 7, correlations between patient efficacy inputs, input times, patient postures, and therapy programs processed by processor 80 of IMD 14 or processor 104 of programmer 20 may be presented as a function of time on one or more remote computing devices 124A-124N, which communicate with IMD 14 and programmer 20 over network 126. Similarly, in another example, processing may be offloaded from IMD 14 or programmer 20 to a remote device including, e.g., server 122 or computing devices 124A or 124N.

In the technique shown in FIG. 11, IMD 14 delivers posture-responsive therapy to patient 12 over a period of time (220). In general, IMD 14 generates and delivers stimulation therapy to a target stimulation site within patient 12 via selected electrodes of leads 16, where the selected electrodes and stimulation parameters are defined by one or more therapy programs implemented by IMD 14. In some examples, processor 80 detects a posture state of patient 12 based on signals from at least one posture sensor of posture state module 86. Processor 80 determines a posture state of patient 12 based on posture state information from the posture sensor(s) of posture state module 86. Posture state information may indicate the patient posture, activity level, or any other static position or motion of patient 12. The posture sensor(s) of posture state module 86 may include accelerometers, such as three-axis accelerometers, capable of detecting static orientation or vectors in three-dimensions.

Processor 80 delivers therapy to patient 12 according to instructions stored in memory 82 that are associated with the posture state of patient 12 sensed by the posture state module 86. Processor 80 accesses stimulation parameter values stored by memory 82 as therapy programs and groups of programs. Upon selection of a particular therapy program or program group, processor 80 controls stimulation generator 84 to deliver stimulation according to the therapy parameter values defined by the one or more therapy programs. If a therapy group associated with a posture state includes more than one therapy program, processor 80 may control stimulation generator 84 to generate and deliver stimulation to patient 12 according to the multiple therapy programs in the groups, e.g., simultaneously or on a time-interleaved basis.

Over a period of time, processor 80 continues to deliver therapy to patient 12 based on a posture state determined by posture state module 86 by transitioning between delivering therapy for one posture state to a new posture state occupied by patient 12. Processor 80 may access instructions for modifying the stimulation therapy based on the patient 12 posture state, e.g., by changing from a therapy program appropriate for the previous posture state to a therapy program appropriate for patient's current posture state. As one example, upon determining patient 12 has transitioned from a lying down posture state to an upright posture state based on a signal generated by posture state module 86, processor 80 may control stimulation generator 84 to transition from generating and delivering therapy according to a first therapy program associated with the lying down posture state to a second therapy program associated with the upright posture state. The first and second therapy programs may include at least one different stimulation parameter value.

Posture-responsive stimulation allows IMD 14 to implement a level of automation in therapy adjustments for patient 12. Automatically adjusting stimulation may free patient 12 from the constant task of manually adjusting therapy each time patient 12 changes posture or starts and stops a certain posture state. Such manual adjustment of stimulation parameters may be tedious, requiring patient 12 to, for example, depress one or more keys of external programmer 20 multiple times during the patient posture state to maintain adequate symptom control. In some examples, patient 12 may eventually be able to enjoy posture state responsive stimulation therapy without the need to continue making changes for different postures via programmer 20. Instead, patient 12 may transition immediately or over time to fully automatic adjustments based on posture state.

In addition to delivering posture-responsive therapy over a period of time (220), IMD 14 also receives patient inputs from external programmer 20 that indicate a level of efficacy of the therapy delivered to patient 12 by IMD 14 over the period of time (222). In general, external programmer 20 receives efficacy inputs from patient 12 that indicate a level of efficacy of the therapy delivered over a period of time during which patient 12 is in a variety of posture states. Although patient efficacy inputs are described as associated with a therapy program as a whole, the inputs may also be received for one or more individual parameters within a therapy program.

In one example, external programmer 20 provides selection options to patient 12 to enable patient 12 to indicate a level of efficacy of therapy that is being delivered to patient 12 for a particular posture state. Patient 12 uses external programmer 20 by, e.g., depressing a button or tapping a soft key on a display or touch screen to select the efficacy level of the therapy. The range of efficacy levels provided as options to patient 12 by programmer 20 may include, e.g., more than two levels indicated by a set of sequential symbols. In one such example, the set of sequential symbols includes one of a set of sequential numbers, e.g., 1 through 5, or a set of sequential letters, e.g., A through E. In another example, the range of efficacy levels includes a satisfactory level and a spectrum of levels above and below the satisfactory level. For example, in order of ascending efficacy, the range of levels may include poor, satisfactory, and good.

Figure 12:
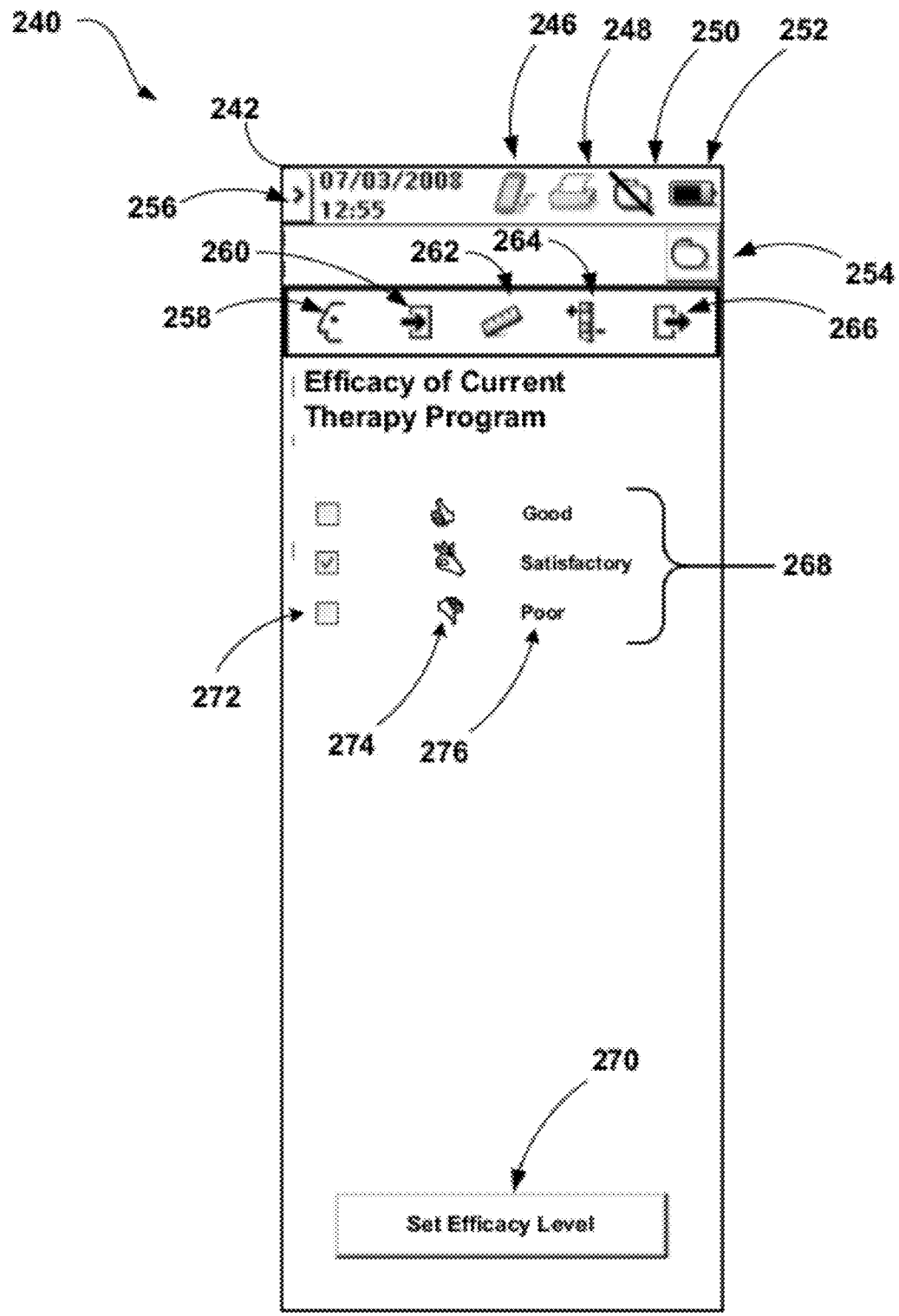
FIG. 12 is a conceptual diagram illustrating an example user interface showing selection options for patient efficacy inputs.

FIG. 12 is a conceptual diagram illustrating an example user interface 240 with which a user, e.g., patient 12, provides inputs that indicate the level of efficacy of therapy delivered by IMD 14. User interface 240 is described as generally being generated and displayed by external programmer 20, which may include patient programmer 30, clinician programmer 60, or some other external programmer or remote device. Additionally, although the efficacy level of therapy is judged by patient 12, users other than patient 12 including, e.g., a clinician may actually provide the efficacy inputs using programmer 20. In any case, user interface 240, in general, displays information related to sensing posture states, automatic posture response, reviewing recorded therapy adjustment information, and patient efficacy input selection options.

In the example of FIG. 12, screen 242 of user interface 240 presents networking icon 246, printer icon 248, IMD communication icon 250, programmer battery icon 252, stimulation status icon 254, operational menu 256, patient data icon 258, data recording icon 260, device status icon 262, programming icon 264, and data reporting icon 266. In addition, screen 242 includes therapy efficacy level selection options 268 and set efficacy level button 270. In some examples, a user may access screen 242 by selecting programming icon 264 to open a drop down menu that allows the user to select one of multiple different screens. The user may select "set efficacy" or some other text or icon that symbolizes access to the process for providing inputs that indicate the level of efficacy of therapy delivered by IMD 14.

Screen 242 includes multiple menus and icons common to other screens of user interface 240. Operational menu 256 is a button that the user may select to view multiple options or preferences selectable by the user. Operational menu 256 may provide preferences for external programmer 20 instead of therapy specific information. Networking icon 246 is shown as grayed out to indicate that programmer 20 is not currently connected to a network. When networking icon 246 is shown fully, external programmer 20 is connected to a network. Printer icon 248 indicates when external programmer 20 is connected to a printer. When printer icon 248 is grayed out as shown in FIG. 11, there is no printer connected to external programmer 20.

Further, IMD communication icon 250 is shown as indicating that external programmer 20 is not in communication with IMD 14 because the icon includes a slash through the IMD representation. The slash is removed when external programmer 20 has established a communication link to IMD 14. In addition, programmer battery icon 252 indicates the current charge level of the battery contained within external programmer 20. Stimulation status icon 254 indicates to the user when stimulation is being delivered to patient 12. Stimulation is not currently being delivered, but stimulation status icon 254 may include an electrical bolt through the IMD representation when stimulation is delivered.

Screen 242 also provides menu options related to stimulation therapy of patient 12. Patient data icon 258 allows the user to enter and review data related to the status of and the condition of patient 12. Data recording icon 260 allows the user to navigate to other screens to enter data recording preferences and review stored data. Device status icon 262 allows the user to view operational status of components of IMD 14, such as electrodes, leads, batteries, and any discovered problems. Programming icon 264 allows the user to navigate to programming screens that define the stimulation therapy parameters used to deliver stimulation to patient 12. In addition, data reporting icon 266 allows the user to view and print reports of the progress of patient 12 and other therapy information.

Patient 12 utilizes therapy efficacy level selection options 268 to provide input indicating the level of efficacy of therapy delivered by IMD 14. Therapy efficacy level selection options 268 include check-box selection inputs 272, efficacy level icons 274, and efficacy level descriptions 276. Patient 12 uses check-boxes 272 to indicate a level of efficacy of the therapy delivered by IMD 14. Although the inputs by which patient 12 selects an efficacy level are shown in FIG. 12 as check-boxes 272, in other examples external programmer 20 may use drop down lists, radio buttons, text boxes, or another appropriate software control that allows patient 12 to input efficacy level. The range of efficacy levels shown in FIG. 12 is represented by a scale including, in order of ascending efficacy "poor," "satisfactory," and "good" as described by efficacy level descriptions 276 and symbolized by efficacy level icons 274. In other examples, the range of efficacy levels provided as options to patient 12 by programmer 20 may include, e.g., more than three levels indicated by a set of sequential symbols. In one such example, the set of sequential symbols includes one of a set of sequential numbers, e.g., 1 through 5, or a set of sequential letters, e.g., A through E.

Patient 12 subjectively determines a level of efficacy of therapy delivered by IMD 14 by checking the relevant check box 272. After patient 12 selects an efficacy level, e.g. selects "satisfactory" as shown in FIG. 12 using check-boxes 272, patient 12 instructs external programmer 20 to retain the efficacy level input by selecting set efficacy level button 270. External programmer 20 may function actively or passively to receive efficacy level inputs from patient 12. For example, upon selection and setting of an efficacy level on screen 242 of user interface 240 by patient 12, processor 104 of programmer 20 may time stamp the patient input and store the data in memory 108. In another example, external programmer 20 may immediately transmit the patient input to IMD 14. Processor 80 of IMD 14 may then time stamp the input and store the data in memory 82. Other combinations of data communication, processing, and storing between patient 12, IMD 14, and external programmer 20 are also included in examples according to this disclosure.

Referring again to the technique shown in FIG. 11, IMD 14 correlates each of the patient efficacy inputs received via user interface 240 to a time at which the input was received, a sensed posture state of the patient, and a therapy program (224). In some examples, IMD 14 correlates each received patient efficacy input with the time at which the input was received, a sensed posture state of patient 12 at the time the efficacy input was received, and a therapy program defining therapy delivery at the time the efficacy input was received. In other examples, such as examples in which patient 12 underwent a posture state transition within a predetermined time range (e.g., less than one minute) prior to receipt of the patient efficacy input, IMD 14 correlates each received patient efficacy input with the time at which the input was received, a sensed posture state of patient 12 at the time immediately preceding the receipt of the efficacy input, and a therapy program defining therapy delivery at the time immediately preceding the receipt of the efficacy input. IMD 14 may detect the posture state transition based on input from posture state module 86 (FIG. 4).

In one example, processor 80 of IMD 14 correlates each of the patient inputs to input time, sensed posture state, and therapy program. For example, IMD 14 provides posture-responsive therapy by sensing the posture state of patient 12 using posture state module 86 and delivering therapy as instructed by processor 80 that is defined by a therapy program that is associated in memory 82 with the sensed posture state of patient 12. Patient 12 provides efficacy inputs for the therapy program using external programmer 20, e.g., as described with reference to user interface 240 in FIG. 12. Processor 80 time stamps the patient inputs and correlates the input with the input time, the sensed posture state, and the therapy program. Processor 80 may also store the correlated patient inputs, time, posture state, and therapy program in memory 82 of IMD 14.

In another example, processor 80 may transmit the correlated data to another device including, e.g., external programmer 20 for storage thereon through telemetry circuit 88 of IMD 14. Processor 80 may store the correlations temporarily or semi-permanently in a database, table, list or other organized aggregation of the data that correlates the patient inputs to the input times, posture states, and therapy programs.

After correlating patient efficacy inputs to input times, sensed posture states, and therapy programs (224), external programmer 20 generates a display that presents the correlated data as a function of time (226). In one example, processor 80 of IMD 14 compiles the patient efficacy inputs correlated to input times, sensed posture states of patient 12, and therapy programs as a function of time over the period during which the efficacy inputs were received from patient 12. Processor 80 then commands telemetry circuit 88 of IMD 14 to transmit the correlated data compiled as a function of time to external programmer 20 for presentation. External programmer 20 presents the patient efficacy inputs correlated with input times, sensed posture states, and therapy programs as a function of time (226) on user interface 106.

In one example, external programmer 20 presents the patient inputs and correlated sensed posture states, therapy programs, and patient input times as a step function graph on user interface 106. FIG. 13 illustrates one such step function graph to be presented to a user on user interface 106 of external programmer 20. In other examples, the step function graph shown in FIG. 13 may be presented on a variety of devices capable of communicating with IMD 14 including, e.g., a notebook, workstation, or other computer that communicates with IMD 14 or 26 via wireless telemetry. In FIG. 13, the step function graph includes a first step function plot 300 of patient posture states as a function of time and a second step function plot 302 of therapy programs as a function of time. Step function plot 300 represents the sensed posture state of patient 12 by IMD 14 over the period of time during which efficacy inputs were received. The patient posture states in first step function plot 300 include "standing," "lying down," and "sitting." In other examples, first step function plot 300 may include other postures including, e.g., "lying front," "lying back," "lying right," or "lying left."

Step function plot 302 represents the therapy programs that defined therapy delivered to patient 12 over the period of time during which efficacy inputs were received. The therapy programs in step function plot 302 include therapy programs A through G. In other examples, step function plot 302 may include more or fewer therapy programs, as well as programs segregated into multiple program groups. Additionally, in some examples, step function plot 302 may be further divided into multiple plots related to sets of therapy programs directed at treating, e.g., different conditions or areas of pain. In one such example, step function plot 302 may be divided into a first step function plot of therapy programs for treating back pain as a function of time and a second step function plot of therapy programs for treating leg pain as a function of time.

Figure 13:
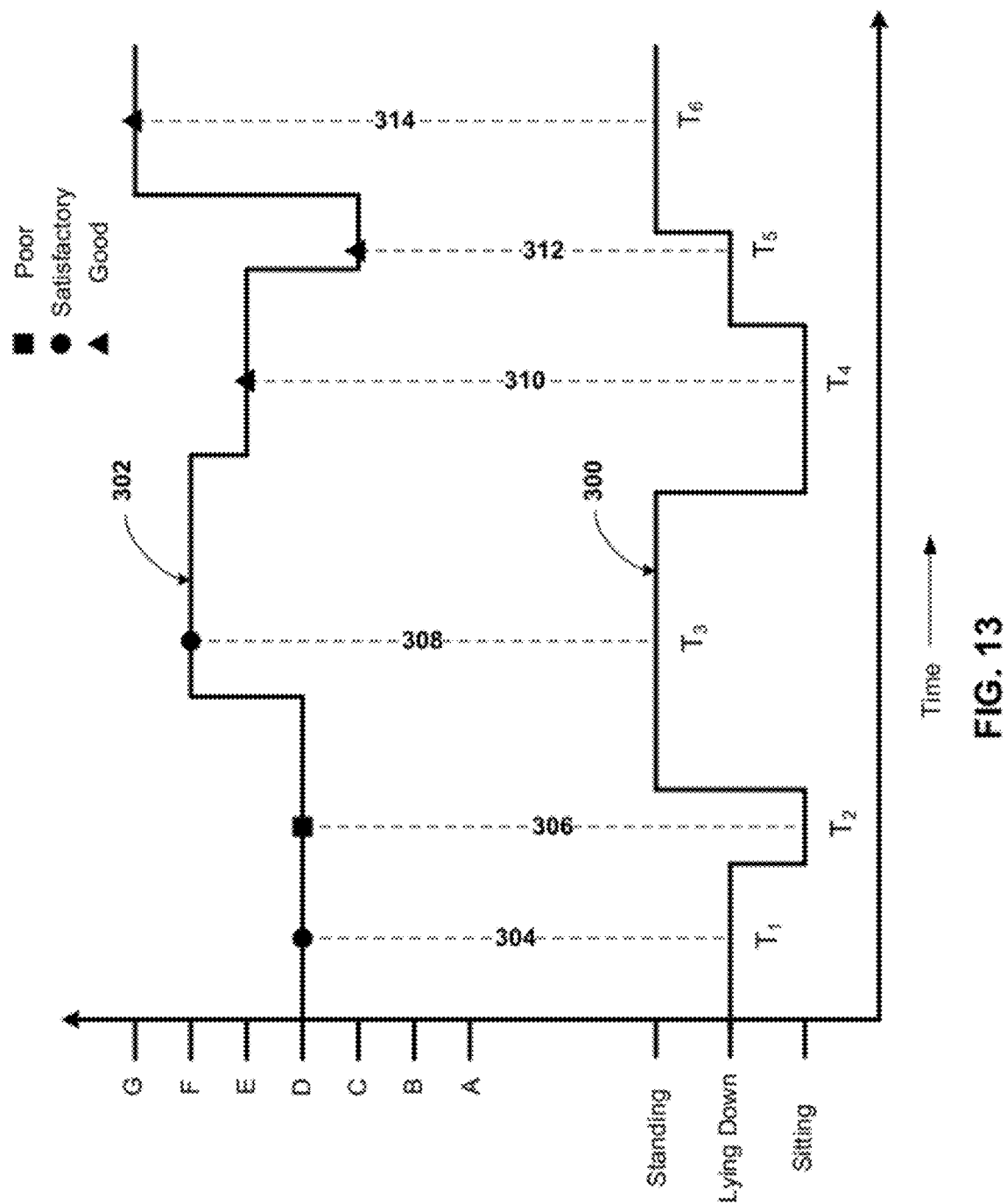
FIG. 13 is a conceptual diagram illustrating an example presentation of patient efficacy inputs correlated with input time, posture state, and therapy program as a function of time.

Efficacy inputs received from patient 12 are represented in FIG. 13 by dashed vertical lines connecting a patient posture state on first step function plot 300 to a therapy program on second step function plot 302. In some examples, the dashed vertical lines indicative of a patient efficacy input connects a patient posture state sensed by IMD 14 at a time at which the patient input was received with the therapy program implemented by IMD 14 at the time the patient input was received. The example of FIG. 13 shows six patient efficacy inputs 304-314 at six times $T_1$-$T_6$ respectively. In other examples, external programmer 20 may present a greater or fewer number of patient efficacy inputs received from patient 12 over a shorter or longer period of time.

Each of patient efficacy input vertical lines 304-314 connecting first and second step function plots 300, 302 is annotated with a symbol indicative of one of a range of efficacy levels. The range of efficacy levels shown in FIG. 13 is represented by a scale including, in order of ascending efficacy "poor," "satisfactory," and "good" as described with reference to FIG. 12. In general, the range of efficacy levels may include more than two levels indicated by a set of sequential symbols. In one such example, the set of sequential symbols includes one of a set of sequential numbers or a set of sequential letters.

As shown in FIG. 13, patient 12 received posture-responsive therapy from IMD 14 defined by five different therapy programs D, F, E, C and G during the time period illustrated in FIG. 13, during which time patient 12 transitioned between the lying down, sitting, and standing posture states six times. Over the total period of time illustrate in FIG. 13, patient 12 provided six efficacy inputs 304-314 at six times $T_1$-$T_6$, respectively, during the course the implementation of five therapy programs D, F, E, C and G by IMD 14 and the six posture state changes detected by IMD 14.

The changes in therapy programs illustrated in FIG. 13 may represent one of many posture-responsive therapy delivery techniques implemented by IMD 14. In one example, IMD 14 automatically switches therapy programs based on the sensed posture state of patient 12, such as by determining which therapy program is associated with a sensed posture state in memory 82 (FIG. 4) and implementing the associated therapy program upon detection of the sensed posture state. In some examples, IMD 14 is configured to switch therapy programs based on a sensed posture state only if patient 12 occupies the sensed posture state for a minimum period of time. The minimum period of time may be a dwell time, which indicates a period of time following a detection of a posture state transition by IMD 14 and prior to an initiation of a change in therapy to accommodate the posture state transition. In this way, IMD 14 is configured with a dwell time that prevents therapy program changes for a particular sensed posture until IMD 14 determines that patient 12 is likely to remain in that state, i.e. the posture state is stable.

In examples in which IMD 14 implements a dwell timer prior to switching therapy programs in response to a sensed posture state transition, IMD 14 may not necessarily switch between therapy programs when patient 12 changes posture. For example, in the example shown in FIG. 13, when patient 12 is in a lying down posture state, IMD 14 delivers therapy according to therapy program D, and when patient 12 transitions from the lying down posture state to the sitting posture state, IMD 14 does not discontinue therapy delivery according to therapy program D, because, e.g., patient 12 only occupies the sitting down posture state for a relatively short period of time before transitioning back to the standing posture state. IMD 14 may determine that the required dwell time has not been satisfied for the sitting posture state, e.g., because patient 12 transitioned to the standing posture state within a particular range of time, such that IMD 14 does not switch therapy delivery to accommodate the sitting posture state.

In another example, the switches between therapy programs illustrated in FIG. 13 represents a posture-responsive therapy delivery technique in which patient 12, or another user such as a clinician, controls the therapy program implemented by IMD 14. For example, the clinician may be testing or programming IMD 14 for therapy delivery in different posture states using external programmer 20. In examples where a user is controlling therapy adjustments, patient 12 may manually adjust therapy programs based on the posture state they occupy and the efficacy of therapy delivered by different programs. In FIG. 13, patient 12 manually selects therapy program D for both lying down and sitting. However, patient 12 rates the efficacy of program D higher for sitting down at time $T_2$ than for lying down at time $T_1$.

FIG. 13 also illustrates that IMD 14 may deliver therapy that is defined by different therapy programs at different times, in spite of patient 12 occupying the same posture state at those times. This may occur, e.g., during a testing or programming phase of IMD 14 and may be automatically controlled by IMD 14 or manually selected by patient 12 using external programmer 20. For example, in FIG. 13, IMD 14 delivers therapy to patient 12 for a standing posture state that is defined by therapy program F for a period of time. At a later time, however, IMD 14 delivers therapy to patient 12 for the standing posture state that is defined by therapy program G. In the example shown in FIG. 13, patient 12 indicated that the efficacy level of therapy program F for the standing posture is "satisfactory" at time $T_3$. At time $T_6$, patient 12 indicated that the efficacy level of therapy program G for the standing posture improved to "good." The implementation of different therapy programs for the same posture state may represent automatic optimization of posture-responsive therapy performed by IMD 14 cycling through different therapy programs according to one or more search algorithms, patient 12 manually adjusting the therapy delivered by IMD 14 to increase efficacy, or a lack of posture-responsive therapy delivery by IMD 14 because of a failure of patient 12 to satisfy a dwell time for the posture state. As indicated above, in some examples, patient 12 must occupy a particular posture state for the dwell time prior to IMD 14 switching therapy programs to accommodate the particular posture state.

In other examples, therapy changes for the same posture may represent parameter adjustments made by patient 12 using external programmer 20 during an automatic posture-responsive therapy session delivered by IMD 14 as part of a chronic, as opposed to a test, therapy session. In such examples, patient 12 may not be able to substantially alter the automatic posture-responsive therapy delivered by IMD 14, but may be allowed to make minor adjustments on an ad-hoc basis to further improve efficacy. Whatever the particular context in which patient 12 provides efficacy inputs that are correlated to input times, sensed posture states, and therapy programs by IMD 14, patient 12 (or another user, e.g., a clinician) may use external programmer 20 to review a historical record of patient therapy and correlated efficacy in a variety of posture states over a period of time through a single graphical display such as, e.g., the step function graph shown in FIG. 13.

Referring again to the technique of FIG. 11, in addition to external programmer 20 presenting the correlated data as a function of time (226), external programmer 20 and/or IMD 14 may adjust the therapy programs associated with one or more posture states for subsequent posture-responsive therapy delivery based on one or more of the correlations between patient input, patient input time, sensed posture state, and therapy program (228).

In one example, IMD 14 automatically adjusts one or more associations between therapy programs and posture states based on the correlations between patient input, patient input time, sensed posture state, and therapy program. As previously described, the correlations between patient input, patient input time, sensed posture state, and therapy program may be determined during a period of time in which processor 80 controls stimulation generator 84 to generate and deliver therapy to patient 12 over a period of time based on different therapy programs associated in memory 82 with different posture states. During the period of time, at different times, IMD 14 delivers therapy according to a plurality of therapy programs for a single posture state, e.g., a lying down posture state. Using external programmer 20, patient 12 provides efficacy inputs that indicate the efficacy of one or more of the plurality of therapy programs. Processor 80 receives the efficacy inputs from programmer 20, and stores the efficacy input and associated sensed posture state and therapy program in memory 82.

In some examples, IMD 14 automatically adjusts one or more associations between therapy programs and posture states based on the correlated efficacy inputs, sensed posture states, and therapy programs by determining the therapy program for which patient 12 provided the highest efficacy input for a particular posture state, and associates that therapy program with the particular posture state in memory 82 of IMD 14. In other examples, IMD 14 automatically adjusts the one or more therapy programs for posture-responsive therapy delivery by selecting the therapy program for which patient 12 provided the highest efficacy input for a particular posture state and also has a highest relative efficiency (e.g., because of a relatively low energy consumption by IMD 14 when generating and delivering therapy according to the therapy program). In yet other examples, IMD 14 automatically adjusts the one or more therapy programs for posture-responsive therapy delivery by associating a particular posture state with a therapy program that received the highest indication of efficacy by patient 12, regardless of whether the therapy program was previously associated with the particular posture state.

In some examples, IMD 14 automatically adjusts one or more associations between therapy programs and posture states based on the correlated efficacy inputs, sensed posture states, and therapy programs by determining the therapy program for which patient 12 provided the highest efficacy input for a particular posture state at a particular time of day. In some cases, IMD 14 selects different therapy programs for the same posture state based on the time of day at which the posture state is sensed. For example, IMD 14 may provide therapy delivery according to a first therapy program if a posture state is sensed at a first time of day and IMD 14 may provide therapy delivery according to a second therapy program if the posture state is sensed at a second time of day. Thus, in some examples, processor 80 of IMD 14 can automatically adjust one or more therapy programs for a first posture state and a first time of day based on a therapy program associated with the highest patient efficacy rating and previously-implemented by IMD 14 for the first posture state at the first time of day.

Other types of automated therapy adjustments based on the correlations between patient input, patient input time, sensed posture state, and therapy program are contemplated. After processor 80 adjusts the one or more associations between therapy programs and posture states based on the correlated efficacy inputs, sensed posture states, and therapy programs, processor 80 controls stimulation generator 84 to generate and deliver stimulation therapy to patient 12 at a subsequent time based on the adjusted associations between one or more therapy programs and posture states. In this way, IMD 14 may automatically adjust therapy delivery based on the efficacy inputs received from patient 12.

In another example of adjusting subsequent therapy delivered to patient 12, a user (e.g., patient 12, a patient caretaker or a clinician) may adjust posture-responsive therapy delivery by IMD 14 based on the correlations between patient efficacy input, patient input time, sensed posture state, and therapy program. For example, external programmer 20 can present the patient inputs and correlated input times, posture states, and therapy programs via user interface 106 as a step function graph, e.g., as shown in FIG. 13. In general, patient 12 may then use programmer 20 to associate one of the previously-implemented therapy programs to a particular posture state based on one or more of the correlations between patient efficacy input, input time, posture state, and therapy program.

For example, based on the graphical illustration of the correlated input times, posture states, and therapy programs, patient 12 may determine that for a particular posture state, a first therapy program was more effective than a second therapy program, where the first and second therapy programs were actually implemented by IMD 14 at different times while patient 12 occupied the particular posture state. Accordingly, patient 12 may use programmer 20 to associate the first therapy program with the particular posture state for future posture-responsive therapy delivery by IMD 14.

As another example, based on the graphical illustration of the correlated input times, posture states, and therapy programs, patient 12 may determine that for a particular posture state, a first therapy program was effective, where the first therapy program may have been, but was not necessarily implemented by IMD 14 while patient 12 occupied the particular posture state. Patient 12 may use programmer 20 to associate the first therapy program with the particular posture state for future posture-responsive therapy delivery by IMD 14.

In still another example, based on the graphical illustration of the correlated input times, posture states, and therapy programs, patient 12 may determine that for a particular posture state and a particular time of day, a first therapy program was more effective than a second therapy program that was also delivered to patient 12 while patient 12 occupied the particular posture at the particular time of day. Patient 12 may use programmer 20 to associate the first therapy program with the particular posture state for future posture-responsive therapy delivery by IMD 14 at the particular time of day. The time of day may be, for example, a range of time (e.g., 9:00 a.m. to 11:00 a.m.) during which patient 12 is expected to occupy the same posture state.

Figure 14:
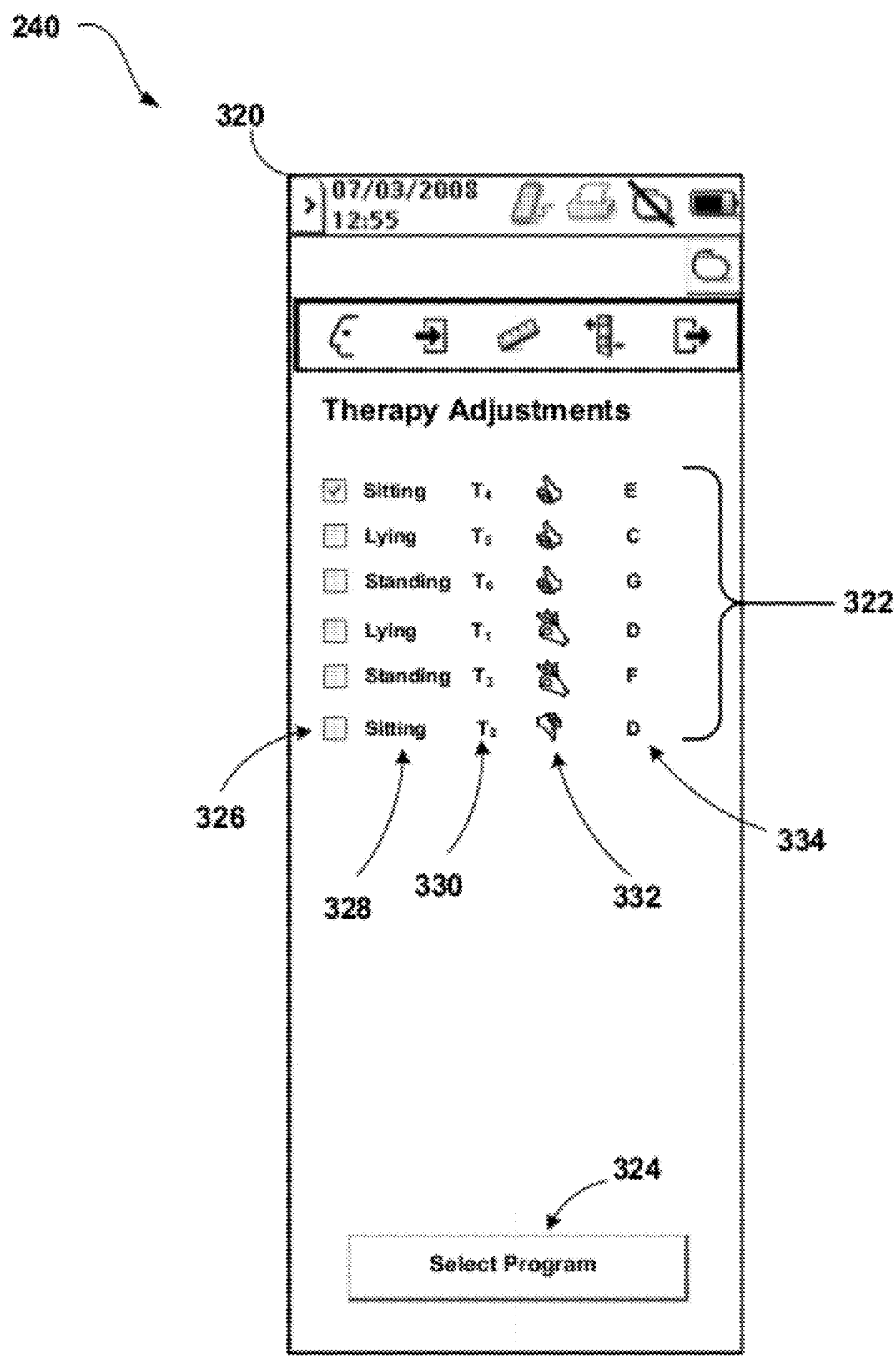
FIG. 14 is a conceptual diagram illustrating an example user interface for selecting a therapy program based on one or more of the correlations of FIG. 13.
Figure 15:
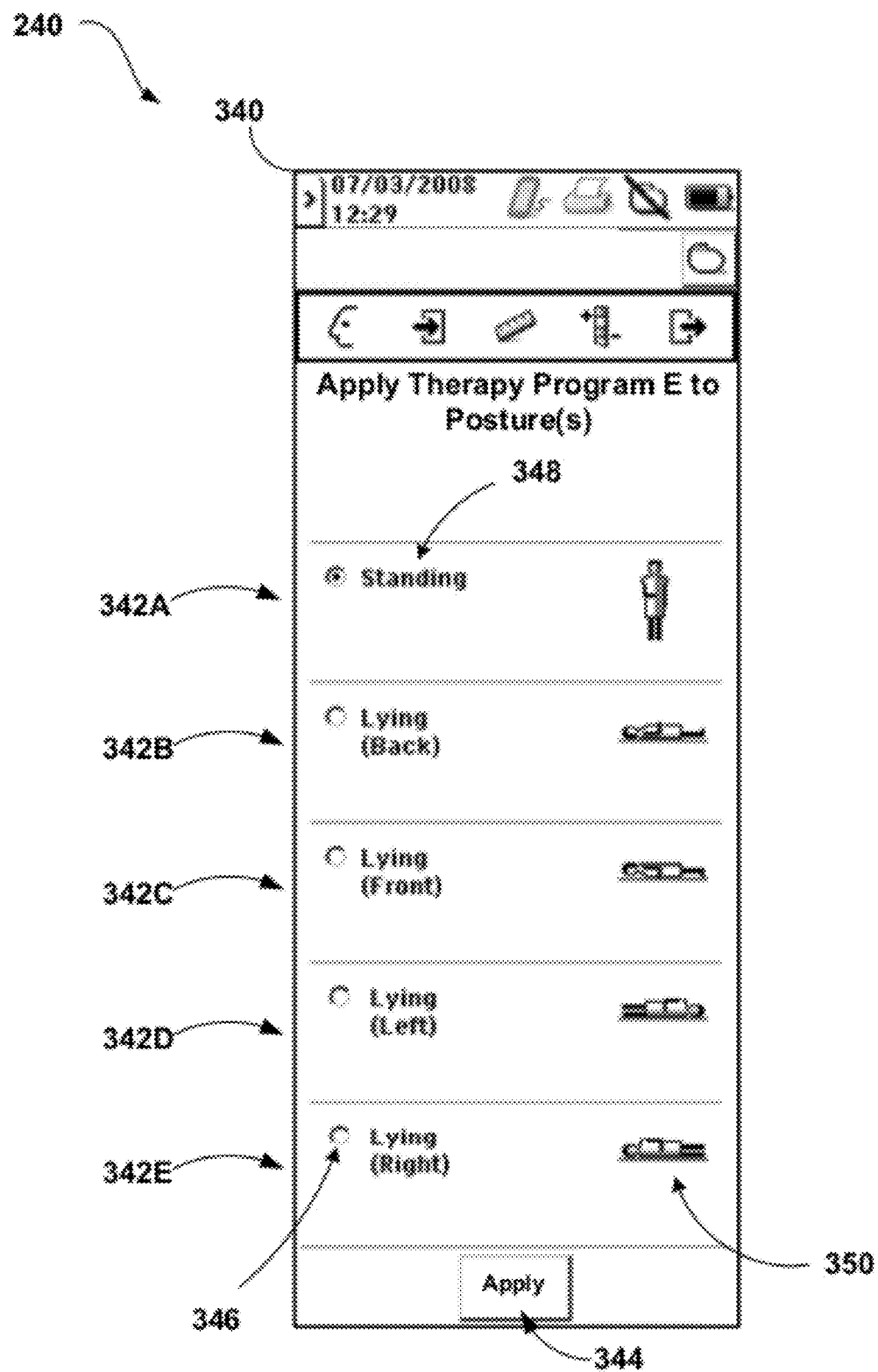
FIG. 15 is a conceptual diagram illustrating an example user interface for applying the selected therapy program to one or more subsequent therapy programs based on patient posture.
Figure 16:
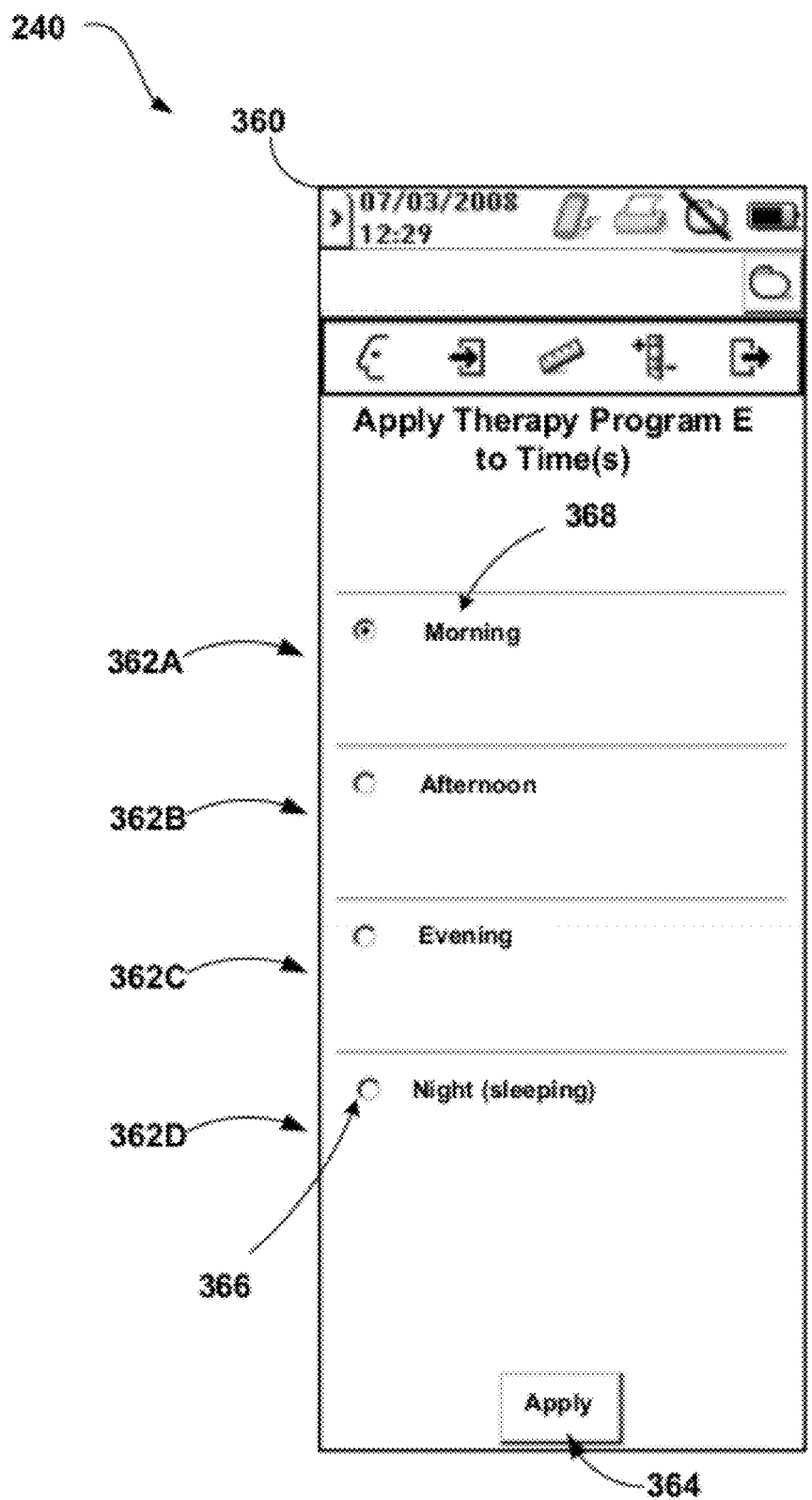
FIG. 16 is a conceptual diagram illustrating an example for applying the selected therapy program to one or more subsequent therapy programs based on the time at which the therapy is to be delivered to a patient.

FIGS. 14-16 are conceptual diagrams illustrating example screens of user interface 240 of FIG. 12 that programmer 20 may present to aid patient 12 (or another user) in the manual adjustment of posture-responsive therapy based on therapy information that correlates input times, posture states, and therapy programs.

FIG. 14 is a conceptual diagram illustrating screen 320 of user interface 240 that presents options with which patient 12 may input therapy adjustments for posture-responsive therapy. In particular, screen 320 provides options with which patient 12 can select a therapy program from a group of therapy programs 334 that are correlated with posture states 328, input times 330, and patient efficacy inputs 332. In the example shown in FIG. 14, patient 12 utilizes therapy program selection options 322 and selects program button 324 to select a therapy program for association with one or more patient posture states for subsequent posture-responsive therapy delivery.

Therapy program selection options 322 include check-box selection inputs 326, posture state description 328, patient input times 330, efficacy level of patient inputs 332, and therapy programs 334. Patient 12 uses check-boxes 326 to select, e.g., one of therapy programs 334 to define subsequent therapy delivered by IMD 14 to patient 12. Although the inputs by which patient 12 selects a therapy program are shown in FIG. 14 as check-boxes 326, in other examples external programmer 20 may use drop down lists, radio buttons, text boxes, or another appropriate software control that allows patient 12 to select a program. In FIG. 14, patient 12 may select the therapy program with the highest level of efficacy input for a single posture state such as, e.g., the standing posture as shown in FIG. 14. In another example, patient 12 may select the therapy program with the highest level of efficacy for all posture states. After selecting one of check-boxes 326 corresponding to one of therapy programs 334, patient 12 can use select therapy program button 324 to confirm the selection.

Once patient 12 selects the desired therapy program using user interface 240 based on the correlations between patient input, input time, sensed posture, and therapy program, patient 12 can use external programmer 20 to apply the selected program to posture-responsive therapy to be delivered to patient 12 at a subsequent time. In general, patient 12 may use external programmer 20 to associate the selected program with a particular posture state to guide subsequent posture-responsive therapy delivery.

In one example, patient 12 uses programmer 20 to adjust one or more therapy parameter values of a first therapy program associated with a first posture state to have substantially similar values as a second therapy program that is associated with a highest relatively efficacy input for the first posture state. For example, patient 12 may update the therapy program associated with a standing posture state in memory 82 of IMD 14 to include the same therapy parameter values as the therapy program that patient 12 previously received and associated with a highest level of efficacy for the standing posture state.

In another example, patient 12 uses programmer 20 to adjust one or more therapy parameter values of a first therapy program associated with a first posture state to have substantially similar values as a second therapy program that is associated with a highest relatively efficacy input, regardless of the posture state patient 12 occupied when the second therapy program was delivered. For example, patient 12 may manually update the therapy program associated with a standing posture state in memory 82 of IMD 14 to include the same therapy parameter values as the therapy program that patient 12 previously received and associated with a highest level of efficacy for all the posture states.

In still another example, patient 12 adjusts a therapy program to be implemented by IMD 14 at a particular time of day for a particular posture state based on a therapy program that is correlated with a patient input with a highest level of efficacy, where the patient input was received at or around the particular time of day. In this way, patient 12 may adjust posture-responsive therapy delivery for a particular time of therapy delivery. This may be useful if, for example, IMD 14 selects different therapy programs for the same posture state based on the time of day at which the posture state is sensed. For example, IMD 14 may provide therapy delivery according to a first therapy program if a posture state is sensed at a first time of day and IMD 14 may provide therapy delivery according to a second therapy program if the posture state is sensed at a second time of day. As an example, patient 12 can adjust a therapy program associated with a lying down posture state based on a therapy program associated with the highest patient efficacy rating and previously-implemented by IMD 14 for the lying down posture state at a particular time of day.

In addition to adjusting a therapy program associated with a posture state based on the highest level of patient efficacy input for the posture state, for all posture states, or for a particular patient input time, patient 12 may use external programmer 20 to adjust a plurality of therapy programs for one or more posture states based on a single correlation between patient input, patient input time, sensed posture state, and therapy program. FIGS. 15 and 16 are conceptual diagrams illustrating screens 340 and 360, respectively, of user interface 240 that may be presented by programmer 20. Screen 340 in FIG. 15 may be used by patient 12 to apply selected therapy program E (see FIG. 14) to one or more subsequent therapy programs to be delivered by IMD 14 based on the sensed posture state of patient 12, while screen 360 of FIG. 16 may be used by patient 12 to apply selected program E to subsequent programs based on the time or times at which the programs are to be delivered. Therapy program E is merely referenced as one example therapy program that may be associated with one or more therapy programs based on a single correlation between patient input, patient input time, sensed posture state, and therapy program determined based on historical posture-responsive therapy information.

In FIG. 15, patient 12 interacts with screen 340 presented by external programmer 20 to adjust one or more therapy programs implemented by IMD 14 for posture-responsive therapy delivery based on a single correlation between a patient input, patient input time, sensed posture state, and therapy program. In the example shown in FIG. 15, patient 12 utilizes posture state selection options 342 and apply program button 344 on screen 340 to apply therapy program E to all subsequent therapy programs to be delivered while patient 12 is in the standing posture state 342A.

Posture state selection options 342A-342E (collectively "posture state selection options 342") include radio button selection inputs 346, posture state descriptions 348, and posture state icons 350. Patient 12 selects the posture state with which therapy program E should be applied for future posture-responsive therapy delivery by IMD 14 using radio buttons 346. In the example shown in FIG. 15, patient 12 selects the radio button 346 associated with standing posture state 342A to indicate that selected therapy program E should be applied to the standing posture state 342A. Although the inputs by which patient 12 selects a posture state are shown in FIG. 15 as radio buttons 346, in other examples external programmer 20 may use drop down lists, check-boxes, or another appropriate software control that allows patient 12 to select posture states.

After selecting one of radio buttons 346 corresponding to standing posture state 342A, patient 12 can use apply program button 344 to apply therapy program E to all subsequent therapy delivered to patient 12 in the standing posture state. Although in the example of FIG. 15 patient 12 selects a single posture state for associating with therapy program E for subsequent posture-responsive therapy delivery, other examples include variations of selecting single or multiple posture states to be associated with one or more therapy programs for subsequent posture-responsive therapy delivery by IMD 14. For example, patient 12 may interact with screen 340 shown in FIG. 15 to associate therapy program E with standing posture state 342A and lying right posture state 342E for subsequent posture-responsive therapy delivered by IMD 14 to patient 12 at all times or at a particular time of day.

Instead of associating selected therapy program E with one or more posture states with the aid of a graphical user interface presented by programmer 12, patient 12 may associate therapy program E with a particular time of day, e.g., the time of day subsequent therapy programs will be delivered by IMD 14 to patient 12. In FIG. 16, patient 12 uses external programmer 20 to instruct IMD 14 to adjust a therapy program delivered to patient 12 in the morning. The "morning" may be defined as any suitable range of time, such as between 6:00 a.m. and 11:59 a.m.

Patient 12 utilizes time of day selection options 362A-362D (collectively "time of day selection options 362") and applies program button 364 on screen 360 to select and apply selected therapy program E to all subsequent therapy programs to be delivered while the patient is in one or more posture states in the "morning" time of day 362A. In this way, IMD 14 may not necessarily deliver posture-responsive therapy to patient 12, but, rather, may deliver therapy to patient 12 based on the time of day, e.g., "morning." However, IMD 14 may also add posture to the determination of which therapy is appropriate for a particular time of day. In some examples, therefore, IMD 14 may combine the techniques described with reference to FIGS. 15 and 16 to adjust therapy delivered to patient 12 based on a time at which the therapy is delivered and the posture state occupied by the patient at that time. For example, patient 12 may associate selected therapy program E with therapy to be delivered while the patient is in standing posture state 342A only at a particular time of day, e.g., in the "morning."

Referring again to FIG. 16, time of day selection options 362 include radio button selection inputs 366 and time of day descriptions 368. Patient 12 uses radio buttons 366 to indicate that selected therapy program E should be applied to all subsequent therapy programs delivered in the morning time of day 362A and while patient is in one or more posture states. In addition to or instead of radio buttons 346, external programmer 20 may use drop down lists, check-boxes, or another appropriate software control that allows patient 12 to select a time of day to which to apply selected therapy program E. After selecting one of radio buttons 366 corresponding to morning time of day 362A, patient 12 can use apply program button 364 to apply therapy program E to all subsequent therapy delivered to patient 12 in the morning.

Many features of posture-responsive therapy evaluation and programming are described herein. For example, examples disclosed herein provide interactive presentations of patient efficacy inputs correlated with input time, sensed posture state, and therapy program as a function of time. Users, including, e.g. patients and clinicians may use such presentations to, e.g., review a historical record of patient therapy and correlated efficacy in a variety of posture states over a period of time through a single graph. The user may also easily adjust one or more subsequently applied therapy programs based on the correlations plotted in the graph presented by the programmer. The adjustments may be applied to subsequent therapy programs in a variety of ways including, e.g., based on the subsequent posture state of the patient or the subsequent time at which the therapy is to be delivered to the patient.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to cause one or more processors to support one or more aspects of the functionality described in this disclosure.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that my benefit from the subject matter of this disclosure.

Many examples have been described. Various modifications may be made without departing from the scope of the invention as defined by the claims that follow. These and other embodiments are within the scope of the following claims.

The invention claimed is:
1. A method comprising:
receiving a plurality of inputs from a patient via a programming device, wherein the plurality of inputs are indicative of an efficacy of therapy delivered to the patient by a medical device over a period of time, and wherein the medical device delivers posture-responsive therapy to the patient;
correlating, with at least one of the programming device or the medical device, each of the patient inputs to a patient input time, the patient input time being a time at which the respective patient input was received, a sensed posture state of the patient, and a therapy program defining therapy delivered by the medical device when the patient occupied the sensed posture state;

presenting the patient inputs and the correlated sensed posture states, therapy programs, and patient input times as a function of time to a user via a display device; and adjusting the posture-responsive therapy delivered by the medical device based on one or more of the correlations between the patient inputs, the patient input times, the sensed posture states, and the therapy programs.

2. The method of claim 1, wherein presenting the patient inputs and correlated sensed posture states, therapy programs, and patient input times as a function of time to a user comprises presenting a step function graph of the patient inputs and correlated sensed posture states, therapy programs, and patient input times as a function of time.

3. The method of claim 2, wherein the step function graph comprises a first step function plot of patient posture states as a function of time and a second step function plot of therapy programs as a function of time.

4. The method of claim 3, wherein each of the patient inputs are represented by substantially vertical lines connecting a patient posture state on the first step function plot to a therapy program on the second step function plot at a time at which the patient input was received, the posture state of the patient was sensed, and therapy defined by the therapy program was delivered.

5. The method of claim 4, wherein each of the vertical lines is annotated with a symbol indicative of one of a range of efficacy levels.

6. The method of claim 5, wherein the range of efficacy levels comprises a satisfactory level and a spectrum of levels above and below the satisfactory level.

7. The method of claim 1, wherein adjusting the posture-responsive therapy delivered by the medical device comprises determining which patient input of the patient inputs correlated with a particular posture state comprises a relatively highest level of efficacy for the particular posture state and associating a therapy program correlated to the patient input with the relatively highest level of efficacy for the particular posture state with the particular posture state, wherein the medical device delivers therapy to the patient according to the therapy program when the particular posture state is detected.

8. The method of claim 1, wherein adjusting the posture-responsive therapy delivered by the medical device comprises determining which patient input of the plurality of patient inputs comprises a relatively highest level of efficacy for all the posture states and associating a therapy program correlated to the patient input with the relatively highest level of efficacy for all the posture states with a particular posture state.

9. The method of claim 1, wherein adjusting the posture-responsive therapy delivered by the medical device comprises determining which patient input correlated with a particular patient input time comprises a relatively highest level of efficacy for the particular patient input time and selecting a subsequent therapy program to be delivered at a subsequent time to be a therapy program correlated to the patient input with the relatively highest level of efficacy for the particular patient input time, wherein the particular patient input time is similar to the subsequent time.

10. The method of claim 9, wherein patient input time comprises a time of day.

11. The method of claim 1, wherein adjusting the posture-responsive therapy delivered by the medical device comprises adjusting a plurality of therapy programs associated with a plurality of respective posture states based on one correlation between a patient input, patient input time, sensed posture state, and therapy program.

12. The method of claim 1, wherein adjusting the posture-responsive therapy delivered by the medical device comprises adjusting a plurality of therapy programs associated with a particular posture state based on one correlation between a patient input, patient input time, sensed posture state, and therapy program.

13. The method of claim 1, wherein adjusting the posture-responsive therapy delivered by the medical device comprises receiving a selection input from the user selecting a therapy program correlated to patient input, patient input time, and sensed posture state and associating the selected therapy program with one or more posture states.

14. The method of claim 1, wherein receiving a plurality of inputs from a patient indicative of an efficacy of therapy delivered to the patient by a medical device over a period of time comprises receiving a plurality of inputs from a patient indicative of an efficacy of one or more parameters included in one or more therapy programs that define the therapy delivered to the patient by the medical device over the period of time.

15. The method of claim 1, wherein correlating patient inputs to patient input times, sensed posture states, and therapy programs comprises correlating each of the patient inputs to a time at which the input was received, a sensed posture state of the patient at the time the patient input was received, and a therapy program defining therapy delivered by the medical device when the patient occupied the sensed posture state.

16. The method of claim 1, wherein correlating patient inputs to patient input times, sensed posture states, and therapy programs comprises correlating each of the patient inputs to a time at which the input was received, a sensed posture state of the patient at a time other than the time the patient input was received, and a therapy program defining therapy delivered by the medical device when the patient occupied the sensed posture state.

17. The method of claim 1, wherein the programming device and the display device are separate devices.

18. The method of claim 1, wherein the programming device comprises the display device.

19. A non-transitory computer-readable medium comprising instructions for causing a programmable processor to carry out a method comprising:

receiving a plurality of inputs from a patient indicative of an efficacy of therapy delivered to the patient by a medical device over a period of time, wherein the medical device delivers posture-responsive therapy to the patient;

correlating each of the patient inputs to a patient input time, the patient input time being a time at which the respective patient input was received, a sensed posture state of the patient, and a therapy program defining therapy delivered by the medical device when the patient occupied the sensed posture state;

presenting the patient inputs and the correlated sensed posture states, therapy programs, and patient input times as a function of time to a user via a display device; and adjusting the posture-responsive therapy delivered by the medical device based on one or more of the correlations between the patient inputs, the patient input times, the sensed posture states, and the therapy programs.

20. The non-transitory computer-readable medium of claim 19, wherein the instructions cause the programmable processor to present the patient inputs and correlated sensed posture states, therapy programs, and patient input times as a function of time to a user by at least presenting a step function graph of the patient inputs and correlated sensed posture states, therapy programs, and patient input times as a function of time.

21. The non-transitory computer-readable medium of claim 20, wherein the step function graph comprises a first step function plot of patient posture states as a function of time and a second step function plot of therapy programs as a function of time.

22. The non-transitory computer-readable medium of claim 21, wherein each of the patient inputs are represented by substantially vertical lines connecting a patient posture state on the first step function plot to a therapy program on the second step function plot at a time at which the patient input was received, the posture state of the patient was sensed, and therapy defined by the therapy program was delivered.

23. The non-transitory computer-readable medium of claim 22, wherein each of the patient input vertical lines is annotated with a symbol indicative of one of a range of efficacy levels.

24. The non-transitory computer-readable medium of claim 19, wherein the instructions cause the programmable processor to adjust the posture-responsive therapy delivered by the medical device by at least determining which one of the patient inputs for a particular posture state comprises a relatively highest level of efficacy for the particular posture state and associating a therapy program correlated to the patient input with the relatively highest level of efficacy for the particular posture state with the particular posture state, wherein the medical device delivers therapy to the patient according to the therapy program when the particular posture state is detected.

25. The non-transitory computer-readable medium of claim 19, wherein the instructions cause the programmable processor to adjust the posture-responsive therapy delivered by the medical device by at least determining which one of the patient inputs comprises a relatively highest level of efficacy for all the posture states and associating a therapy program correlated to the patient input with the relatively highest level of efficacy for all the posture states with a particular posture state.

26. The non-transitory computer-readable medium of claim 19, wherein the instructions cause the programmable processor to adjust the posture-responsive therapy delivered by the medical device by at least determining a patient input for a particular patient input time comprising a relatively highest level of efficacy for the particular patient input time and selecting a subsequent therapy program to be delivered at a subsequent time to be a therapy program correlated to the patient input with the relatively highest level of efficacy for the particular patient input time, wherein the particular patient input time is similar to the subsequent time.

27. The non-transitory computer-readable medium of claim 19, wherein the instructions cause the programmable processor to adjust the posture-responsive therapy delivered by the medical device by at least adjusting a plurality of therapy programs associated with a plurality of respective posture states based on one correlation between a patient input, patient input time, sensed posture state, and therapy program.

28. The non-transitory computer-readable medium of claim 19, wherein the instructions cause the programmable processor to adjust the posture-responsive therapy delivered by the medical device by at least adjusting a plurality of therapy programs associated with a particular posture state based on one correlation between a patient input, patient input time, sensed posture state, and therapy program.

29. The non-transitory computer-readable medium of claim 19, wherein the instructions cause the programmable processor to adjust the posture-responsive therapy delivered by the medical device by at least receiving a selection input from the user selecting a therapy program correlated to patient input, patient input time, and sensed posture state and associating the selected therapy program with one or more posture states.

30. The non-transitory computer-readable medium of claim 19, wherein the instructions cause the programmable processor to adjust the posture-responsive therapy delivered by the medical device by at least receiving a selection input from the user indicating that a plurality of subsequent therapy programs should be set to one of the therapy programs correlated to patient input, patient input time, and sensed posture state.

31. The non-transitory computer-readable medium of claim 19, wherein the instructions cause the programmable processor to receive a plurality of inputs from a patient indicative of an efficacy of therapy delivered to the patient by a medical device over a period of time by at least receiving a plurality of inputs from a patient indicative of an efficacy of one or more parameters included in one or more therapy programs that define the therapy delivered to the patient by the medical device over the period of time.

32. The non-transitory computer-readable medium of claim 19, wherein the instructions cause the programmable processor to correlate patient inputs to patient input times, sensed posture states, and therapy programs by at least correlating each of the patient inputs to a time at which the input was received, a sensed posture state of the patient at the time the patient input was received, and a therapy program defining therapy delivered by the medical device when the patient occupied the sensed posture state.

33. The non-transitory computer-readable medium of claim 19, in the instructions cause the programmable processor to correlate patient inputs to patient input times, sensed posture states, and therapy programs by at least correlating each of the patient inputs to a time at which the input was received, a sensed posture state of the patient at a time other than the time the patient input was received, and a therapy program defining therapy delivered by the medical device when the patient occupied the sensed posture state.

34. An implantable medical system configured to deliver posture-responsive therapy to a patient, the system comprising:
    an implantable medical device (IMD) that senses patient posture states and delivers therapy to the patient by adjusting one or more therapy parameter values based on a sensed patient posture state;
    a user interface;
    one or more processors that receive a plurality of inputs from the patient via the user interface, where the plurality of inputs are indicative of an efficacy of therapy delivered to the patient by the IMD over a period of time, correlate each of the patient inputs to a patient input time, the patient input comprising a time at which the respective patient input was received, a sensed posture state of the patient, and a therapy program defining therapy delivered by the IMD when the patient occupied the sensed posture state, present the patient inputs and the correlated sensed posture states, therapy programs, and patient input times as a function of time to a user via the user interface, and adjust the posture-responsive therapy delivered by the IMD based on one or more of the correlations between the patient inputs, the patient input times, the sensed posture states, and the therapy programs.

35. The system of claim 34, wherein the implantable medical device comprises the one or more processors.

36. The system of claim 34, further comprising an external programmer that includes the one or more processors and the user interface.

37. The system of claim 34, wherein the implantable medical device comprises at least one of the one or more processors, the system further comprising an external programmer that includes at least one of the one or more processors.

38. The system of claim 37, wherein the external programmer includes the user interface, and the at least one of the one or more processors included in the external programmer receives the plurality of inputs from the patient, and presents the patient inputs and correlated sensed posture states, therapy programs, and patient input times as a function of time to the user via the user interface.

39. The system of claim 34, wherein the one or more processors present the patient inputs and correlated sensed posture states, therapy programs, and patient input times as a function of time to a user by at least presenting a step function graph of the patient inputs and correlated sensed posture states, therapy programs, and patient input times as a function of time.

40. The system of claim 34, wherein the one or more processors adjust the posture-responsive therapy by at least determining which one of the patient inputs for a particular posture state comprises a relatively highest level of efficacy for the particular posture state and associating a therapy program correlated to the patient input with the relatively highest level of efficacy for the particular posture state with the particular posture state, wherein the implantable medical device delivers therapy to the patient according to the therapy program when the particular posture state is detected.

41. The system of claim 34, wherein the one or more processors adjust the posture-responsive therapy by at least determining which one of the patient inputs comprises a relatively highest level of efficacy for all the posture states and associating a therapy program correlated to the patient input with the relatively highest level of efficacy for all the posture states with a particular posture state.

42. The system of claim 34, wherein the one or more processors adjust the posture-responsive therapy by at least determining a patient input for a particular patient input time comprising a relatively highest level of efficacy for the particular patient input time and selecting a subsequent therapy program to be delivered at a subsequent time to be a therapy program correlated to the patient input with the relatively highest level of efficacy for the particular patient input time, wherein the particular patient input time is similar to the subsequent time.

43. The system of claim 34, wherein the one or more processors adjust the posture-responsive therapy by at least adjusting a plurality of therapy programs associated with a plurality of respective posture states based on one correlation between a patient input, patient input time, sensed posture state, and therapy program.

44. The system of claim 34, wherein the one or more processors adjust the posture-responsive therapy by at least adjusting a plurality of therapy programs associated with a particular posture state based on one correlation between a patient input, patient input time, sensed posture state, and therapy program.

45. The system of claim 34, wherein the one or more processors adjust the posture-responsive therapy by at least receiving a selection input from the user via the user interface, the selection input selecting a therapy program correlated to patient input, patient input time, and sensed posture state, and associating the selected therapy program with one or more posture states.

* * * * *